United States Patent
Burnet et al.

(10) Patent No.: US 9,617,221 B2
(45) Date of Patent: Apr. 11, 2017

(54) KINASE MODULATORS FOR THE TREATMENT OF CANCER

(75) Inventors: Michael W. Burnet, Tübingen (DE); Jan-Hinrich Guse, Tubingen-Buhl (DE); Christiane Bauerlein, Ofterdingen (DE); Ulrike Hahn, Ditzingen (DE)

(73) Assignee: Synovo GmbH, Tubingen (DE)

( * ) Notice: Subject to any disclaimer, the term of this patent is extended or adjusted under 35 U.S.C. 154(b) by 127 days.

(21) Appl. No.: 13/586,814

(22) Filed: Aug. 15, 2012

(65) Prior Publication Data
US 2013/0045938 A1 Feb. 21, 2013

Related U.S. Application Data

(63) Continuation of application No. PCT/US2011/024947, filed on Feb. 15, 2011.

(60) Provisional application No. 61/369,798, filed on Aug. 2, 2010, provisional application No. 61/304,502, filed on Feb. 15, 2010.

(51) Int. Cl.
| | |
|---|---|
| C07D 231/38 | (2006.01) |
| A61K 31/415 | (2006.01) |
| C07H 13/02 | (2006.01) |
| C07D 471/04 | (2006.01) |
| C07D 417/04 | (2006.01) |
| A61K 31/4439 | (2006.01) |
| A61K 31/519 | (2006.01) |
| C07D 401/04 | (2006.01) |
| A61K 45/06 | (2006.01) |
| A61K 47/48 | (2006.01) |
| C07D 405/14 | (2006.01) |

(52) U.S. Cl.
CPC .......... *C07D 231/38* (2013.01); *A61K 31/415* (2013.01); *A61K 31/4439* (2013.01); *A61K 31/519* (2013.01); *A61K 45/06* (2013.01); *A61K 47/481* (2013.01); *C07D 401/04* (2013.01); *C07D 405/14* (2013.01); *C07D 417/04* (2013.01); *C07D 471/04* (2013.01); *C07H 13/02* (2013.01)

(58) Field of Classification Search
CPC ............................ A61K 31/415; C07D 231/38
See application file for complete search history.

(56) References Cited

U.S. PATENT DOCUMENTS

| | | | |
|---|---|---|---|
| 6,316,466 | B1 | 11/2001 | Goldstein et al. |
| 2006/0172959 | A1 | 8/2006 | Smith et al. |
| 2008/0286286 | A1 | 11/2008 | Liu et al. |
| 2009/0098137 | A1* | 4/2009 | Burke et al. ............... 424/141.1 |

FOREIGN PATENT DOCUMENTS

| | | |
|---|---|---|
| WO | WO-2005-009973 | 2/2005 |
| WO | WO-2008-150899 | 12/2008 |

OTHER PUBLICATIONS

Regan et al., J. Med. Chem., 2002, 45, p. 2994-3008.*
Trauzold et al., Oncogene, 2006, 25, p. 7434-7439.*
Merino et al., Expert Opin. Ther. Targets, 2007, 11(10), p. 1299-1314.*
Goldstein et al., J. Med. Chem., 2006, 49, p. 1562-1575.*
Yong et al., Expert Opin. Investig. Drugs, 2009, 18(12), p. 1893-1905.*
International Search Report and Written Opinion mailed Oct. 13, 2011, in corresponding PCT Application No. PCT/US2011/024947.

* cited by examiner

*Primary Examiner* — Jonathan S Lau
(74) *Attorney, Agent, or Firm* — Wolf, Greenfield & Sacks, P.C.

(57) ABSTRACT

A method of treating cancer in which a compound that inhibits the expression, production or release of IL-10 by immune cells is combined with a compound that stimulates the production of IL-12 when given in combination with, or in the presence of TNFa. Said method is effective when provided in addition to standard therapies, notably chemotherapy using cytotoxic drugs and other forms of immune therapy including therapeutic vaccines.

4 Claims, 14 Drawing Sheets a $R^2$ = phenylethyl  d $R^2$ = ethyl  g $R^2$ = sec-butyl
b $R^2$ = benzyl  e $R^2$ = methyl  h $R^2$ = isopropyl
c $R^2$ = iso-butyl  f $R^2$ = 3-methylbut-2-yl  i $R^2$ = tetrahydropyran-4-yl Reagents and conditions: (i) $R^3$-Br, NaH, DMF, 0 °C; (ii) $R^3$-NH$_2$ or $R^3$-NH$_2$·HCl, Pd$_2$(dba)$_3$, t-BuONa, BINAP, toluene, reflux temperature; (iii) Boc$_2$O, DMAP, CH$_2$Cl$_2$, r.t.

Scheme 1

Scheme 2

Scheme 3

(For synthesis examples se: S. A. Laufer et al., J. med. chem. 51 (14), 4122-4149, 2008)

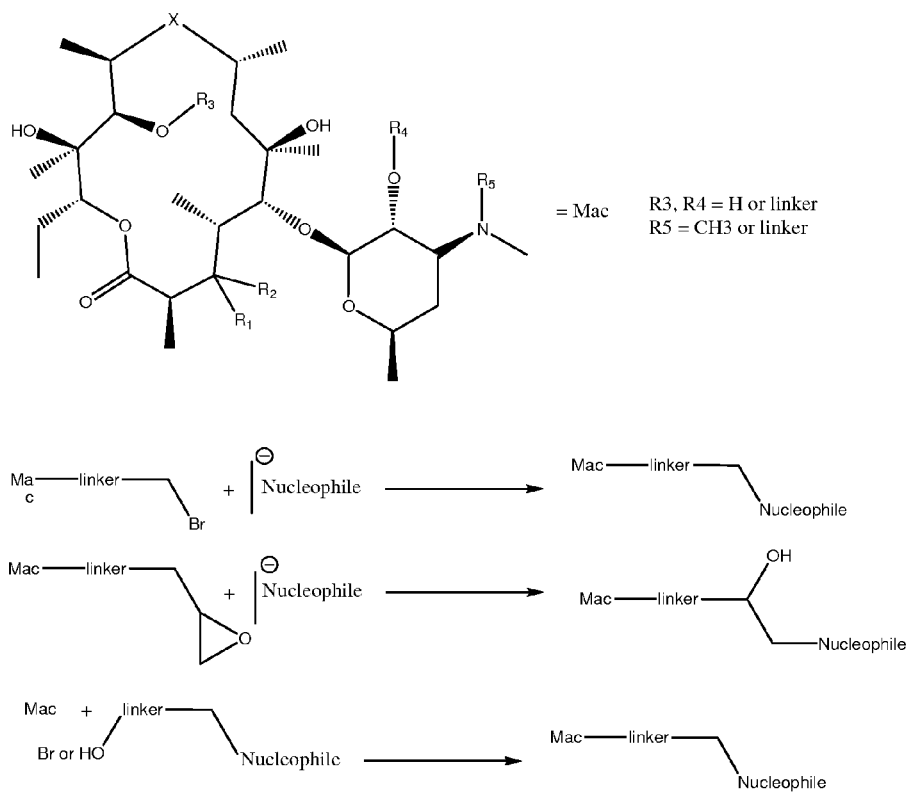
Figure 7 – General coupling scheme for macrolides and kinase inhibitors.
R1 = H and R2 = OH or O-cladinosyl or
R1, R2 = (=O)
X = (C=O) or (C=N-OH) or -[N(CH3)-CH2]- or -[CH2-N(CH3)]- n = 2-10
m = 2-10 n = 1-10
m = 2-10 n = 2-10 n = 2-10
m = 2-10 n = 1-10

Example structures of macrolide-kinase inhibitor conjugates and their precursors Example structures of macrolide-kinase inhibitor conjugates and their precursors Example structures of macrolide-kinase inhibitor conjugates and their precursors Example structures of macrolide-kinase inhibitor conjugates and their precursors Example structures of macrolide-kinase inhibitor conjugates and their precursors Example structures of macrolide-kinase inhibitor conjugates and their precursors Example structures of macrolide-kinase inhibitor conjugates and their precursors

51

52

53

54

55

56

57

KINASE MODULATORS FOR THE TREATMENT OF CANCER

CROSS-REFERENCE TO RELATED APPLICATIONS

This application is a continuation of PCT International Patent Application No. PCT/US2011/024947, filed Feb. 15, 2011, which claims the benefit of and priority to U.S. Provisional Patent Application Nos. 61/304,502, filed Feb. 15, 2010, and 61/369,798, filed Aug. 2, 2010. The contents of each of these applications are incorporated herein by reference in their entirety.

BACKGROUND OF THE INVENTION

The treatment of cancer via the re-activation of the immune system is a long-standing goal of medical research. There have been many attempts to stimulate an immune response to cancer including the application of therapeutic vaccines (Umansky et al.), the use of immune stimulants such as Toll-Like Receptor Agonists (TLRa) (Fahey et al.), the use of autologous cell vaccination in combination with immune stimulators including TLRa and Annexin V (US2006293226), the use of therapeutic acute infections and the use of expression constructs containing cancer antigens in a virus like vehicle (Pascolo).

Although effective in certain patients these strategies have not provided general means to treat cancer. One of the many reasons for this is that cancers are by definition immune evasive given that their very detection is a result of their having successfully avoided normal immune responses. One of the evasion strategies of cancers is the production of an immune suppressive environment around the tumour through the secretion of various signals and cytokines notably TGFbeta. Other authors have noted that Nuclear Factor kappa B (NF-kB) is a critical mediator of ongenic processes, although it is not itself mutated in cancer (Karin) and probably plays a role via underlying inflammation in permitting tumour expansion.

It is now apparent that tumour macrophage are an important component of this immune suppression process. Hagemann et al. (1988), noted that macrophage that support tumour expansion were IL-10 high, IL-12 low, scavenger receptor expression high, and TNF-α high. Genetic inhibition of NF-kB activation by ablation of inhibitor of kappa kinase B (IKKB) resulted in a reversion of this phenotype and a reduction in tumour growth.

NF-kB is well known to interact with p38 kinase in stimulated cells, and inhibitors of p38 kinase can modulate the degree to which NF-kB dependant gene products are produced (Ulive et al.). p38 kinase has been widely investigated for a potential role in cancer therapy because of its general importance in cell cycle control, proliferation and differentiation (Bradham and McClay).

With this knowledge, many workers have attempted to modulate cancer using p38 kinase inhibitors. However, many such studies have been done with prototypic, non-selective p38 inhibitors and data, where positive, have tended to show modest improvements in therapy (see Han et al., 2009). In certain instances, improvements in therapy are reliant on the p38-MAPK pathway to induce apoptosis (Kadowaki et al., 2009) and where it is inhibited by a non-selective p38 kinase inhibitor, there is a reduction of anti-tumour effect (see Liu et al., 2009). In certain instances it has been demonstrated that the resistance of certain tumours to the effects of a therapeutic antibody are mediated by the MAP kinase pathway. In such a setting the addition of a MAP kinase inhibitor, in this case BIRB 796, increased cytotoxic effect of bortezomib (Yasui et al., 2007).

Indeed almost all p38 MAP kinase inhibitors are tested for lack of cytotoxicity using cell-lines which are often of tumour derived. It is, therefore, not surprising that p38 MAP kinase inhibitors are not known widely as anti-cancer agents or for direct anti-tumor activity.

Less appreciated is the fact that p38 and related kinase inhibitors have specific temporal and spatial effects that are dependant on the cell environment in which they act. The environment of a tumour is specific, and the signaling in the cells in that environment is different to that say, in the peritoneum of a normal animal exposed to bacterial antigens. Thus, recognition of the value of kinase inhibitors for the promotion of anti-tumour immune responses is reliant on evaluating them in that context. An example of this is provided by Wang et al., 2006 who show that dendritic cells rely on p38 to respond to certain tumour signals emanating from multiple myeloma like cell lines.

SUMMARY OF THE INVENTION

The invention relates to compounds useful in treating cancer by means of a promotion of the immune system anti-tumour response in which one or more compounds that, alone or together increase the production of the cytokine IL-12 and reduce the expression or production of the cytokine IL-10 in tumour macrophage, are administered to an organism in need of same. The compounds may be modulators of kinase enzymes and may modulate in particular p38 kinase amongst others. In a preferred embodiment, their cytokine suppressing activity is dependant on the presence of other cytokines, notably TNFalpha. In a further preferred embodiment, the compounds are not inhibitors of the pro-inflammatory cytokines IL-6 at the concentrations at which they exert effects on IL-12 or IL-10.

The invention further relates to a method for identifying such compounds based on the screening of compounds using macrophages in the presence of a tumour derived medium and identifying compounds that are associated with a decrease in IL-10, an increase in IL-12 and little or no effect on TNF, or IL-6.

Thus, in one aspect, the invention provides a method of treating cancer in a subject in need thereof, the method comprising administering one or more compounds to the subject to enhance IL-12 production or inhibit IL-10 production. In certain embodiments, at least one compound is a compound to enhance IL-12 production. In certain embodiments, at least one compound is a compound to inhibit IL-10 production. In certain embodiments, a first compound is a compound to inhibit IL-10 production and a second compound is a compound to inhibit IL-10 production. In certain embodiments, the IL-10 inhibiting activity and the IL-12 stimulating activity are present in different compounds; in certain embodiments, the compounds are administered together.

In certain embodiments, the compounds are small molecules below MW 1500. In certain embodiments, the compounds are kinase inhibitors, In certain embodiments, one or both of the compounds are inhibitors of p38 kinase. In certain embodiments, the compound inhibiting IL-10 is represented by the following structure:

Formula 1

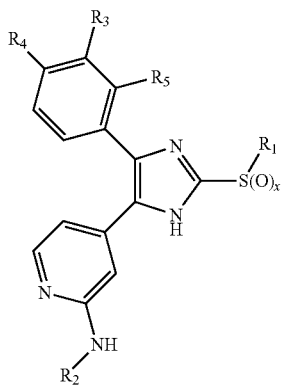

wherein x=0, 1, 2

R₁=2-hydroxypropyl, 3-hydroxypropyl, 2-hydroxyethyl, 2,3-dihydroxypropyl, 2-hydroxy-3-aminopropyl, 2-hydroxy-3-aminobutyl, 3,4-dihydroxybutyl, 2,3,4-trihydroxybutyl, —(CH₂)ₙ—COR with R═OH, O-alkyl (C₁-C₄), O-alkylaryl, NH₂, NHMe, NHOH, and n=1, 2, 3, 4, 5, —CH₂—P═O(OR)₂ with R═H, CH₃, CH₂CH₃, —CH₂—(CH₂)ₘ—S(═O)ₙ—R with R=alkyl (C₁-C₅), OH, NH₂, and m=1, 2, 3 and, n=0, 1, 2, glycidyl, 3-methylglycidyl, —CH₂—CHOH—COR with R═OH, OMe, OEt, NH2, NHOH, —CH(CH₂OH)—COR with R═OH, OMe, OEt, NH2, NHOH, —CH₂—CHOH—CN, —CH(CH₂OH)—CN, methyl, phenyl, benzyl, R₂=hydrogen, methyl, ethyl, n-propyl, isopropyl, sec-butyl, isobutyl, tert-butyl, 2-(3-methyl)butyl, cyclopropyl, cyclobutyl, cyclopentyl, 3-pentyl, cyclohexyl, morpholinyl, methylcyclohexyl, methylcyclopentyl, methylmorpholinyl, hydroxycyclohexyl, hydroxycyclopentyl, benzyl, 1-phenylethyl, tetrahydropyran-4-yl, (4-hydroxy)cyclohexyl, 1-(1 phenyl)propyl, 1-indanyl, 1-(1,2,3,4-tetrahydro)naphthyl, 1-(2-phenyl)propyl, 1-(1-methyl-3-phenyl)propyl, 1,2-diphenylethyl, 1,3-diphenyl-2-propyl, (4-tert-butyl)benzyl, 4-fluorobenzyl, 2-(2-para-xylyl)ethyl, (1-naphthyl)methyl, (2-thiophenyl)methyl, 2-(2-thiophenyl)ethyl, (2-benzo[b]thiophenyl)methyl, (2-furyl)methyl, [(5-methyl)furan-2-yl]-methyl, (2-pyridyl)methyl, (3-pyridyl)methyl, (4-pyridyl) methyl, —(C═O)—R₂', R₂'═H, C1-C10 alkyl, hydroxyalkyl, aryl, heteroaryl, or arylalkyl; with alkyl chains being branched or linear, 1,5-dihydroxy-3-pentyl, 1,3-dihydroxy-2-propyl, 2,3-dihydroxy-1-propyl, 3-pentyl, 3-methoxy-1-propyl, 2-methylsulfonylethyl, 3-methyoxypropyl, 2-diethylaminocarbonyl-1-ethyl, R₃═H, halogen, CF₃, OCF₃

R₄═H, halogen, CF₃, OCF₃

R₅═H, halogen, CF₃; or a pharmaceutically acceptable salt thereof.

In certain embodiments, the compound inhibiting IL-10 is represented by the following structure:

Formula 2

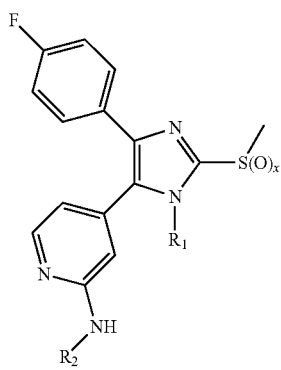

wherein x=0, 1, or 2; R1=methyl, —(CH₂)₂—OCH₃, 2-hydroxyethyl, 2,3-dihydroxypropyl, 1,3-dihydroxy-2-propyl, 1,5-dihydroxy-3-pentyl, cyclohexyl, trans-4-hydroxy-cyclohexyl, 3-hydroxypropyl, 4-tetrahydropyranyl, cyclopropyl, 4-hydroxyethyl, 3-oxo-3-pyrrolidin-1-yl-propyl, 3-pentyl, 2-ethoxycarbonyl-1-ethyl, 2-diethylaminocarbonyl-1-ethyl, 3-bromo-1-propyl, 2-methoxycarbonyl-1-ethyl, 3-oxo-3-piperidin-1-yl-propyl, 2-chloroethyl, 2-carboxy-1-ethyl, 3-oxo-3-morpholin-4-yl-propyl, 3-chloro-1-propyl, 3-carboxypropyl, diethylaminocarbonylmethyl, 4-chlorobutyl, 4-carboxybutyl, 2-oxo-2-morpholin-4-yl-ethyl, 3-fluoropropyl, 2-methylsulfonylethyl, 3-iodopropyl, R₂=phenyl, 1-phenylethyl, 1-cyclohexylethyl, cyclohexyl, (2 hydroxycyclohexyl)methyl, 4-tetrahydropyranyl, 2-hydroxycyclohexyl, (1-hydroxy)-2-propyl, (2-hydroxy)-1-propyl; or a pharmaceutically acceptable salt thereof.

In certain embodiments, the compound inhibiting IL-10 is represented by the following structure:

Formula 3

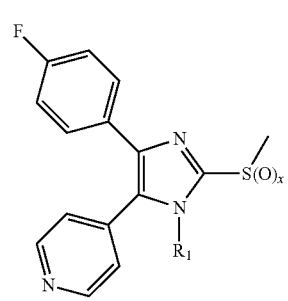

Wherein

X=0, 1, or 2;

R₁=—(NH)—(C═O)—R₁'  R₁'═H, C1-C10 alkyl, hydroxyalkyl, aryl, heteroaryl, or arylalkyl; with alkyl chains being branched or linear —(NH)—R₁';

R₁'═H, C1-C10 alkyl, hydroxyalkyl, aryl, heteroaryl, or arylalkyl; with alkyl chains being branched or linear; or a pharmaceutically acceptable salt thereof.

In certain embodiments, the compound enhancing production of IL-12 is represented by the following structure:

Formula 4

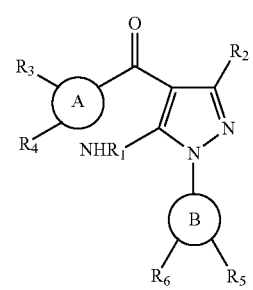

Wherein

R₁=hydrogen or acyl; R₂=hydrogen or alkyl; A=aryl or heteroaryl ring; B=aryl ring; R₃=selected from the group consisting of: (a) amino, alkylamino or dialkylamino; (b) acylamino; (c) optionally substituted heterocyclyl; (d) optionally substituted aryl or heteroaryl; (e) heteroalkyl; (f) heteroalkenyl; (g) heteroalkynyl; (h) heteroalkoxy; (i) heteroalkylamino; (j) optionally substituted heterocyclylalkyl (k) optionally substituted heterocyclylalkenyl; (l) optionally substituted heterocyclylalkynyl; (m) optionally substituted cycloalkoxy, cycloalkylalkyloxy, heterocyclylalkoxy, or heterocyclyloxy; (n) optionally substituted heterocyclylalkylamino; (o) optionally substituted heterocyclylalkylcarbonyl; (p) heteroalkylcarbonyl; (q) optionally substituted cycloalkylamino; (r) —NHSO$_2$R$_6$ where R$_6$ is alkyl, heteroalkyl or optionally substituted heterocyclylalkyl;
(s) —NHSO2NR$_7$R$_8$ where R$_7$ and R$_8$ are, independently of each other, hydrogen, alkyl or heteroalkyl;
(t) —Y-(alkylene)-R$_9$ where: Y is a single bond, —O— —NH— or —S(O)n- (where n is an integer from 0 to 2); and R$_9$ is cyano, optionally substituted heteroaryl, —COOH, —COR$_{10}$, —COOR$_{11}$, —CONR$_{12}$R$_{13}$, —SO$_2$R$_{14}$, —SO$_2$—NR$_{15}$R$_{16}$, —NHSO$_2$R$_{17}$ or NHSO$_2$NR$_{18}$R$_{19}$, where R$_{10}$ is alkyl or optionally substituted heterocycle, R$_{11}$ is alkyl, and R$_{12}$, R$_{13}$, R$_{14}$, R$_{15}$, R$_{16}$, R$_{17}$, R$_{18}$ and R$_{19}$ are, independent of each other, hydrogen, alkyl or heteroalkyl;
(u) —C(NR$_{20}$)(NR$_{21}$R$_{22}$) where R$_{20}$, R$_{21}$ and R$_{22}$ independently represent hydrogen, alkyl or hydroxy, or R$_{20}$ and R$_{21}$ together are —(CH$_2$)$_n$— where n is 2 or 3 and R$_{22}$ is hydrogen or alkyl;
(v) —NHC(X)NR$_{23}$R$_{24}$ where X is —O— or —S— and R$_{23}$ and R$_{24}$ are, independent of each other, hydrogen, alkyl or heteroalkyl;
(w) —CONR$_{25}$R$_{26}$ where R$_{25}$ and R$_{26}$ independently represent hydrogen, alkyl, heteroalkyl or optionally substituted heterocyclylalkyl, or R$_{25}$ and R$_{26}$ together with the nitrogen to which they are attached form an optionally substituted heterocyclyl ring;
(x) —S(O)$_n$R$_{27}$ where n is an integer from 0 to 2, and R$_{27}$ is alkyl, heteroalkyl, optionally substituted cycloalkyl, optionally substituted heterocyclylalkyl, or —NR$_{28}$R$_{29}$ where R$_{28}$ and R$_{29}$ are, independently of each other, hydrogen, alkyl or heteroalkyl;
(y) cycloalkyl alkyl, cycloalkyl alkynyl and cycloalkyl alkynyl, all optionally substituted with alkyl, halo, hydroxy or amino; (z) arylamino alkylene or heteroaryl aminoalkylene;
(aa) Z-alkylene-NR$_{30}$R$_{31}$ or Z-alkylene-OR$_{32}$ where Z is —NH—, —N(alkyl)- or —O—, and R$_{30}$, R$_{31}$ and R$_{32}$ are independently of each other, hydrogen, alkyl or heteroalkyl;
(bb) —OC(O)-alkylene-CO$_2$H or —OC(O)—NR'R" (where R' and R" are independently hydrogen or alkyl);
(cc) heteroarylalkenylene or heteroarylalkynylene;
(dd) X-(alkylene)CH[(CR'R")mOR$_{40}$][(CR'R")nOR$_{40}$] where: X is —O—, —NH—, —NR— (where R is alkyl), —S(O)$_p$— (where p is an integer from 0 to 2); R$_{40}$ is acyl, C(O)OR$_{41}$ (where R$_{41}$ is hydrogen, alkyl, or cycloalkyl); C(O)ONR$_{41}$R$_{42}$ (where R$_{41}$ is as defined above and R$_{42}$ is hydrogen or alkyl); or C(O)NR$_{41}$R$_{42}$ (where R$_{41}$ and R$_{42}$ are as defined above); R' and R", independently, are hydrogen or alkyl; and m and n, independently, are an integer from 0 to 3 provided that m and n are not both zero;
(ee) X-(alkylene)-CH(OH)CH$_2$NHR$_{50}$ where: X is —O—, —NH—, —NR— (where R is alkyl), or —S(O)$_n$— (where n is an integer from 0 to 2); and R$_{50}$ is C(O)OR$_{51}$ and C(O)NR$_{51}$R$_{52}$ (where R$_{52}$ is hydrogen, alkyl, or cycloalkyl and R$_{52}$ is hydrogen or alkyl); and
(ff) X-(alkylene)-CH(NR50)-CH2OH where: X is —O—, —NH—, —NR— (where R is alkyl), or —S(O)$_n$— (where n is an integer from 0 to 2); and R$_{50}$ is C(O)OR$_{51}$ and C(O)NR$_{51}$R$_{52}$ (where R$_{51}$ is hydrogen, alkyl, or cycloalkyl and R$_{52}$ is hydrogen or alkyl);
R$_4$ is selected from the group consisting of:
(a) hydrogen; (b) halo; (c) alkyl; (d) alkoxy; and (e) hydroxy;

R$_5$ is selected from the group consisting of:
(a) hydrogen; (b) halo; (c) alkyl; (d) haloalkyl; (e) thioalkyl; (f) hydroxy; (g) amino; (h) alkylamino; (i) dialkylamino; (j) heteroalkyl; (k) optionally substituted heterocycle; (l) optionally substituted heterocyclylalkyl; (m) optionally substituted heterocyclylalkoxy; (n) alkylsulfonyl; (o) aminosulfonyl, mono-alkylaminosulfonyl or dialkylaminosulfonyl; (p) heteroalkoxy; and (q) carboxy;
R$_6$ is selected from a group consisting of:
(a) hydrogen; (b) halo; (c) alkyl; and (d) alkoxy;
or a pro-drug, individual isomer, mixture of isomers and pharmaceutically acceptable salt thereof.

In certain embodiments, the compound enhancing production of IL-12 is represented by the following structure:

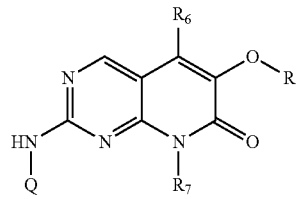

Formula 5 wherein: R is selected from: (a) alkyl optionally-substituted with one to three of R$_{17}$; (b) cycloalkyl optionally substituted with one, two or three groups selected from R$_{18}$; and (c) optionally-substituted aryl; Q is selected from alkyl, cycloalkyl, substituted cycloalkyl, heterocyclyl, substituted heterocyclyl, and alkyl substituted with one, two or three of halogen, cyano, —OR$_8$, —SR$_8$, —C(═O)R$_8$, —C(O)2R$_8$, —C(═O)NR$_8$R$_9$, —S(O)$_p$R$_{10}$, —C(O)$_2$NR$_8$R$_9$, —S(O)$_2$NR$_8$R$_9$, —NR$_8$R$_9$, cycloalkyl, substituted cycloalkyl, heterocyclyl, and/or substituted heterocyclyl;
R$_6$ is hydrogen or lower alkyl; R$_7$ is selected from hydrogen, alkyl, substituted alkyl, halogen, cyano, nitro, hydroxy, alkoxy, haloalkoxy, amino, alkylamino, and optionally-substituted cycloalkyl, heterocyclyl, aryl, or heteroaryl; R$_8$ and R$_9$ are (i) independently selected from hydrogen, alkyl, haloalkyl, hydroxyalkyl, alkoxyalkyl, cycloalkyl, substituted cycloalkyl, heterocyclyl, and substituted heterocyclyl; or (ii) when R$_8$ and R$_9$ are attached to the same nitrogen atom (as in —C(O)$_2$NR$_8$R$_9$, —S(O)$_2$NR$_8$R$_9$, and —NR$_8$R$_9$), R$_8$ and R$_9$ may be taken together to form an optionally-substituted heterocyclyl ring; R$_{10}$ is alkyl, hydroxyalkyl, alkoxyalkyl, cycloalkyl, substituted cycloalkyl, heterocyclyl, or substituted heterocyclyl; R$_{17}$ is at each occurrence independently selected from halogen, haloalkoxy, haloalkyl, alkoxy, or optionally-substituted phenyl, benzyl, phenyloxy, benzyloxy, or cycloalkyl; R$_{18}$ is at each occurrence independently selected from alkyl, substituted alkyl, halogen, haloalkyl, haloalkoxy, cyano, alkoxy, acyl, alkoxycarbonyl, alkylsulfonyl, or optionally-substituted phenyl, phenyloxy, benzyloxy, cycloalkyl, heterocyclyl, or heteroaryl; and p is 1 or 2;
or a pharmaceutically acceptable salt thereof.

In certain embodiments, the compound enhancing production of IL-12 is the compound with the generic name Pamapimod; in other embodiments, the compound enhancing production of IL-12 is the compound with the generic name RO3201195.

In certain embodiments where one or both of the compounds are p38 kinase inhibitors, one or both of the p38 kinase inhibitors are covalently bound to a macrolide as represented in Formula 6:

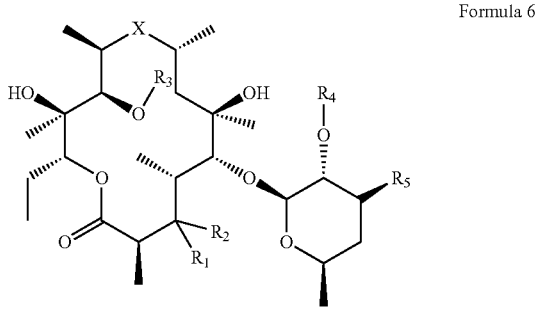

Formula 6

Wherein
$R_1$=H and $R_2$=OH or O-cladinosyl or
$R_1$, $R_2$=(=O);
X=(C=O) or (C=N—OH) or —[N(CH$_3$)—CH$_2$]— or —[CH$_2$—N(CH$_3$)]—;
$R_3$, $R_4$=H or binding site;
$R_5$=R6-(NCH$_3$) or binding site;
R6=CH$_3$ or binding site;
Wherein a p38 kinase inhibitory moiety (such as a molecule as defined in formulas 1, 2, 3, 4, 5, 7, 8, or 9) is covalently bound to the moiety of Formula 6 at any binding site such that the macrolide, an optional spacer, and a functional complex in a linear arrangement are representing $R_1$, $R_2$, $R_3$, $R_4$, or $R_5$ in formula 1 or $R_1$ or $R_2$ in formula 2 or $R_1$ in formula 3 or $R_1$, $R_2$, $R_3$, $R_4$, $R_5$, or $R_6$ in formula 4 or R, $R_6$, $R_7$ or Q in formula 5 or $R_1$, $R_2$, $R_3$, $R_4$, or $R_5$ in formula 7 or $R_1$, $R_2$, $R_3$, $R_4$, or $R_5$ in formula 8 or $R_1$, $R_2$, $R_3$, $R_4$, or $R_5$ in formula 9; or a pharmaceutically acceptable salt thereof.

In certain embodiments, the spacer, if applicable, comprises a chain of maximal 10 carbon and oxygen atoms, being hydrolysable or not hydrolysable under physiological conditions, for separating the macrolide ring shown in Formula 6 from the rest of the molecule.

A functional complex, if applicable, is any arrangement of atoms as defined in the respective definitions.

In certain embodiments, the macrolide is an azalide.

As shown in FIG. 8, a nucleophile is a kinase inhibitor or its chemical precursor with a reactive site, e.g., SH, OH, COOH, NH or analogous. A linker may be present or absent. If present, it may be any suitable element, that combines the macrolide and the nucleophile by covalent bonds. It may be cleavable under physiological conditions to release a molecule with p38-inhibitory activity or not. It can be represented by, but is not limited to the following structures. In certain embodiments, the linkage structure is a thiol; in certain embodiments, the nucleophile is a p38 kinase inhibitor.

In certain embodiments wherein one or both of the compounds is covalently bound to a macrolide as represented in Formula 6, the compound is administered together with a compound of Formula 3.

In another aspect, the invention provides a method of treating a cancer by providing a compound covalently bound to a macrolide as represented in Formula 6 in combination with the compound of Formula 4.

In another aspect, the invention provides a method of treating a cancer by providing a compound covalently bound to a macrolide as represented in Formula 6 in combination with the compound of Formula 5.

In another aspect, the invention provides a method of treating a cancer by providing a compound covalently bound to a macrolide as represented in Formula 6 in combination with the compound with the generic name Pamapimod or a pharmaceutically acceptable salt thereof.

In another aspect, the invention provides a method of treating a cancer by providing a compound covalently bound to a macrolide as represented in Formula 6 in combination with the compound with the generic name RO3201195.

In certain embodiments wherein one or both of the compounds are inhibitors of p38 kinase, at least one compound is represented by the following structure:

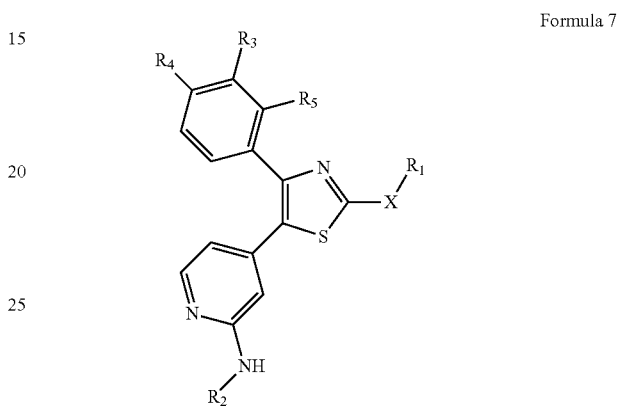

Formula 7 wherein, x=CH$_2$, O, S, S(=O), S(=O)$_2$, $R_1$=2-hydroxypropyl, 3-hydroxypropyl, 2-hydroxyethyl, 2,3-dihydroxypropyl, 2-hydroxy-3-aminopropyl, 2-hydroxy-3-aminobutyl, 3,4-dihydroxybutyl, 2,3,4-trihydroxybutyl, —(CH$_2$)$_n$—COR with R=OH, O-alkyl (C$_1$-C$_4$), O-alkylaryl, NH$_2$, NHMe, NHOH, and n=1, 2, 3, 4, 5, —CH$_2$—P=O(OR)$_2$ with R=H, CH$_3$, CH$_2$CH$_3$, —CH$_2$—(CH$_2$)$_m$—S(=O)$_n$—R with R=alkyl (C$_1$-C$_5$), OH, NH$_2$, and m=1, 2, 3 and n=0, 1, 2, glycidyl, 3-methylglycidyl, —CH$_2$—CHOH—COR with R=OH, OMe, OEt, NH2, NHOH, —CH(CH$_2$OH)—COR with R=OH, OMe, OEt, NH2, NHOH, —CH$_2$—CHOH—CN, —CH(CH$_2$OH)—CN, methyl, ethyl, 1-propyl, 2-propyl, phenyl, benzyl, $R_2$=hydrogen, alkyl, aryl, or arylalkyl with 1-10 carbon atoms, acyl with 1-11 carbon atoms, $R_3$=H, halogen, CH$_3$, CF$_3$, OCF$_3$, $R_4$=H, halogen, CH$_3$, CF$_3$, OCF$_3$, $R_5$=H, halogen, CF$_3$; or a pharmaceutically acceptable salt thereof.

In certain embodiments, the compound inhibiting IL-10 is represented by the following structure:

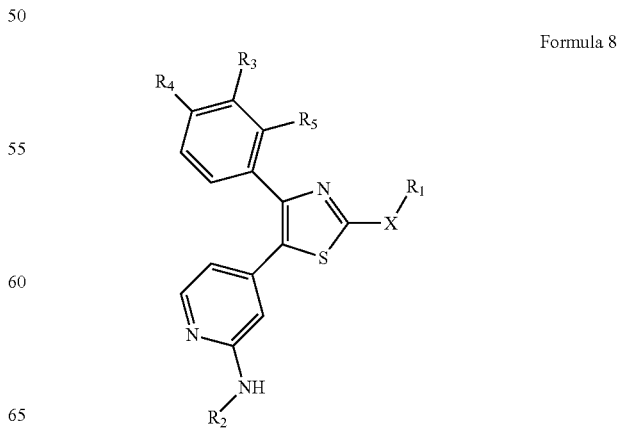

Formula 8 wherein x=CH₂, S, S(=O), S(=O)₂ R₁=2-hydroxypropyl, 3-hydroxypropyl, 2-hydroxyethyl, 2,3-dihydroxypropyl, 2-hydroxy-3-aminopropyl, 2-hydroxy-3-aminobutyl, 3,4-dihydroxybutyl, 2,3,4-trihydroxybutyl, glycidyl, 3-methylglycidyl, methyl, ethyl, 1-propyl, 2-propyl, R₂=hydrogen, alkyl, aryl, or arylalkyl with 1-10 carbon atoms, acyl with 1-11 carbon atoms, R₃=H, halogen, CH₃, CF₃, OCF₃, R₄=H, halogen, CH₃, CF₃, OCF₃, R₅=H, halogen, CF₃; or a pharmaceutically acceptable salt thereof.

In certain embodiments, the compound inhibiting IL-10 is represented by the following structure:

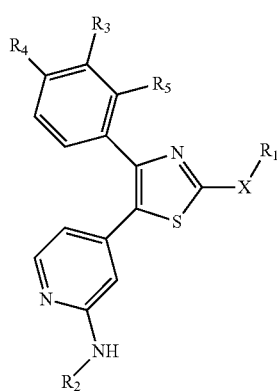

Formula 9 wherein x=CH₂ R₁=methyl R₂=benzoyl R₃=CH₃ R₄=HR₅=H; or a pharmaceutically acceptable salt thereof.

In another aspect, the invention provides a pharmaceutical composition for treating cancer in a subject in need thereof, the pharmaceutical composition comprising one or more compounds to enhance IL-12 production or inhibit IL-10 production, together with a pharmaceutically acceptable carrier. In certain embodiments, at least one compound is a compound to enhance IL-12 production. In certain embodiments, at least one compound is a compound to inhibit IL-10 production. In certain embodiments, a first compound is a compound to inhibit IL-10 production and a second compound is a compound to inhibit IL-10 production.

In certain embodiments, the composition contains conjugates, pro-drugs and active metabolites of the compounds. In certain embodiments, the pharmaceutical composition further comprises an excipient, such as lactose, powdered sucrose, dextrose, mannitol, cellulose polymers (such as cellulose acetate phthalate, hydroxypropyl cellulose, hydroxypropyl methylcellulose, hydroxypropyl methylcellulose phthalate, and hydroxypropyl methylcellulose acetate succinate), polyvinyl acetate phthalate, acrylic acid polymers and copolymers, and methacrylic resins, zein, shellac, and polysaccharides; an additive such as dispersing or wetting agents, suspending agents, and preservatives, binders, fillers, lubricants, disintegrants, diluents, surfactants, stabilizers, preservatives, flavoring and coloring agents, silicon dioxide, titanium dioxide, alumina, talc, kaolin, powdered cellulose, and microcrystalline cellulose, as well as soluble materials, such as mannitol, urea, sucrose, lactose, dextrose, sodium chloride, sorbitol, vegetable oils, glycerin, magnesium stearate, calcium stearate, stearic acid, starches, clays, celluloses, algins, gums, crosslinked polymers, dicalcium phosphate, calcium sulfate, lactose, cellulose, kaolin, mannitol, sodium chloride, dry starch, and powdered sugar, surfactants (anionic, cationic, amphoteric, or nonionic surface active agents), aqueous and non-aqueous sterile injection solutions, anti-oxidants, buffers, bacteriostats, or thickening agents.

In certain embodiments, the pharmaceutical composition comprises a short-term, rapid-onset, rapid-offset, controlled release, sustained release, delayed release, or pulsatile release composition, providing the compositions achieve administration of a compound.

In certain embodiments, the pharmaceutical composition is suitable for various modes of delivery, including, but not limited to oral, parenteral (including intravenous, intramuscular, subcutaneous, intradermal, intrathecal, intra-arterial, intracardiac, subcutaneous and transdermal), topical (including dermal, buccal, and sublingual, vaginal, urethral, and rectal administration), nasal spray, surgical implant, internal surgical paint, infusion pump, or other delivery device.

In certain embodiments of the pharmaceutical composition, the active agent can be delivered via a medical device, including, but not limited to Intratumoural sponges.

In certain embodiments of the methods of the invention, the cancer is selected from the group consisting of breast cancer, pancreas cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteosarcoma, chondrosarcoma, Ewing's sarcoma, malignant fibrous histiocytoma, fibrosarcoma, multiple myeloma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, glioblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas. In certain embodiments of the methods of the invention, cancers treatable according to the invention include cancers of the breast, pancreas, skin, prostate, liver, lung, lymphoid system, bladder, kidney, brain, colon and bone. In certain embodiments of the methods of the invention, the cancer is selected from the group consisting of melanoma, prostate adenocarcinoma, lymphoma, pancreatic ductal carcinoma, renal carcinoma, hepatocellular carcinoma, small cell lung carcinoma, non-small cell lung carcinoma, urothelial cell carcinoma, colon carcinoma, glioblastoma, breast lobular or ductal carcinoma, osteosarcoma, chondrosarcoma, and multiple myeloma.

In another aspect, the invention provides a method of treating cancer, neoplasm, growth or tumour in a human in need of treatment, comprising the step of administering to the human a compound according to Formula 1 or a pharmaceutically acceptable salt thereof in a therapeutically effective dose to treat said cancer, neoplasm, growth or tumour.

In another aspect, the invention provides a method of treating cancer, neoplasm, growth or tumour in a human in need of treatment, comprising the step of administering to the human the compound according to Formula 2 or a pharmaceutically acceptable salt thereof in a therapeutically effective dose to treat said cancer, neoplasm, growth or tumour.

In another aspect, the invention provides a method of treating cancer, neoplasm, growth or tumour in a human in need of treatment, comprising the step of administering to the human the compound according to Formula 3 or a pharmaceutically acceptable salt thereof in a therapeutically effective dose to treat said cancer, neoplasm, growth or tumour.

In another aspect, the invention provides a method of treating cancer, neoplasm, growth or tumour in a human in need of treatment, comprising the step of administering to the human the compound according to Formula 4 or a pharmaceutically acceptable salt thereof in a therapeutically effective dose to treat said cancer, neoplasm, growth or tumour. In certain embodiments, the compound is the compound with the generic name RO3201195; in certain embodiments, the compound is the R isomer of RO3201195.

In another aspect, the invention provides a method of treating cancer, neoplasm, growth or tumour in a human in need of treatment, comprising the step of administering to the human the compound according to Formula 5 or a pharmaceutically acceptable salt thereof in a therapeutically effective dose to treat said cancer, neoplasm, growth or tumour. In certain embodiments, the compound is Pamapimod.

In another aspect, the invention provides a method of treating cancer, neoplasm, growth or tumour in a human in need of treatment, comprising the step of administering to the human the compound according to Formula 6 or a pharmaceutically acceptable salt thereof in a therapeutically effective dose to treat said cancer, neoplasm, growth or tumour.

In another aspect, the invention provides a method of treating cancer, neoplasm, growth or tumour in a human in need of treatment, comprising the step of administering to the human the compound according to Formula 7 or a pharmaceutically acceptable salt thereof in a therapeutically effective dose to treat said cancer, neoplasm, growth or tumour.

In another aspect, the invention provides a method of treating cancer, neoplasm, growth or tumour in a human in need of treatment, comprising the step of administering to the human the compound according Formula 8 or a pharmaceutically acceptable salt thereof in a therapeutically effective dose to treat said cancer, neoplasm, growth or tumour.

In another aspect, the invention provides a method of treating cancer, neoplasm, growth or tumour in a human in need of treatment, comprising the step of administering to the human the compound according Formula 9 or a pharmaceutically acceptable salt thereof in a therapeutically effective dose to treat said cancer, neoplasm, growth or tumour. In certain embodiments, the compound is TAK-715.

In certain embodiments of any of the methods of treatment (or uses) of the invention, the method further comprises the step of administering to the subject cytotoxic chemotherapy, cytostatic chemotherapy, radiotherapy, photodynamic therapy, or surgery. In certain embodiments, the compound is TAK-715.

In another aspect, the invention provides a method for enhancing a vaccination response in a patient in need of same using the compound of Formula 4 or a pharmaceutically acceptable salt thereof.

In another aspect, the invention provides a method for enhancing a vaccination response in a patient in need of same using the compound of Formula 5 or a pharmaceutically acceptable salt thereof.

In another aspect, the invention provides a method for enhancing a vaccination response in a patient in need of same using the compound of Formula 1 or a pharmaceutically acceptable salt thereof.

In another aspect, the invention provides a method for enhancing a vaccination response in a patient in need of same using the compound of Formula 7 or a pharmaceutically acceptable salt thereof.

In another aspect, the invention provides a method for enhancing a vaccination response in a patient in need of same using the compound of Formula 6 or a pharmaceutically acceptable salt thereof.

In another aspect, the invention provides a compound disclosed herein for the treatment of cancer, or a pharmaceutically acceptable salt thereof.

In certain embodiments of any of the methods of treatment (or uses) of the invention, the treatment is combined with the administration of a recombinant cytokine. In certain embodiments, the cytokine is tumour necrosis factor alpha or interferon gamma.

In another aspect, the invention provides a compound represented by any of the structures of Formula 10:

Formula 10

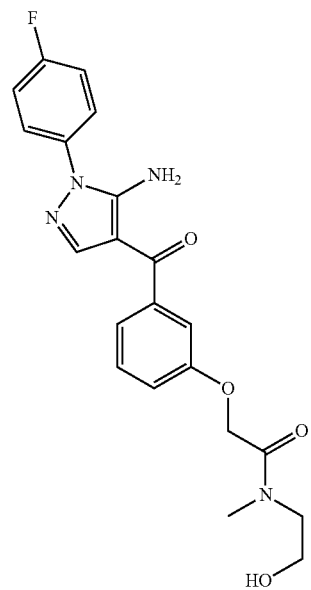

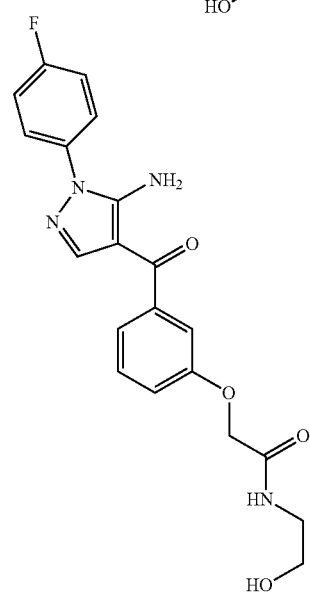

-continued

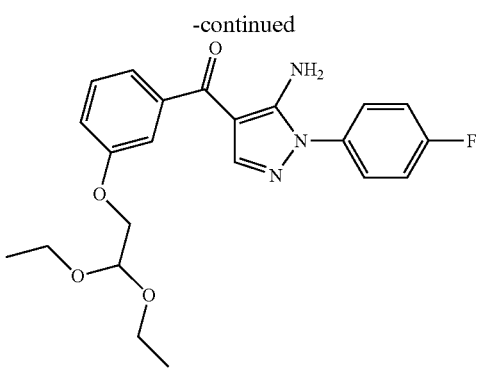

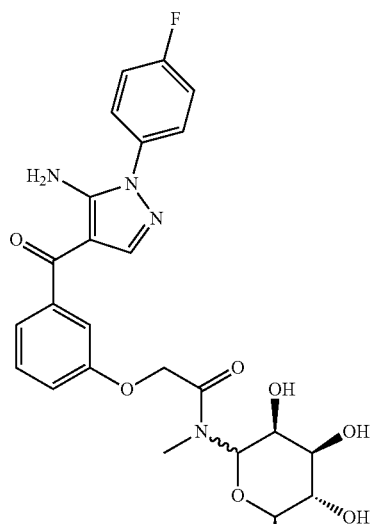

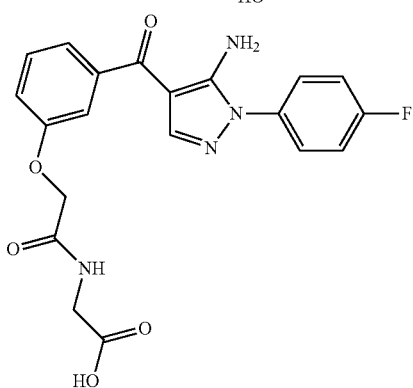

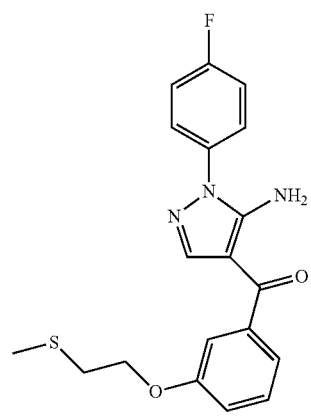

-continued or a pharmaceutically acceptable salt thereof.

In yet another aspect, the invention provides a p38 kinase inhibitor covalently bound to a macrolide as represented in Formula 6:

Formula 6

Wherein
$R_1$=H and $R_2$=OH or O-cladinosyl or
$R_1$, $R_2$=(=O);
X=(C=O) or (C=N—OH) or —[N(CH$_3$)—CH$_2$]— or —[CH$_2$—N(CH$_3$)]—;
$R_3$, $R_4$=H or binding site;
$R_5$=R6-(NCH$_3$) or binding site;
R6=CH$_3$ or binding site;
wherein a p38 kinase inhibitory moiety (such as a molecule as defined in formulas 1, 2, 3, 4, 5, 7, 8, or 9) is covalently bound to the moiety of Formula 6 at any binding site such that the macrolide, an optional spacer, and a functional complex in a linear arrangement are representing $R_1$, $R_2$, $R_3$, $R_4$, or $R_5$ in formula 1 or $R_1$ or $R_2$ in formula 2 or $R_1$ in formula 3 or $R_1$, $R_2$, $R_3$, $R_4$, $R_5$, or $R_6$ in formula 4 or R, $R_6$, $R_7$ or Q in formula 5 or $R_1$, $R_2$, $R_3$, $R_4$, or $R_5$ in formula 7 or $R_1$, $R_2$, $R_3$, $R_4$, or $R_5$ in formula 8 or $R_1$, $R_2$, $R_3$, $R_4$, or $R_5$ in formula 9; or a pharmaceutically acceptable salt thereof.

In certain embodiments, the spacer, if applicable, comprises a chain of maximal 10 carbon and oxygen atoms, being hydrolysable or not hydrolysable under physiological conditions, for separating the macrolide ring shown in Formula 6 from the rest of the molecule.

A functional complex, if applicable, is any arrangement of atoms as defined in the respective definitions.

In certain embodiments, the macrolide is an azalide. In certain embodiments, the linkage structure is a thiol; in certain embodiments, the nucleophile is a p38 kinase inhibitor.

In still another aspect, the invention provides any novel compound described herein, or a pharmaceutically acceptable salt thereof.

In yet another aspect, the invention provides the use of any compound disclosed herein for the preparation of a medicament for the treatment of cancer.

BRIEF DESCRIPTION OF DRAWINGS

In FIG. 7, a nucleophile is a kinase inhibitor or its chemical precursor with a reactive site, e.g. S—H, OH, COOH, NH or analogous. A linker may be present or absent. If present, it may be any suitable element, that combines the macrolide and the nucleophile by covalent bonds. It may be cleavable under physiological conditions to release a molecule with p38-inhibitory activity or not. It can be represented by, but is not limited to the structures shown in FIG. 7.

DETAILED DESCRIPTION OF THE INVENTION

Figure 1:
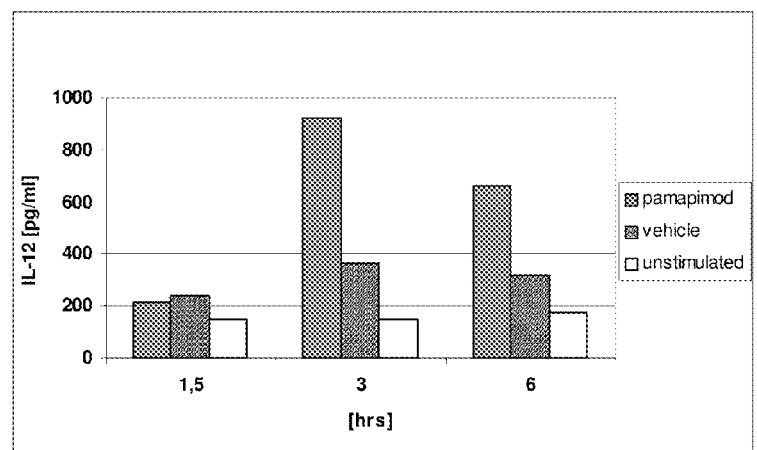
FIG. 1 IL-12 Production by hTNFα treated mice. Data are the average concentration of IL-12 in the plasma of mice that were treated with pamapimod prior to stimulation with hTNFα (grey bars), or the vehicle (2% citric acid, hatched bars), or not stimulated at all (white bars); (n=4).

Treatments for cancer are commonly cytotoxic and are assisted to variable extents by immune responses to the tumour either directly (antibodies to tumour antigens) or indirectly (immune responses to non-viable tumour tissue). Despite variable degrees of immune activation by conventional therapies, the addition of immune therapy via therapeutic vaccination with tumour antigens or general immune stimulation using stimulants of bacterial sensing systems have not lead to generally successful therapeutic approaches. One reason for this is the immune privileged zone around a tumour. A problem to solve, therefore, is to develop a means to prevent the local immune suppression around a tumour so that immune responses to a tumour can assist other forms of therapy. Clearly, any agent that simply promoted immune reactions would be undesirable if it resulted in immune responses to healthy tissue, or a general feeling of ill-health such as one may experience with interferon therapy.

The compounds according to the present invention are selected for their ability to suppress synthesis of IL-10 local to a tumour and/or to increase local expression of IL-12. A particularly surprising result was that by combining stimulation with TNFalpha and treatment with one such compound, there was an enhancement in IL-12 production, despite the fact that such compounds are thought to be intrinsically anti-inflammatory. Indeed this compound class had been proposed as one to be used to reduce TNFα concentrations. Our data suggest, in contrast, that it is most useful in converting TNFα stimulus to an anti-cancer reaction but simultaneously suppressing IL-10 and enhancing production of IL-12. By this means, the main immune suppressive functions near are tumour are counteracted and the strength of immune suppression is reduced. The ability to reverse the normal immune suppressive effect of a tumour is dictated in part by the exposure of the substance to the tumour microenvironment and in part by exposure to peripheral immune cells that then enter the tumour. The substances should, therefore, be formulated and administered so that adequate exposure is obtained.

Advantageous Effects of Invention

The compounds reported here are useful in many respects. In preferred embodiments, they are able to intensify the effects of common anti-tumour therapy and they are not cytotoxic, thus making them more easily tolerated than other forms of therapy. They also exert a form of immune regulation that is dependant on signals in the tumour environment. Thus, IL-12 is only released in the presence of TNFa which is produced near tumours as part of the normal tumour response.

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. The present invention is directed to combinations of compounds, pharmaceutical compositions providing the combinations, and methods of using the compounds, combinations and compositions for treating cancer and inflammatory diseases. In certain embodiments, the combinations comprise p38 MAPK inhibiting compounds that may influence more than one signaling pathway including that of NF-kB.

DEFINITIONS

The term "compound" as used herein means a chemical entity, whether in a crude mixture or purified and isolated. "P38" shall mean the protein commonly known as p38 mapkinase, p38 MAPK or any of its isoforms, splice variants. The term "p38 inhibiting compound" or "p38 inhibitor" as used herein means any compound that inhibits activity of p38 MAPK either directly or indirectly wherein p38 activity is measured using ATF2 phosphorylation in the presence of 100 mM ATP, and wherein, an inhibitor is considered to reduce this phosphorylation by 50% or more at an inhibitor concentration of 20 μM or less.

The term "IL-10 inhibitor" or "IL-10 synthesis inhibitor" means a compound that inhibits the production of IL-10 by more than 20% relative to untreated cells using the methods described in Example 52 at a compound concentration in medium of 2 μM. (murine peritoneal macrophage, or spleen cells following stimulation by lipopolysaccharide or TNFalpha or IL-1 or a tumour conditioned medium in the presence of the compound).

The term "IL-12 stimulator" or "IL-12 synthesis stimulator" or "IL-12 synthesis enhancer" means a compound that stimulates the production, expression or activity of IL-12 by murine tumours in vivo by more than 20% relative to those from vehicle treated mice (i.e. 120% of vehicle or more) after treatment with the substance at a dose of 10 µmol/kg/d i.p. for 10 or more days according to the conditions of example 54; or a compound that stimulates the production or expression of IL-12 as detected in plasma by more than 20% relative to those from vehicle treated mice (i.e. 120% of vehicle or more) at 3 h after treatment with the substance at a dose of 10 µmol/kg/d i.p. under the conditions described in example 53 herein.

The term "IL-12 inhibitor" or "IL-12 synthesis inhibitor" means a compound that inhibits the production of IL-12 by murine peritoneal macrophage, or spleen cells or in vivo following stimulation by lipopolysaccharide or TNFalpha or IL-1 or a tumour conditioned medium in the presence of the compound by more than 20% at 1 µM relative to a vehicle treated cells.

The term "tumour conditioned medium" means medium recovered after growth of tumour cells in that medium. The term "TNF" shall mean any member of the Tumour necrosis factor super family. The term "TNFa" shall mean Tumour Necrosis Factor alpha from any applicable species including murine and human forms.

The term "alkyl" as used herein means saturated straight, branched, or cyclic hydrocarbon groups. In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), or 1 to 4 carbon atoms ("C1-4 alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. Substituted alkyl refers to alkyl substituted with one or more non-interfering substituents, such as but not limited to halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryl; aryloxy; nitro; cycloalkyl; acetylene; alkanoyloxy; ketone; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 1 to 10 carbon atoms ("C1-10 alkenyl"). In further embodiments, alkyl refers to groups comprising 1 to 8 carbon atoms ("C1-8 alkenyl"), 1 to 6 carbon atoms ("C1-6 alkenyl"), or 1 to 4 carbon atoms ("C1-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 1 to 10 carbon atoms ("C1-10 alkynyl"). In further embodiments, alkyl refers to groups comprising 1 to 8 carbon atoms ("C1-8 alkynyl"), 1 to 6 carbon atoms ("C1-6 alkynyl"), or 1 to 4 carbon atoms ("C1-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl or -alkyl-O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), or 1 to 4 carbon atoms ("C1-4 alkoxy"). The term "halo" or "halogen" as used herein means fluorine, chlorine, bromine, or iodine.

The term "heterocycle" or "heterocyclic" as used herein means one or more rings of 5, 6 or 7 atoms with or without unsaturation or aromatic character and having at least one ring atom which is not carbon. Preferred heteroatoms include sulfur, oxygen, and nitrogen. Multiple rings may be fused, as in quinoline or benzofuran. "Substituted heterocycle" is heterocycle having one or more side chains formed from non-interfering substituents.

The term "aryl" as used herein means a stable monocyclic, bicyclic, or tricyclic carbon ring of up to 8 members in each ring, wherein at least one ring is aromatic as defined by the Huckel 4n+2 rule. Multiple aryl rings may be fused, and aryl rings may be fused or unfused with one or more cyclic hydrocarbon, heteroaryl, or heterocyclic rings. Exemplary aryl groups according to the invention include phenyl, naphthyl, tetrahydronaphthyl, and biphenyl. The aryl group can be substituted with one or more non-interfering substituents, such as, for example, hydroxyl, amino, alkylamino, arylamino, alkoxy, aryloxy, nitro, cyano, sulfonic acid, sulfate, phosphonic acid, phosphate, or phosphonate.

The term "heteroaryl" as used herein means an aryl group containing from one or more (particularly one to four) non-carbon atom(s) (particularly N, O, or S) or a combination thereof, which heteroaryl group is optionally substituted at one or more carbon or nitrogen atom(s) with alkyl, —$CF_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1, 2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms. Substituted heteroaryl is heteroaryl having one or more non-interfering groups as substituents.

The terms "aralkyl" and "arylalkyl" as used herein mean an aryl group as defined above linked to the molecule through an alkyl group as defined above.

The terms "alkaryl" and "alkylaryl" as used herein means an alkyl group as defined above linked to the molecule through an aryl group as defined above.

The term "acyl" as used herein means a carboxylic acid ester in which the non-carbonyl moiety of the ester group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with one or more non-interfering substituents, such as halogen, C1-C6 alkyl or C1-Ce alkoxy; sulfonate esters such as alkyl or aralkyl sulphonyl including methanesulfonyl; mono-, di-, or triphosphate ester; trityl or monomethoxytrityl; substituted benzyl; trialkylsilyl such as dimethyl-t-butylsilyl or diphenylmethylsilyl. Aryl groups in the esters optimally comprise a phenyl group.

The term "amino" as used herein means a moiety represented by the structure NR2, and includes primary amines, and secondary and tertiary amines substituted by alkyl (i.e., alkylamino). Thus, R2 may represent two hydrogen atoms, two alkyl moieties, or one hydrogen atom and one alkyl moiety.

The terms "alkylamino" and "arylamino" as used herein mean an amino group that has one or two alkyl or aryl substituents, respectively.

The term "macrolide" refers to any macrocyclic lactone with 10 or more members.

Reference to an atom includes all isotopes of that atom. For example, structures drawn with carbon or hydrogen include isotopes such as $^{13}C$ or $^{2}H$.

The term "non-interfering substituents" as used herein means any groups that yield stable compounds. Suitable non-interfering substituents or radicals include, but are not limited to, halo, C1-C10 alkyl, C2-C10 alkenyl, C2-C10 alkynyl, C1-C10 alkoxy, C7-C12 aralkyl, C7-C12 alkaryl, C3-C10 cycloalkyl, C3-C10 cycloalkenyl, phenyl, substituted phenyl, toluoyl, xylenyl, biphenyl, C2-C12 alkoxyalkyl, C7-C12 alkoxyaryl, C7-C12 aryloxyalkyl, CO—C12 oxyaryl, C1-Ce alkylsulfinyl, C1-C10 alkylsulfonyl, —(CH2)D1-O—(C1-C10 alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C1-C10 alkyl), —C(O)—(C1-C10 alkyl), C2-C10 thioalkyl, —C(O)O— (C1-C10 alkyl), —OH, —SO$_2$, =S, —COOH, —NR$_2$, carbonyl, —C(O)—(C1-C10 alkyl)-CF$_3$, —C(O)—CF$_3$, —C(O)NR$_2$, —(C1-C10 alkyl)-S—(C6-C12 aryl), —C(O)—(C6-C12 aryl), —(CH$_2$)$_m$—O—(CH$_2$)$_m$—O—(C1-C10 alkyl), wherein each m is from 1 to 8, —C(O)NR$_2$, —C(S)NR$_2$, —SO$_2$NR$_2$, —NRC(O)NR$_2$, —NRC(S)NR$_2$, salts thereof, and the like. Each R as used herein is H, alkyl or substituted alkyl, aryl or substituted aryl, aralkyl, or alkaryl.

The term "analogue" or "analog" as used herein means a compound in which one or more individual atoms or functional groups have been replaced, either with a different atom or a different functional, generally giving rise to a compound with similar properties. The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention. The term "active metabolite" as used herein means a physiologically active compound that results from the metabolism of a compound of the invention, or a prodrug thereof, when such compound or prodrug is administered to a mammal.

The term "intermittent administration" as used herein means administration of a therapeutically effective dose of a composition according to the invention, followed by a time period of discontinuance, which is then followed by another administration of a therapeutically effective dose, and so forth.

"Pharmaceutically acceptable excipient" or "pharmaceutically acceptable carrier" refers to an excipient that can be included in the compositions of the invention and that causes no significant adverse toxicological effects to the patient. "Pharmacologically effective amount," "physiologically effective amount," "therapeutically effective amount", and "therapeutically effective dose" are used interchangeably herein to mean the amount of a conjugate of the invention present in a pharmaceutical preparation that is needed to provide a desired level of active agent and/or conjugate in the bloodstream or in the target tissue. The precise amount will depend upon numerous factors, e.g., the particular active agent, the components and physical characteristics of the pharmaceutical preparation, intended patient population, patient considerations, and the like, and can readily be determined by one skilled in the art, based upon the information provided herein and available in the relevant literature. The term "antiproliferative agent" or "cytostatic" or "cytotoxic" as used herein means a compound that decreases the hyperproliferation of cells. The term "abnormal cell proliferation" as used herein means a disease or condition characterized by the inappropriate growth or multiplication of one or more cell types relative to the growth of that cell type or types in an individual not suffering from that disease or condition.

The term "cancer" as used herein means a disease or condition characterized by uncontrolled, abnormal growth of cells, which can spread locally or through the bloodstream and lymphatic system to other parts of the body. The term includes both tumor-forming or non-tumor forming cancers, and includes various types of cancers, such as primary tumors and tumor metastasis. The term "neoplasm", "growth" or "tumor" as used herein means an abnormal mass of cells within a multicellular organism that results from excessive cell division that is uncontrolled and may be self-limiting or progressive and may be due to an infection or an endogenous process.

It has been discovered according to the present invention that various compounds can be used alone or combined to provide an effect useful in the treatment of cancer. The effect appears to be related to the ability of the compounds to either inhibit synthesis of IL-10 by immune cells (see Example 52) in or around a cancer, or via the ability of the compounds to stimulate or enhance the synthesis, production or release of IL-12 and/or expression its coding sequences (see Example 59). Reduction in the amount of or expression of IL-10 appears to reduce the local immune suppression associated with a tumour or to reduce the ability of local immune cells to support tumour growth. Stimulation of IL-12, appears to be enchanted in the presence of TNFa and a compound of the type reported here (see Example 53) and appears to provide a stimulus to T-cell response to the tumour/cancer via the local increase in expression of IL-12.

The mechanisms of signaling resulting in expression and synthesis of cytokines is regulated by kinases and inhibitors of kinases may thus disregulate these processes. Phenotypic screening of kinase effects on cytokine production, therefore, provides a means of identifying inhibitors that regulate these processes.

It has particularly been recognized that combinations of compounds from the class of p38 inhibitors can provide improved treatment when combined versus the individual compounds. It appears that this effect is due to the fact that certain p38 inhibitors are potent suppressors of IL-10, whereas others are capable of stimulating production of IL-12. Thus combining these entities results in a dual action that is stimulatory of a T-cell mediated immune response.

P38 is a member of the mitogen-activated protein kinases (MAPK) consisting of p38 MAPK along with the extracellular-regulated kinase (ERK) and the c-jun N-terminal kinase (JNK). Due to the similarity of these enzymes, especially at the active site, inhibitors of one class may have side activities on others. In particular, inhibitors of JNK are often inhibitors of p38 variants and vice versa. p38 has also been implicated in the transcriptional up-regulation of NF-kB, in cancer (Hagemann et al., 2008).

Any compound useful to inhibit activity of p38 MAPK (i.e., a p38 inhibiting compound or p38 inhibitor) may be used in a combination according to the present invention in so far as it may influence the expression or production of IL-10 or IL-12 in the assays described herein.

Here we describe a method of treating disease comprised of administering to a subject in need of same, a therapeutically effective dose of a substance that inhibits the synthesis of IL-10 or stimulates IL-12 production, or does both of these things. In another embodiment, the inhibition of IL-10 and the stimulation of IL-12 are provided by different compounds.

In a preferred embodiment, the disease is cancer or a tumour growth or neoplasm.

In a preferred embodiment, the compounds that stimulate IL-12 are selected from those described in Formula 4 and Formula 5. In a more preferred embodiment, the compounds are those known as pamapimod and Compound 49 herein. In a still more preferred embodiment, the compound is the R-isomer of Compound 49. In a still more preferred embodiment, the substance is used at a dose in the range of 0.1 to 30 mmol/kg. In a still more preferred embodiment, the substance is used at a dose in the range of 0.3 to 10 µmol/kg. In a still more preferred embodiment, the substance is used at a dose in the range of 1 to 5 µmol/kg.

In a preferred embodiment, the compounds that inhibit production of IL-10 are selected from those described in Formulas 1, 2, 3, 4, 5, 6, 7, 8 and 9. In a further preferred embodiment, the IL-10 inhibitor is selected from those in described in Formulas 1, 2, 3, 4, 5, 6, 7, 8 and 9.

In certain instances, it is advantageous to increase the concentration of an IL-10 inhibiting compound in immune cells. To increase the selective partition of macrophage, we have conjugated certain p38 inhibitors containing linkable functions to macrocyclic carriers of the erythromycin class. In another embodiment, the compounds capable of stimulating IL-12 or inhibiting IL-10 are conjugated to a carrier structure described in FIG. 7 and example 43. In a preferred embodiment macrolides of the azalide class may be used as stable carriers. Linkage may be made via a variety of stable or non-stable linkages including ether, ester and thiol bonds.

Figure 7:
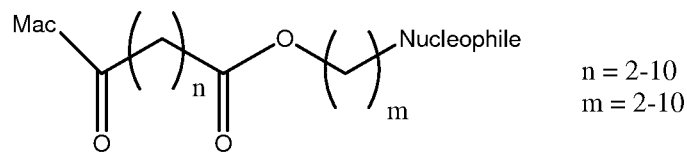
FIG. 7 General scheme for synthesis of a p38 inhibitor conjugated to a macrolide carrier to increase uptake into macrophage.
Figure 7:
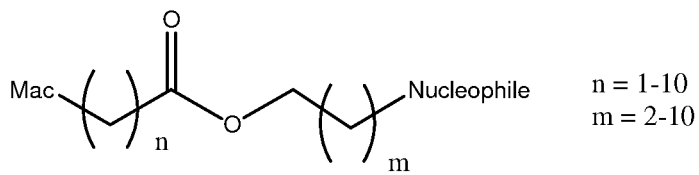
Figure 7:
Figure 7:
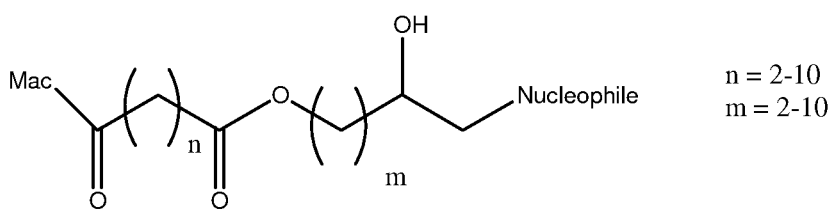
Figure 7:
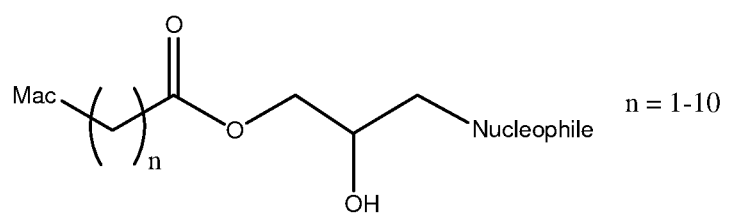
Figure 7:
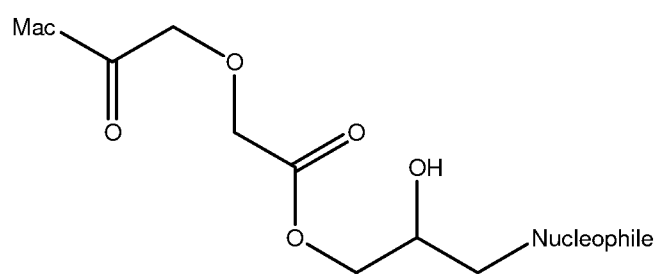
Figure 8:
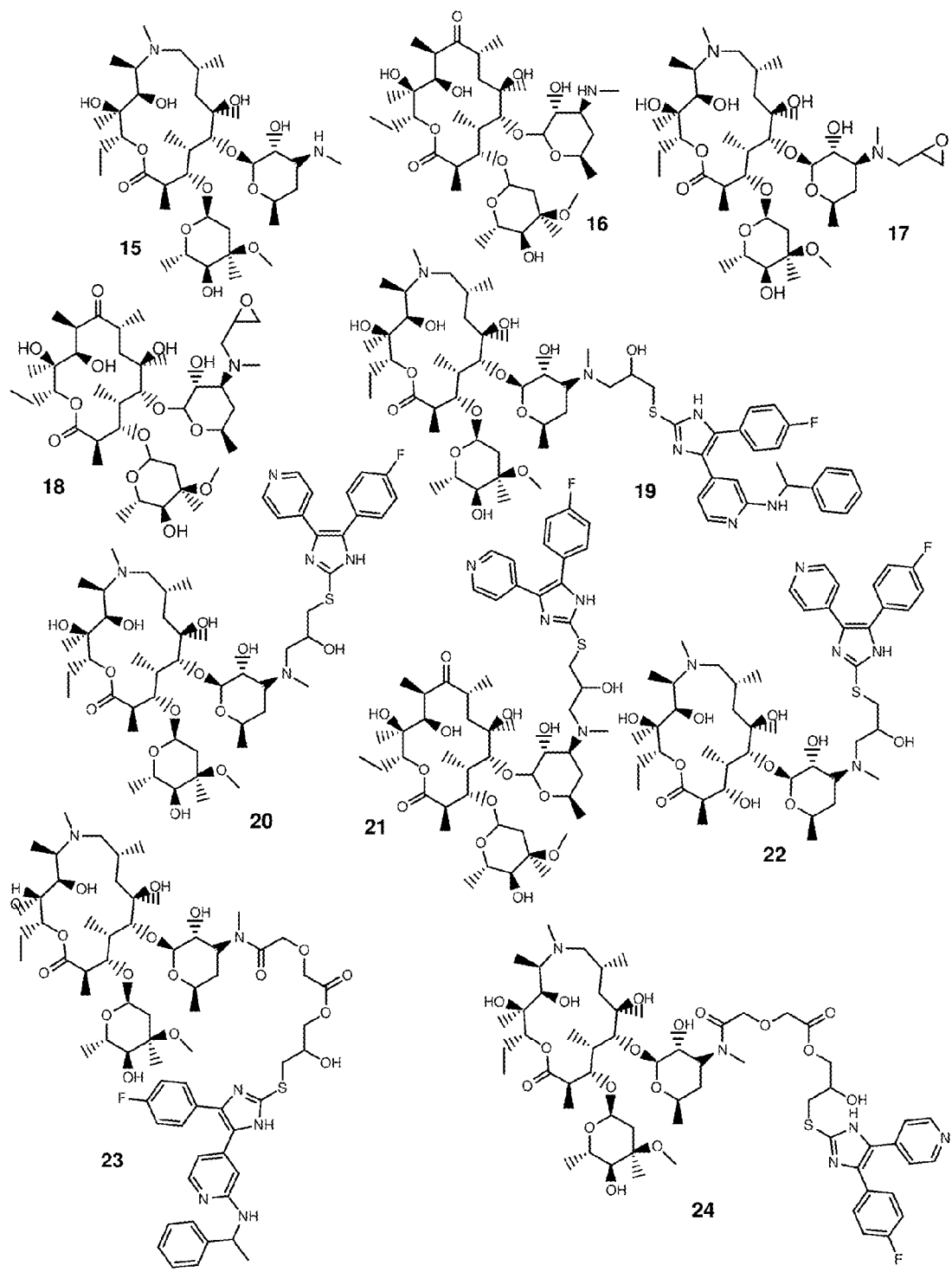
FIG. 8 Example structures of conjugated p38 inhibitors.
Figure 8:
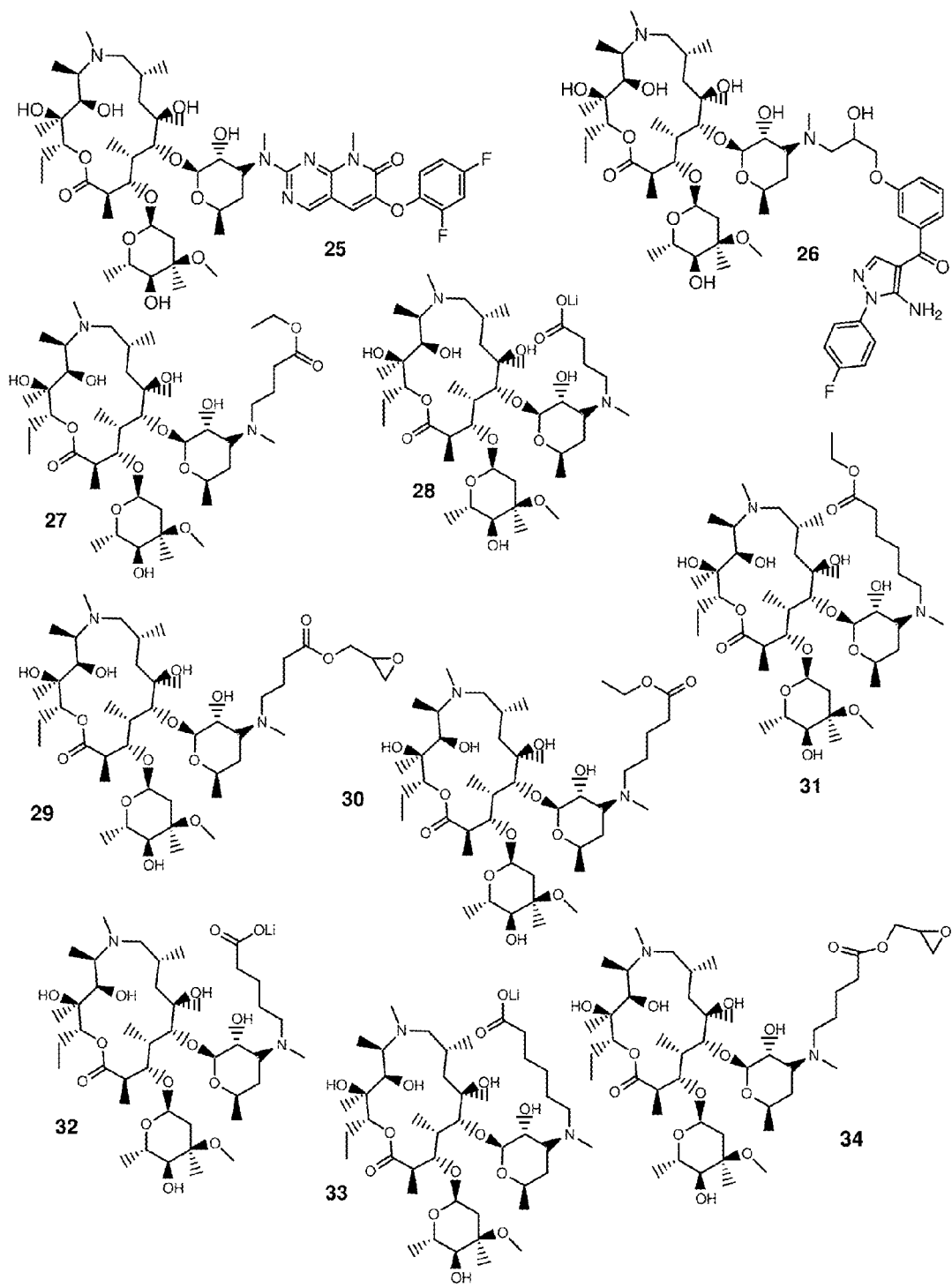
Figure 8:
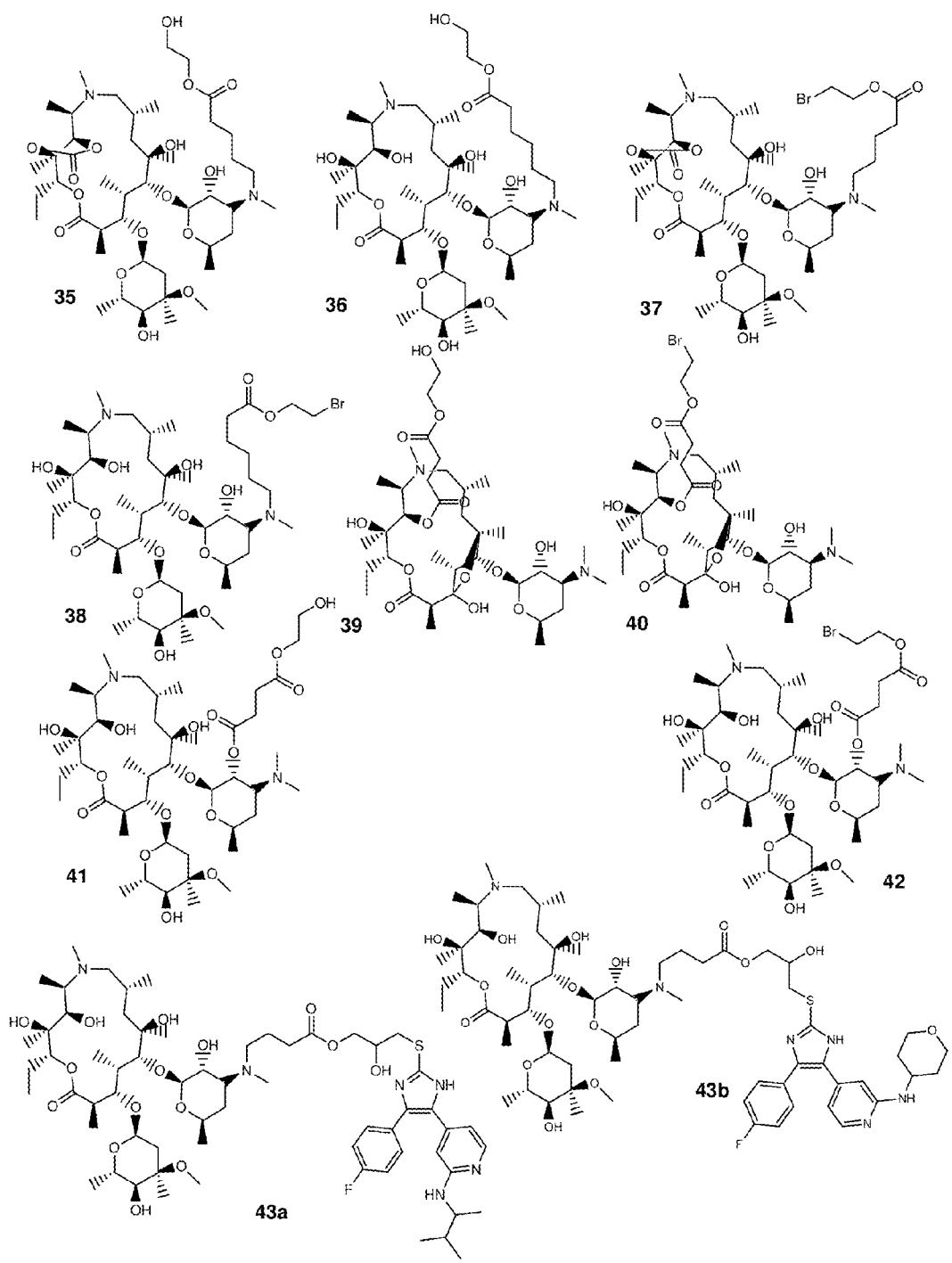
Figure 8:
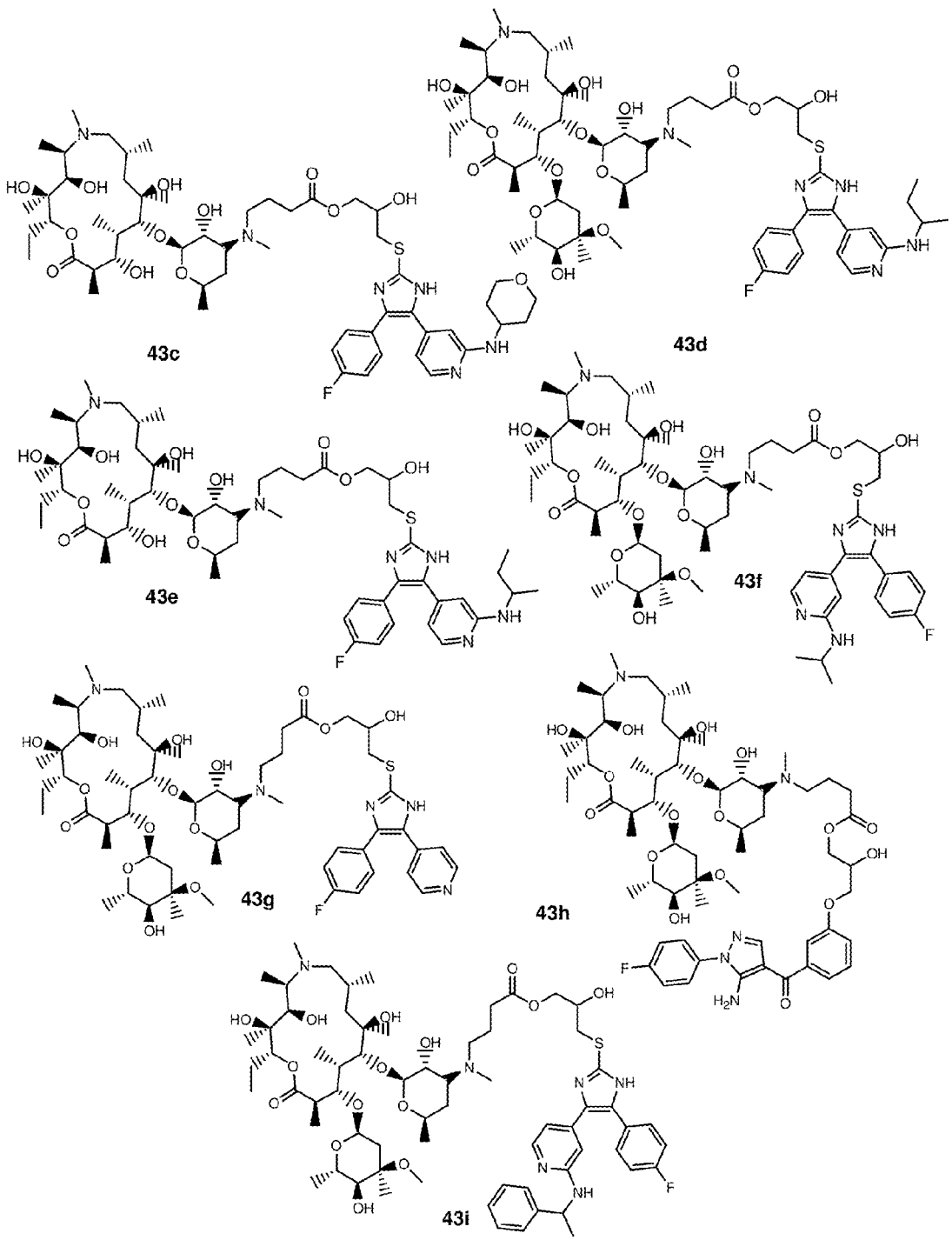
Figure 8:
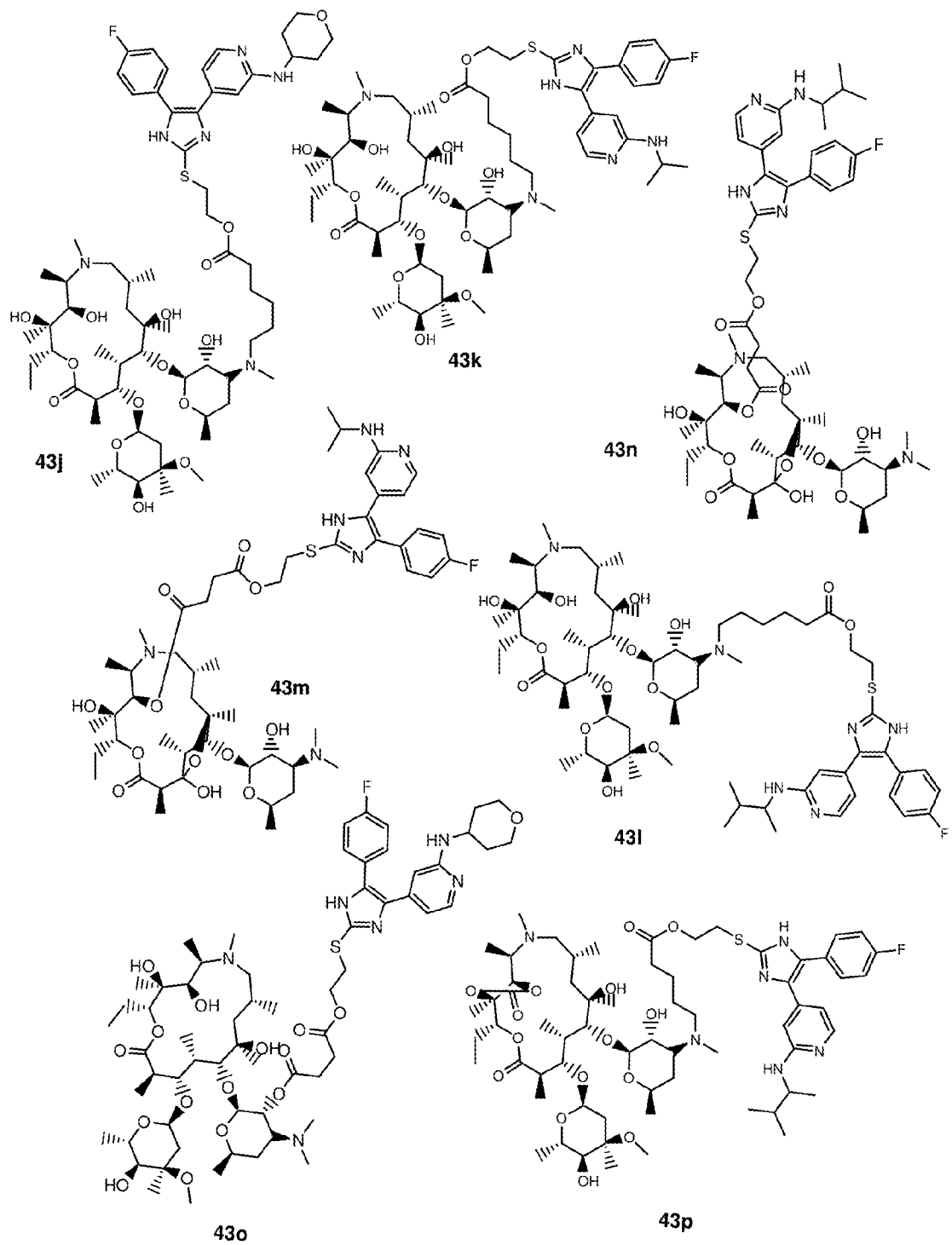
Figure 8:
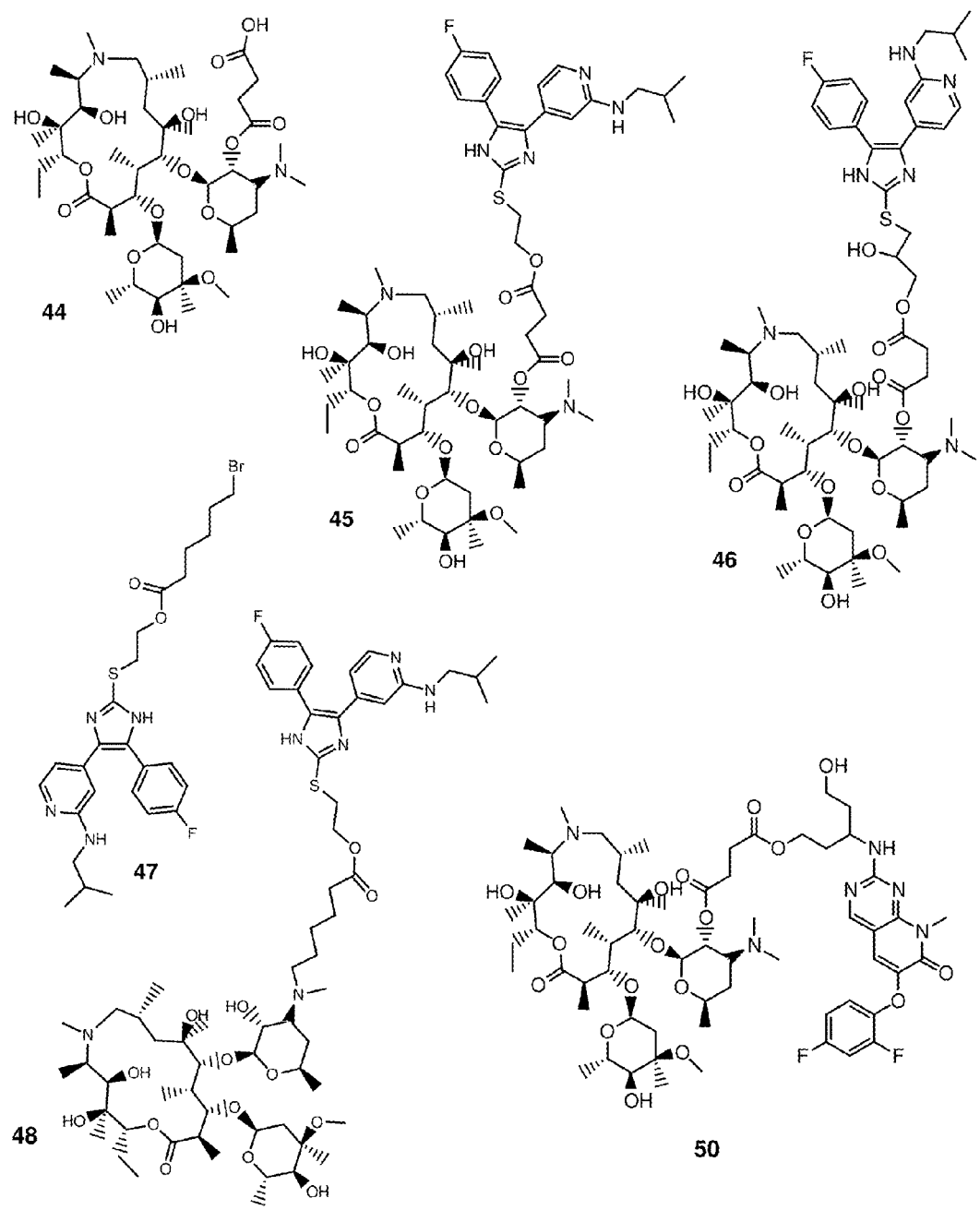
Figure 8:
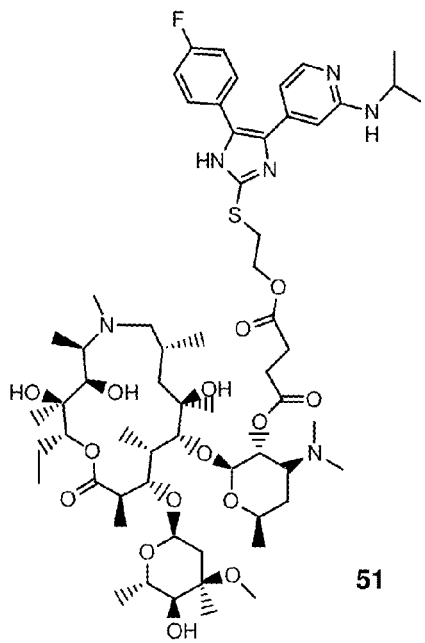
Figure 8:
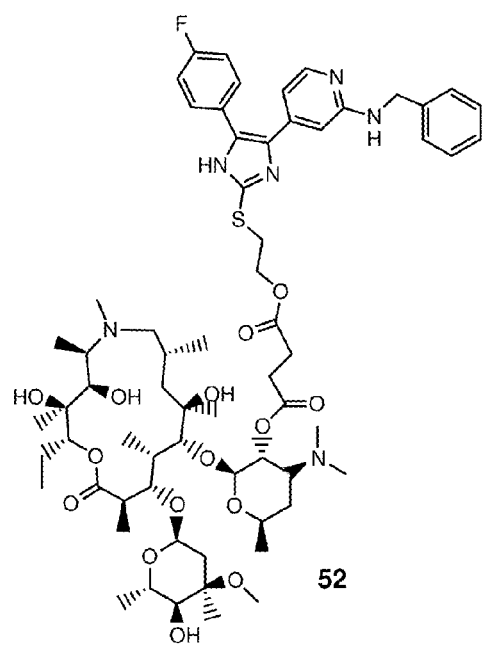
Figure 8:
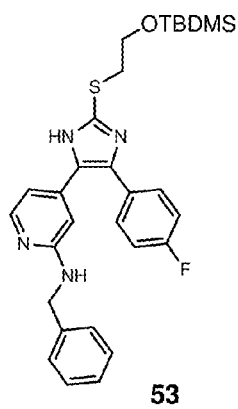
Figure 8:
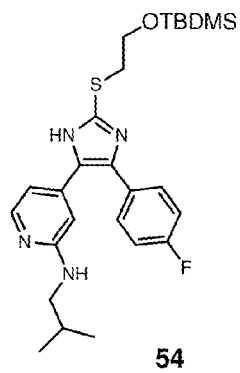
Figure 8:
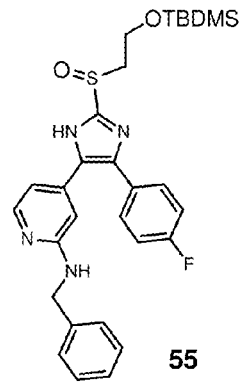
Figure 8:
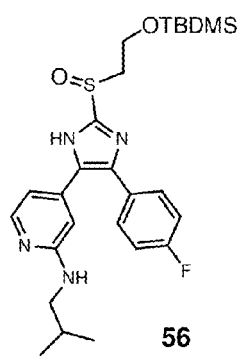
Figure 8:
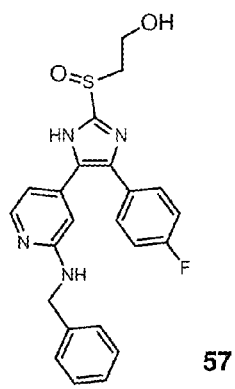
Figure 9:
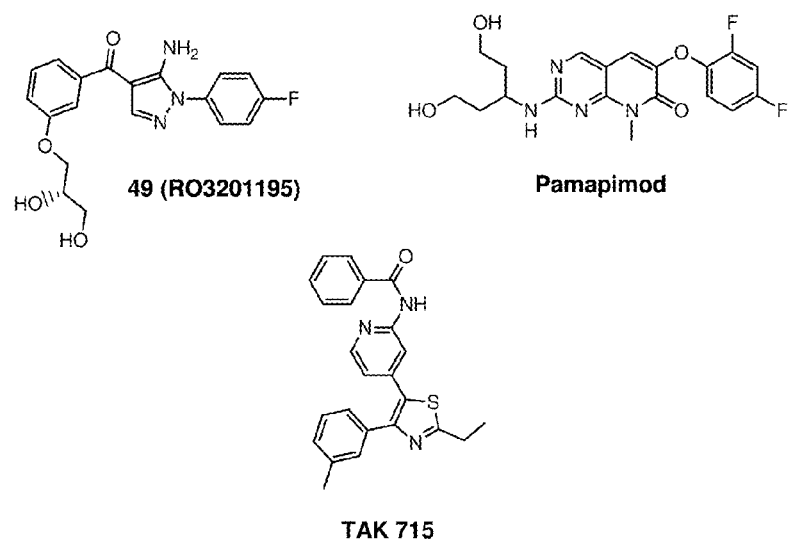
FIG. 9 Example structures of p38 inhibitors RO 3201195 (herein 49), TAK 715 and pamapimod FIG. 10 Effect of TAK 715 and Compound 49-R-isomer on development of murine MB-49 bladder cancer FIG. 11 Effect of TAK 715 on development of murine B-16 melanoma FIG. 12 Effect of 49 and or 43j alone and in combination with gemcitabine on development of murine EL4 lymphoma

In a general scheme, a macrolide carrier is reacted with a linker structure such as succinic anhydride or epichlorohydrin to generate a macrolide with a reactive function that may be in turn linked to an appropriately activated kinase inhibitor. The kinase inhibitor may be drawn from those illustrated herein. Examples of said conjugates are illustrated in FIGS. 7 and 8. In a preferred embodiment, the IL-10 suppressing compound is a macrolide linked p38 inhibitor.

In a preferred embodiment the dose is selected from a range between 0.01 and 100 µmol/kg/day. In a further preferred embodiment, the dose is between 0.1 and 30 µmol/kg per day. In a further preferred embodiment, the dose is between 0.3 and 10 µmol/kg per day.

In another embodiment, the disease is one that is treated or prevented by vaccination and the method of treatment comprises the co-administration of a compound or compounds that stimulate IL-12 and inhibit IL-10 production to a patient in need of same at a therapeutically effective dose. In one embodiment the compound is provided systemically, in another it is provided locally either via intra-tumoural injection, or transdermally (ie. for a skin cancer or a subdermal skin vaccination).

It is clear to those skilled in the art that vaccination is in trial as one means to enhance anti-tumour response. Other diseases treated by vaccination where inadequate vaccine response is a common problem include hepatitis, influenza, papiloma infection, malaria, HIV, Varicella (chickenpox), tetanus (lockjaw), Pertussis (whooping cough) Poliomyelitis (polio), Measles (rubeola), MumpsRubella (german measles) Diphtheria Hepatitis b *Haemophilus influenzae* type b (hib) infections. In a preferred embodiment, the use of the substances exemplified in Formulas 1, 2, 3, 4, 5, 6, 7, 8 and 9 is made in combination with therapeutic vaccines where a strong t-cell response is required.

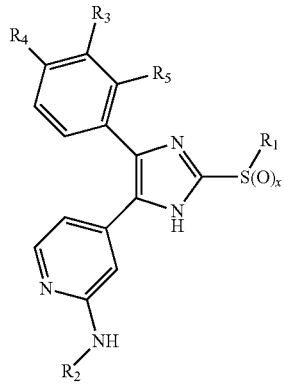

Formula 1

(see schemes 1-2)

wherein x=0, 1, 2

$R_1$=2-hydroxypropyl, 3-hydroxypropyl, 2-hydroxyethyl, 2,3-dihydroxypropyl, 2-hydroxy-3-aminopropyl, 2-hydroxy-3-aminobutyl, 3,4-dihydroxybutyl, 2,3,4-trihydroxybutyl, —(CH$_2$)$_n$—COR with R=OH, O-alkyl (C$_1$-C$_4$), O-alkylaryl, NH$_2$, NHMe, NHOH, and n=1, 2, 3, 4, 5, —CH$_2$—P=O(OR)$_2$ with R=H, CH$_3$, CH$_2$CH$_3$, —CH$_2$—(CH$_2$)$_m$—S(=O)$_n$—R with R=alkyl (C$_1$-C$_5$), OH, NH$_2$, and m=1, 2, 3 and, n=0, 1, 2, glycidyl, 3-methylglycidyl, —CH$_2$—CHOH—COR with R=OH, OMe, OEt, NH2, NHOH, —CH(CH$_2$OH)—COR with R=OH, OMe, OEt, NH2, NHOH, —CH$_2$—CHOH—CN, —CH(CH$_2$OH)—CN, methyl, phenyl, benzyl, $R_2$=hydrogen, methyl, ethyl, n-propyl, isopropyl, sec-butyl, isobutyl, tert-butyl, 2-(3-methyl)butyl, cyclopropyl, cyclobutyl, cyclopentyl, 3-pentyl, cyclohexyl, morpholinyl, methylcyclohexyl, methylcyclopentyl, methylmorpholinyl, hydroxycyclohexyl, hydroxycyclopentyl, benzyl, 1-phenylethyl, tetrahydropyran-4-yl, (4-hydroxy)cyclohexyl, 1-(1 phenyl)propyl, 1-indanyl, 1-(1,2,3,4-tetrahydro)naphthyl, 1-(2-phenyl)propyl, 1-(1-methyl-3-phenyl)propyl, 1,2-diphenylethyl, 1,3-diphenyl-2-propyl, (4-tert-butyl)benzyl, 4-fluorobenzyl, 2-(2-para-xylyl)ethyl, (1-naphthyl)methyl, (2-thiophenyl)methyl, 2-(2-thiophenyl)ethyl, (2-benzo[b]thiophenyl)methyl, (2-furyl)methyl, [(5-methyl)furan-2-yl]- methyl, (2-pyridyl)methyl, (3-pyridyl)methyl, (4-pyridyl)methyl, —(C=O)—R$_2$', R$_2$'=H, C1-C10 alkyl, hydroxyalkyl, aryl, heteroaryl, or arylalkyl; with alkyl chains being branched or linear, 1,5-dihydroxy-3-pentyl, 1,3-dihydroxy-2-propyl, 2,3-dihydroxy-1-propyl, 3-pentyl, 3-methoxy-1-propyl, 2-methylsulfonylethyl, 3-methyoxypropyl, 2-diethylaminocarbonyl-1-ethyl, R$_3$=H, halogen, CF$_3$, OCF$_3$ R$_4$=H, halogen, CF$_3$, OCF$_3$ R$_5$=H, halogen, CF$_3$; or a pharmaceutically acceptable salt thereof.

Alternatively, a p38 inhibitor may be represented by the following structure:

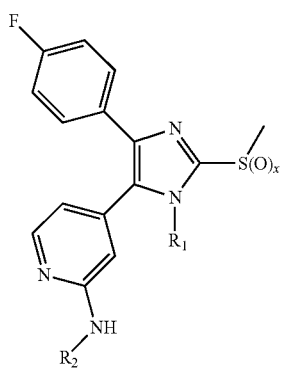

Formula 2

(see scheme 3)

wherein x=0, 1, 2;

R1=methyl, —(CH2)2-OCH3, 2-hydroxyethyl, 2,3-dihydroxypropyl, 1,3-dihydroxy-2-propyl, 1,5-dihydroxy-3-pentyl, cyclohexyl, trans-4-hydroxy-cyclohexyl, 3-hydroxypropyl, 4-tetrahydropyranyl, cyclopropyl, 4-hydroxyethyl, 3-oxo-3-pyrrolidin-1-yl-propyl, 3-pentyl, 2-ethoxycarbonyl-1-ethyl, 2-diethylaminocarbonyl-1-ethyl, 3-bromo-1-propyl, 2-methoxycarbonyl-1-ethyl, 3-oxo-3-piperidin-1-yl-propyl, 2-chloroethyl, 2-carboxy-1-ethyl, 3-oxo-3-morpholin-4-yl-propyl, 3-chloro-1-propyl, 3-carboxypropyl, diethylaminocarbonylmethyl, 4-chlorobutyl, 4-carboxybutyl, 2-oxo-2-morpholin-4-yl-ethyl, 3-fluoropropyl, 2-methylsulfonylethyl, 3-iodopropyl, R$_2$=phenyl, 1-phenylethyl, 1-cyclohexylethyl, cyclohexyl, (2 hydroxycyclohexyl)methyl, 4-tetrahydropyranyl, 2-hydroxycyclohexyl, (1-hydroxy)2-propyl, (2-hydroxy)1-propyl; or a pharmaceutically acceptable salt thereof.

Alternatively, a p38 inhibitor may be represented by the following structure:

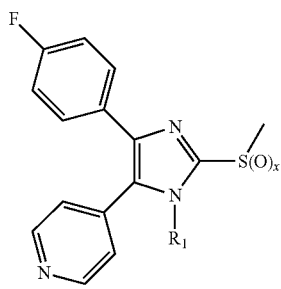

Formula 3

Dissertation Claudia Bracht, University of Tübingen, 2009

Wherein X=0, 1, 2
R$_1$=—(NH)—(C=O)—R$_1$'
R$_1$'=H, C1-C10 alkyl, hydroxyalkyl, aryl, heteroaryl, or arylalkyl; with alkyl chains being branched or linear —(NH)—R$_1$'; or a pharmaceutically acceptable salt thereof.

Alternatively, the p38 inhibitor may be represented as follows:

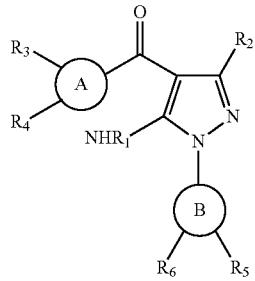

Formula 4

Wherein
R$_1$=hydrogen or acyl;
R$_2$=hydrogen or alkyl;
A=aryl or heteroaryl ring;
B=aryl ring;
R$_3$=selected from the group consisting of:
(a) amino, alkylamino or dialkylamino; (b) acylamino; (c) optionally substituted heterocyclyl; (d) optionally substituted aryl or heteroaryl; (e) heteroalkyl; (f) heteroalkenyl; (g) heteroalkynyl; (h) heteroalkoxy; (i) heteroalkylamino; (j) optionally substituted heterocyclylalkyl (k) optionally substituted heterocyclylalkenyl; (l) optionally substituted heterocyclylalkynyl; (m) optionally substituted cycloalkoxy, cycloalkylalkyloxy, heterocyclylalkoxy, or heterocyclyloxy; (n) optionally substituted heterocyclylalkylamino; (o) optionally substituted heterocyclylalkylcarbonyl; (p) heteroalkylcarbonyl; (q) optionally substituted cycloalkylamino; (r) —NHSO$_2$R$_6$ where R$_6$ is alkyl, heteroalkyl or optionally substituted heterocyclylalkyl;
(s) —NHSO2NR$_7$R$_8$ where R$_7$ and R$_8$ are, independently of each other, hydrogen, alkyl or heteroalkyl;
(t) —Y-(alkylene)-R$_9$ where: Y is a single bond, —O— —NH— or —S(O)n- (where n is an integer from 0 to 2); and R$_9$ is cyano, optionally substituted heteroaryl, —COOH, —COR$_{10}$, —COOR$_{11}$, —CONR$_{12}$R$_{13}$, —SO$_2$—R$_{14}$, —SO$_2$—NR$_{15}$R$_{16}$, —NHSO$_2$R$_{17}$ or NHSO$_2$NR$_{18}$R$_{19}$, where R$_{10}$ is alkyl or optionally substituted heterocycle, R$_{11}$ is alkyl, and R$_{12}$, R$_{13}$, R$_{14}$, R$_{15}$, R$_{16}$, R$_{17}$, R$_{18}$ and R$_{19}$ are, independent of each other, hydrogen, alkyl or heteroalkyl;
(u) —C(NR$_{20}$)(NR$_{21}$R$_{22}$) where R$_{20}$, R$_{21}$ and R$_{22}$ independently represent hydrogen, alkyl or hydroxy, or R$_{20}$ and R$_{21}$ together are —(CH$_2$)$_n$— where n is 2 or 3 and R$_{22}$ is hydrogen or alkyl;
(v) —NHC(X)NR$_{23}$R$_{24}$ where X is —O— or —S— and R$_{23}$ and R$_{24}$ are, independent of each other, hydrogen, alkyl or heteroalkyl;
(w) —CONR$_{25}$R$_{26}$ where R$_{25}$ and R$_{26}$ independently represent hydrogen, alkyl, heteroalkyl or optionally substituted heterocyclylalkyl, or R$_{25}$ and R$_{26}$ together with the nitrogen to which they are attached form an optionally substituted heterocyclyl ring;

(x) —S(O)$_n$R$_{27}$ where n is an integer from 0 to 2, and R$_{27}$ is alkyl, heteroalkyl, optionally substituted cycloalkyl, optionally substituted heterocyclylalkyl, or —NR$_{28}$R$_{29}$ where R$_{28}$ and R$_{29}$ are, independently of each other, hydrogen, alkyl or heteroalkyl;
(y) cycloalkyl alkyl, cycloalkyl alkynyl and cycloalkyl alkynyl, all optionally substituted with alkyl, halo, hydroxy or amino; (z) arylamino alkylene or heteroaryl aminoalkylene;
(aa) Z-alkylene-NR$_{30}$R$_{31}$ or Z-alkylene-OR$_{32}$ where Z is —NH—, —N(alkyl)- or —O—, and R$_{30}$, R$_{31}$ and R$_{32}$ are independently of each other, hydrogen, alkyl or heteroalkyl;
(bb) —OC(O)-alkylene-CO$_2$H or —OC(O)—NR'R" (where R' and R" are independently hydrogen or alkyl);
(cc) heteroarylalkenylene or heteroarylalkynylene;
(dd) X-(alkylene)CH[(CR'R")mOR$_{40}$][(CR'R")nOR$_{40}$] where: X is —O—, —NH—, —NR— (where R is alkyl), —S(O)$_p$— (where p is an integer from 0 to 2); R$_{40}$ is acyl, C(O)OR$_{41}$ (where R$_{41}$ is hydrogen, alkyl, or cycloalkyl); C(O)ONR$_{41}$R$_{42}$ (where R$_{41}$ is as defined above and R$_{42}$ is hydrogen or alkyl); or C(O)NR$_{41}$R$_{42}$ (where R$_{41}$ and R$_{42}$ are as defined above); R' and R", independently, are hydrogen or alkyl; and m and n, independently, are an integer from 0 to 3 provided that m and n are not both zero;
(ee) X-(alkylene)-CH(OH)CH$_2$NHR$_{50}$ where: X is —O—, —NH—, —NR— (where R is alkyl), or —S(O)$_n$— (where n is an integer from 0 to 2); and R$_{50}$ is C(O)OR$_{51}$ and C(O)NR$_{51}$R$_{52}$ (where R$_{52}$ is hydrogen, alkyl, or cycloalkyl and R$_{52}$ is hydrogen or alkyl); and
(ff) X-(alkylene)-CH(NR50)-CH2OH where: X is —O—, —NH—, —NR— (where R is alkyl), or —S(O)$_n$— (where n is an integer from 0 to 2); and R$_{50}$ is C(O)OR$_{51}$ and C(O)NR$_{51}$R$_{52}$ (where R$_{51}$ is hydrogen, alkyl, or cycloalkyl and R$_{52}$ is hydrogen or alkyl);
R$_4$ is selected from the group consisting of:
(a) hydrogen; (b) halo; (c) alkyl; (d) alkoxy; and (e) hydroxy;
R$_5$ is selected from the group consisting of:
(a) hydrogen; (b) halo; (c) alkyl; (d) haloalkyl; (e) thioalkyl; (f) hydroxy; (g) amino; (h) alkylamino; (i) dialkylamino; (j) heteroalkyl; (k) optionally substituted heterocycle; (l) optionally substituted heterocyclylalkyl; (m) optionally substituted heterocyclylalkoxy; (n) alkylsulfonyl; (o) aminosulfonyl, mono-alkylaminosulfonyl or dialkylaminosulfonyl; (p) heteroalkoxy; and (q) carboxy;
R$_6$ is selected from a group consisting of:
(a) hydrogen; (b) halo; (c) alkyl; and (d) alkoxy;
or a pro-drug, individual isomer, mixture of isomers and pharmaceutically acceptable salt thereof.

Alternatively, the p38 inhibitor with the ability to stimulate IL-12 may be represented by the following structure:

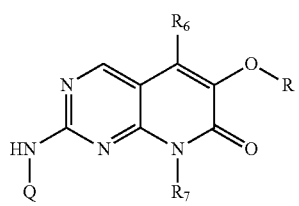

Formula 5 wherein:
R is selected from: (a) alkyl optionally-substituted with one to three of R$_{17}$; (b) cycloalkyl optionally substituted with one, two or three groups selected from R$_{18}$; and (c) optionally-substituted aryl; Q is selected from alkyl, cycloalkyl, substituted cycloalkyl, heterocyclyl, substituted heterocyclyl, and alkyl substituted with one, two or three of halogen, cyano, —OR$_8$, —SR$_8$, —C(=O)R$_8$, —C(O)2R$_8$, —C(=O)NR$_8$R$_9$, —S(O)$_p$R$_{10}$, —C(O)$_2$NR$_8$R$_9$, —S(O)$_2$NR$_8$R$_9$, —NR$_8$R$_9$, cycloalkyl, substituted cycloalkyl, heterocyclyl, and/or substituted heterocyclyl; R$_6$ is hydrogen or lower alkyl; R$_7$ is selected from hydrogen, alkyl, substituted alkyl, halogen, cyano, nitro, hydroxy, alkoxy, haloalkoxy, amino, alkylamino, and optionally-substituted cycloalkyl, heterocyclyl, aryl, or heteroaryl; R$_8$ and R$_9$ are (i) independently selected from hydrogen, alkyl, haloalkyl, hydroxyalkyl, alkoxyalkyl, cycloalkyl, substituted cycloalkyl, heterocyclyl, and substituted heterocyclyl; or (ii) when R$_8$ and R$_9$ are attached to the same nitrogen atom (as in —C(O)$_2$NR$_8$R$_9$, —S(O)$_2$NR$_8$R$_9$, and —NR$_8$R$_9$), R$_8$ and R$_9$ may be taken together to form an optionally-substituted heterocyclyl ring; R$_{10}$ is alkyl, hydroxyalkyl, alkoxyalkyl, cycloalkyl, substituted cycloalkyl, heterocyclyl, or substituted heterocyclyl; R$_{17}$ is at each occurrence independently selected from halogen, haloalkoxy, haloalkyl, alkoxy, or optionally-substituted phenyl, benzyl, phenyloxy, benzyloxy, or cycloalkyl; R$_{18}$ is at each occurrence independently selected from alkyl, substituted alkyl, halogen, haloalkyl, haloalkoxy, cyano, alkoxy, acyl, alkoxycarbonyl, alkylsulfonyl, or optionally-substituted phenyl, phenyloxy, benzyloxy, cycloalkyl, heterocyclyl, or heteroaryl; and p is 1 or 2; or a pharmaceutically acceptable salt thereof.

Alternatively, the p38 inhibitor with the ability to stimulate IL-12 or to inhibit IL-10 may be represented by the following structure:

Formula 6

Wherein
R$_1$=H and R$_2$=OH or O-cladinosyl or
R$_1$, R$_2$=(=O)
X=(C=O) or (C=N—OH) or —[N(CH$_3$)—CH$_2$]— or —[CH$_2$—N(CH$_3$)]—
R$_3$, R$_4$=H or binding site
R$_5$=R6-(NCH$_3$) or binding site
R6=CH$_3$ or binding site
with binding site meaning a position a molecule as defined in formulas 1, 2, 3, 4, 5, 7, 8, or 9 being bound in a way that the macrolide, a spacer, and a functional complex in a linear arrangement are representing R$_1$, R$_2$, R$_3$, R$_4$, or R$_5$ in formula 1 or R$_1$ or R$_2$ in formula 2 or R$_1$ in formula 3 or R$_1$, R$_2$, R$_3$, R$_4$, R$_5$, or R$_6$ in formula 4 or R, R$_6$, R$_7$ or Q in formula 5 or R$_1$, R$_2$, R$_3$, R$_4$, or R$_5$ in formula 7 or R$_1$, R$_2$, R$_3$, R$_4$, or R$_5$ in formula 8 or R$_1$, R$_2$, R$_3$, R$_4$, or R$_5$ in formula 9; or a pharmaceutically acceptable salt thereof.

A spacer, if applicable, comprises a chain of maximal 10 carbon and oxygen atoms, being hydrolysable or not hydrolysable under physiological conditions, that are separating the macrolide from the rest of the molecule.

A functional complex, if applicable, is any arrangement of atoms as defined in the respective definitions.

Alternatively, the p38 kinase inhibitor with the ability to inhibit IL-10 may be represented by the following structure:

Formula 7

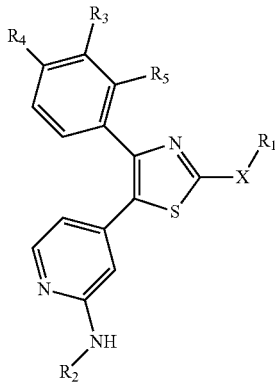

wherein, x=CH$_2$, O, S, S(=O), S(=O)$_2$,
R$_1$=2-hydroxypropyl, 3-hydroxypropyl, 2-hydroxyethyl, 2,3-dihydroxypropyl, 2-hydroxy-3-aminopropyl, 2-hydroxy-3-aminobutyl, 3,4-dihydroxybutyl, 2,3,4-trihydroxybutyl, —(CH$_2$)$_n$—COR with R=OH, O-alkyl (C$_1$-C$_4$), O-alkylaryl, NH$_2$, NHMe, NHOH, and n=1, 2, 3, 4, 5, —CH$_2$—P=O(OR)$_2$ with R=H, CH$_3$, CH$_2$CH$_3$, —CH$_2$—(CH$_2$)$_m$—S(=O)$_n$—R with R=alkyl (C$_1$-C$_5$), OH, NH$_2$, and m=1, 2, 3 and n=0, 1, 2, glycidyl, 3-methylglycidyl, —CH$_2$—CHOH—COR with R=OH, OMe, OEt, NH2, NHOH, —CH(CH$_2$OH)—COR with R=OH, OMe, OEt, NH2, NHOH, —CH$_2$—CHOH—CN, —CH(CH$_2$OH)—CN, methyl, ethyl, 1-propyl, 2-propyl, phenyl, benzyl,
R$_2$=hydrogen, alkyl, aryl, or arylalkyl with 1-10 carbon atoms, acyl with 1-11 carbon atoms,
R$_3$=H, halogen, CH$_3$, CF$_3$, OCF$_3$,
R$_4$=H, halogen, CH$_3$, CF$_3$, OCF$_3$,
R$_5$=H, halogen, CF$_3$; or a pharmaceutically acceptable salt thereof.

In a preferred embodiment, the p38 kinase inhibitor with the ability to inhibit IL-10 may be represented by the following structure:

Formula 8

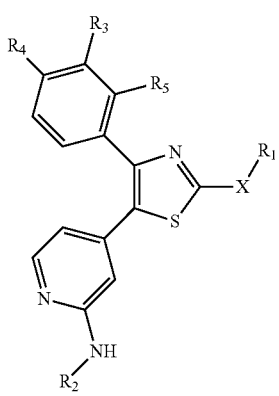

wherein x=CH$_2$, S, S(=O), S(=O)$_2$
R$_1$=2-hydroxypropyl, 3-hydroxypropyl, 2-hydroxyethyl, 2,3-dihydroxypropyl, 2-hydroxy-3-aminopropyl, 2-hydroxy-3-aminobutyl, 3,4-dihydroxybutyl, 2,3,4-trihydroxybutyl, glycidyl, 3-methylglycidyl, methyl, ethyl, 1-propyl, 2-propyl,
R$_2$=hydrogen, alkyl, aryl, or arylalkyl with 1-10 carbon atoms, acyl with 1-11 carbon atoms,
R$_3$=H, halogen, CH$_3$, CF$_3$, OCF$_3$,
R$_4$=H, halogen, CH$_3$, CF$_3$, OCF$_3$,
R$_5$=H, halogen, CF$_3$; or a pharmaceutically acceptable salt thereof.

In a more preferred embodiment, the p38 kinase inhibitor with the ability to inhibit IL-10 may be represented by the following structure:

Formula 9

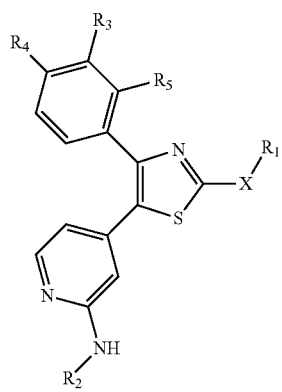

wherein x=CH$_2$
R$_1$=methyl
R$_2$=benzoyl
R$_3$=CH$_3$
R$_4$=H
R$_5$=H; or a pharmaceutically acceptable salt thereof.

The above illustrated embodiments of p38 inhibiting compounds useful according to the invention should not be viewed as limiting the scope of the invention. Rather further compounds having p38 inhibiting activity could also be used in the invention including ARRY-791; SB681323; ISIS101757; VX-702; SCIO323; PS540446; SB856553; KC706; SB230580 and SB281832. Any of the above-provided specific p38 inhibiting compounds, as well as further compounds exhibiting p38 inhibiting activity, may be disclosed in additional documents. In particular, any p38 inhibiting compound disclosed in any of the following documents may be used in the combinations of the present invention. All of the following documents are incorporated herein by reference in their entirety: Foster M L and Halley F S, Drug News Perspect. (2000) 13:488-497; Newton R and Holden N, Biodrugs (2003) 17: 113-129; Boehm J C and Adams J L, Expert Opin. Ther. Patents (2000) 10: 25-37; Jackson P F and Bullington J L, Curr. Top. Med. Chem. (2002) 2:1011-1020; Adams J L, et al., Bioorg. Med. Chem. Lett. (2001) 11:2867-2870; Revesz L, et al., Bioorg. Med. Chem. Lett. (2004) 14:3595-3599; Revesz L, et al., Bioorg. Med. Chem. Lett. (2000) 10: 1261-1264; Revesz L, et al., Bioorg. Med. Chem. Lett. (2002) 12:2109-2112; Dombroski M A, et al., Bioorg. Med. Chem. Lett. (2004) 14:919-923; McIntyre C J, et al., Bioorg. Med. Chem. Lett. (2002) 12:689-692; Rupert K C, et al., Bioorg. Med. Chem. Lett. (2003) 13:347-350; Ottosen E R, et al., J. Med. Chem. (2003) 46:5651-5662; Revesz L, et al., Bioorg. Med. Chem. Lett. (2004) 14:3601-3605; Liu L, et al., Bioorg. Med. Chem. Lett. (2003) 13:3979-3982; Fitzgerald C E, et al., Nat. Struc. Biol. (2003)

10:764-769; Mavunkel B J, et al., Bioorg. Med. Chem. Lett. (2003) 13:3087-3090; Regan J, et al., J. Med. Chem. (2002) 45:2994-3008; Cumming J C, et al., Bioorg. Med. Chem. Lett. (2004) 14:5389-5394; J. Med. Chem (2002), 45, 4695-4705, Laufer, S. et al., J. Med. Chem, (2003), 46, 3230-3244, Laufer, S. et al., Synthesis, (2007), 253-266, Laufer S. et al., J. Med Chem., (2008), 51, 4122-4149, Laufer S. et al., J. Med. Chem., (2008), 51, 5630-5640, Koch p: et al., Dissertation Claudia Bracht (2010), University of Tübingen.

International and US patent application Numbers: In a preferred embodiment, the compounds useful in this invention are drawn from U.S. Pat. No. 7,101,899, U.S. Pat. No. 6,962,933, US20070932125P, US2008207684, US2008146590, US2008119497, US2007167471, US2007049633, US2006252784, U.S. Pat. No. 7,517,901, U.S. Pat. No. 7,285,561, U.S. Pat. No. 6,316,466, US2004097493, U.S. Pat. No. 6,943,158, US2004209903, U.S. Pat. No. 7,189,731, US2005203091, U.S. Pat. No. 7,452,880, US2005197352, U.S. Pat. No. 7,081,462, US2006084803, U.S. Pat. No. 7,439,247, U.S. Pat. No. 6,319,92, U.S. Pat. No. 6,867,211, U.S. Pat. No. 6,936,632, U.S. Pat. No. 7,253,191, US20050656389, WO2007EP58847, US20050524839, US2009306108, US2009239899, US2009270350, U.S. Pat. No. 7,629,363, US2009215817, US2009209577, U.S. Pat. No. 7,037,923, U.S. Pat. No. 7,012,143, U.S. Pat. No. 7,259,171, U.S. Pat. No. 7,005,523, U.S. Pat. No. 6,664,395, U.S. Pat. No. 6,696,464, U.S. Pat. No. 7,056,918, U.S. Pat. No. 7,314,873, U.S. Pat. No. 7,196,095, U.S. Pat. No. 6,809,199, WO03097062, U.S. Pat. No. 6,498,274, U.S. Pat. No. 6,686,467, U.S. Pat. No. 6,881,756, U.S. Pat. No. 7,652,044, U.S. Pat. No. 7,569,571, U.S. Pat. No. 6,579,874, U.S. Pat. No. 6,300,347, U.S. Pat. No. 7,652,022, U.S. Pat. No. 7,615,562, U.S. Pat. No. 6,891,039, U.S. Pat. No. 6,608,072, U.S. Pat. No. 6,919,336, U.S. Pat. No. 6,645,990, U.S. Pat. No. 7,196,104, U.S. Pat. No. 7,504,403, U.S. Pat. No. 7,514,566, U.S. Pat. No. 6,967,254, U.S. Pat. No. 7,321,001, U.S. Pat. No. 7,541,383, U.S. Pat. No. 7,115,617, U.S. Pat. No. 7,354,944, U.S. Pat. No. 6,864,255, U.S. Pat. No. 6,881,737, U.S. Pat. No. 7,390,820, U.S. Pat. No. 7,320,992, U.S. Pat. No. 6,965,030, U.S. Pat. No. 7,320,987, U.S. Pat. No. 7,626,030, U.S. Pat. No. 6,939,874 U.S. Pat. No. 7,307,088, U.S. Pat. No. 7,282,504, U.S. Pat. No. 7,105,682, U.S. Pat. No. 7,101,868, U.S. Pat. No. 6,995,162, U.S. Pat. No. 7,119,111, U.S. Pat. No. 7,507,748, U.S. Pat. No. 7,514,564, U.S. Pat. No. 7,102,009, U.S. Pat. No. 7,531,553, U.S. Pat. No. 6,878,714, U.S. Pat. No. 7,921,762, U.S. Pat. No. 6,849,639, U.S. Pat. No. 7,541,368, U.S. Pat. No. 7,470,689, U.S. Pat. No. 7,309,701, U.S. Pat. No. 7,462,613, U.S. Pat. No. 7,479,501, U.S. Pat. No. 6,770,643, U.S. Pat. No. 6,897,207, U.S. Pat. No. 7,381,841, U.S. Pat. No. 7,227,020, U.S. Pat. No. 6,967,210, U.S. Pat. No. 6,528,315, U.S. Pat. No. 7,179,821, U.S. Pat. No. 7,230,015, U.S. Pat. No. 7,534,803, U.S. Pat. No. 7,309,800, U.S. Pat. No. 7,432,289, U.S. Pat. No. 7,208,629, U.S. Pat. No. 7,166,623, U.S. Pat. No. 7,396,843, U.S. Pat. No. 7,384,963, U.S. Pat. No. 7,183,297, U.S. Pat. No. 7,151,118, U.S. Pat. No. 7,166,597, U.S. Pat. No. 7,423,042, U.S. Pat. No. 7,348,339, U.S. Pat. No. 7,479,558, U.S. Pat. No. 7,612,094, U.S. Pat. No. 6,432,962, U.S. Pat. No. 7,507,734, WO02/32862; WO02/060869; WO00/10563; WO00/31063; WO00/31072; WO00/39116; WO00/63204; WO01/30778; WO02/072571; WO03/035638; WO00/64894; WO01/10865; WO01/074811; WO02/072579; WO2004/014900; WO2004/026302; WO00/25791; WO00/40243; WO01/34605; WO02/16359; WO01/57018; WO2004/076450; WO03/024973; WO03/024971; WO01/90074; WO02/083622; WO02/076447; WO02/092087; WO03/008413; WO03/053967; WO03/076405; WO03/091229; WO01/21591; WO03/020715; WO98/27098; WO00/17204; WO00/17175; WO01/70695; WO01/37837; WO01/38312; WO01/38313; WO01/38314; WO01/64679; WO02/058695; WO03/103950; WO2004/024699; WO02/059083; WO03/088972; WO2004/073628; WO03/033502; WO2004/014920; WO2004/031188; WO00/12074; WO00/59904; WO00/71535; WO02/42292; WO02/46158; WO03/043988; WO2004/022712; WO2004/021988; WO2004/0328742; WO03/084539; WO00/41698; WO02/085859; WO03/087087; WO2004/060306; WO2004/014870; WO00/20402; WO00/07980; WO00/07991; WO00/18738; WO00/55120; WO00/55153; WO00/56738; WO01/47897; WO02/40486; WO03/002544; WO2004/0714402; WO03/032970; WO03/032971; WO03/032972; WO03/032980; WO03/032986; WO03/032987; WO03/033457; WO03/033482; WO2004/010995; WO03/033483; WO03/068747; WO03/093248; WO2006/089798, WO2008/023066, and European Patent No. 01247810.

According to one embodiment of the invention, suitable biologically active variants comprise one or more analogues or derivatives of the compounds described above. Indeed, a single compound, such as those described above, may give rise to an entire family of analogues or derivatives having similar activity and, therefore, usefulness according to the present invention. Likewise, a single compound, such as those described above, may represent a single family member of a greater class of compounds useful according to the present invention. Accordingly, the present invention fully encompasses not only the compounds described above, but analogues and derivatives of such compounds, particularly those identifiable by methods commonly known in the art and recognizable to the skilled artisan.

The compounds disclosed herein may contain chiral centers, which may be either be the (R) or (S) configuration, or may comprise a mixture thereof.

Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein other similar tests which are well known in the art. Examples of methods that can be used to obtain optical isomers of the compounds according to the present invention include the following: i) physical separation of crystals whereby macroscopic crystals of the individual enantiomers are manually separated. This technique may particularly be used when crystals of the separate enantiomers exist (i.e., the material is a conglomerate), and the crystals are visually distinct; ii) simultaneous crystallization whereby the individual enantiomers are separately crystallized from a solution of the racemate, possible only if the latter is a conglomerate in the solid state; iii) enzymatic resolutions whereby partial or complete separation of a racemate by virtue of differing rates of reaction for the enantiomers with an enzyme; iv) enzymatic asymmetric synthesis, a synthetic technique whereby at least one step of the synthesis uses an enzymatic reaction to obtain an enantiomerically pure or enriched synthetic precursor of the desired enantiomer; v) chemical asymmetric synthesis whereby the desired enantiomer is synthesized from an achiral precursor under conditions that produce asymmetry (i.e., chirality) in the product, which may be achieved using chiral catalysts or chiral auxiliaries; vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers; viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions; ix) enantiospecif[iota]c synthesis from non-racemic precursors whereby the desired enantiomer is obtained from non-chiral starting materials and where the stereochemical integrity is not or is only minimally compromised over the course of the synthesis; x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions; xi) chiral gas chromatography whereby the racemate is volatilized and enantiomers are separated by virtue of their differing interactions in the gaseous mobile phase with a column containing a fixed non-racemic chiral adsorbent phase; xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier.

Separation occurs as a result of the non-racemic chiral nature of the membrane which allows only one enantiomer of the racemate to pass through.

Cytokine modulating compounds of the invention may be provided in an enantiomerically enriched form, such as a mixture of enantiomers in which one enantiomer is present in excess (given as a mole fraction or a weight fraction). Enantiomeric excess is understood to exist where a chemical substance comprises two enantiomers of the same compound and one enantiomer is present in a greater amount than the other enantiomer. Unlike racemic mixtures, these mixtures will show a net optical rotation. With knowledge of the specific rotation of the mixture and the specific rotation of the pure enantiomer, the enantiomeric excess (abbreviated "ee") can be determined by known methods. Direct determination of the quantities of each enantiomer present in the mixture is possible with NMR spectroscopy and chiral column chromatography. The compounds of the invention can have a specific degree of enantiomeric purity for a single enantiomer (e.g., at least about 75%, at least about 80%, at least about 85%, at least about 90%, at least about 95%, at least about 96%, at least about 97%, at least about 98%, at least about 99%, or at least about 99.5%).

The compounds described herein can also be in the form of an ester, amide, salt, solvate, prodrug, or metabolite provided they maintain pharmacological activity according to the present invention. Esters, amides, salts, solvates, prodrugs, and other derivatives of the compounds of the present invention may be prepared according to methods generally known in the art, such as, for example, those methods described by J. March, Advanced Organic Chemistry: Reactions, Mechanisms and Structure, 4th Ed. (New York: Wiley-Interscience, 1992), which is incorporated herein by reference.

The compounds may also be synthesized with atoms of deuterium, or $^{13}C$ carbon in certain positions in order to modify properties of stability, or resistance to metabolic enzymes.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, [gamma]-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like. Esters of the compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine.

Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0 [deg.]C. to 60 [deg.]C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the compositions of the invention may exist in different forms. For example, the compounds may exist in stable and metastable crystalline forms and isotropic and amorphous forms, all of which are intended to be within the scope of the present invention.

If a compound useful according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound of the invention is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The present invention further includes prodrugs and active metabolites of the compounds of the invention. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine and/or carboxylic acid moiety. Any of these can be used in combination with the disclosed compounds to achieve a desired effect.

Pharmaceutical Formulations

While it is possible for the individual compound used in the composition of the present invention to be administered in the raw chemical form, it is preferred for the compounds to be delivered as a pharmaceutical composition. Accordingly, there are provided by the present invention pharmaceutical compositions comprising combinations of compounds as described herein. As such, the compositions of the present invention comprise the pharmaceutically active compounds, as described above, or pharmaceutically acceptable esters, amides, salts, solvates, analogs, derivatives, or prodrugs thereof. Further, the inventive compositions can be prepared and delivered in a variety of combinations. For example, the composition can comprise a single composition containing all of the active ingredients. Alternately, the composition can comprise multiple compositions comprising separate active ingredients but intended to be administered simultaneously, in succession, or in otherwise close proximity of time.

The compounds of the invention can be prepared and delivered together with one or more pharmaceutically acceptable carriers therefore, and optionally, other therapeutic ingredients. Carriers should be acceptable in that they are compatible with any other ingredients of the composition and not harmful to the recipient thereof. A carrier may also reduce any undesirable side effects of the agent. Such carriers are known in the art. See, Wang et a (1980) J. Parent. Drug Assn. 34(6):452-462, herein incorporated by reference in its entirety. Compositions of the present invention may include short-term, rapid-onset, rapid-offset, controlled release, sustained release, delayed release, and pulsatile release compositions, providing the compositions achieve administration of a compound as described herein. See Remington's Pharmaceutical Sciences (18th ed.; Mack Publishing Company, Eaton, Pa., 1990), herein incorporated by reference in its entirety.

Pharmaceutical compositions according to the present invention are suitable for various modes of delivery, including oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrasternal, and transdermal), topical (including dermal, buccal, and sublingual), vaginal, urethral, and rectal administration. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

The pharmaceutical compositions may be conveniently made available in a unit dosage form, whereby such compositions may be prepared by any of the methods generally known in the pharmaceutical arts (e.g., shaping into a tablet or forming an aqueous suspension). Pharmaceutical compositions according to the present invention suitable for oral dosage may take various forms, such as tablets, capsules, caplets, and wafers (including rapidly dissolving or effervescing), each containing a predetermined amount of the active agent. The compositions may also be in the form of a powder or granules, a solution or suspension in an aqueous or non-aqueous liquid, and as a liquid emulsion (oil-in-water and water-in-oil). The active agents may also be delivered as a bolus, electuary, or paste. It is generally understood that methods of preparations of the above dosage forms are generally known in the art, and any such method would be suitable for the preparation of the respective dosage forms for use in delivery of the compositions according to the present invention. In one embodiment, compound may be administered orally in combination with a pharmaceutically acceptable vehicle such as an inert diluent or an edible carrier. Oral compositions may be enclosed in hard or soft shell gelatin capsules, may be compressed into tablets or may be incorporated directly with the food of the patient's diet. The percentage of the composition and preparations may be varied; however, the amount of substance in such therapeutically useful compositions is preferably such that an effective dosage level will be obtained.

Hard capsules containing the compound may be made using a physiologically degradable composition, such as gelatin. Soft capsules comprise the compound, which may be mixed with water or an oil medium such as peanut oil, liquid paraffin, or olive oil. The compositions of these tablets contain, in addition to the drug, various soluble excipients, such as lactose, powdered sucrose, dextrose, and mannitol. The solid dosage forms of the present invention may optionally be coated, and examples of suitable coating materials include, but are not limited to, cellulose polymers (such as cellulose acetate phthalate, hydroxypropyl cellulose, hydroxypropyl methylcellulose, hydroxypropyl methylcellulose phthalate, and hydroxypropyl methylcellulose acetate succinate), polyvinyl acetate phthalate, acrylic acid polymers and copolymers, and methacrylic resins, zein, shellac, and polysaccharides.

Powdered and granular compositions of a pharmaceutical preparation of the invention may be prepared using known methods. Such compositions may be administered directly to a patient or used in the preparation of further dosage forms, such as to form tablets, fill capsules, or prepare an aqueous or oily suspension or solution by addition of an aqueous or oily vehicle thereto. Each of these compositions may further comprise one or more additives, such as dispersing or wetting agents, suspending agents, and preservatives. Additional excipients (e.g., fillers, sweeteners, flavoring, or coloring agents) may also be included in these compositions. Liquid compositions of the pharmaceutical composition of the invention which are suitable for oral administration may be prepared, packaged, and sold either in liquid form or in the form of a dry product intended for reconstitution with water or another suitable vehicle prior to use. A tablet containing one or more compounds according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agents. Adjuvants or accessory ingredients for use in the compositions of the present invention can include any pharmaceutical ingredient commonly deemed acceptable in the art, such as binders, fillers, lubricants, disintegrants, diluents, surfactants, stabilizers, preservatives, flavoring and coloring agents, and the like. Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluloses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the composition according to the present invention may be anionic, cationic, amphoteric, or nonionic surface active agents. Stabilizers may be included in the compositions to inhibit or lessen reactions leading to decomposition of the active agents, such as oxidative reactions. Solid dosage forms may be formulated so as to provide a delayed release of the active agents, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agents over a prolonged period of time), and may or may not also be delayed release. Sustained release compositions are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Compositions for parenteral administration include aqueous and non-aqueous sterile injection solutions, which may further contain additional agents, such as anti-oxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

Compositions for rectal delivery of the compositions of the present invention include rectal suppositories, creams, ointments, and liquids. Suppositories may be presented as the active agents in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

In certain embodiments, the compounds and compositions disclosed herein can be delivered via a medical device. Such delivery can generally be via any insertable or implantable medical device, including, but not limited to Intratumoural sponges. Administration of the composition according to the invention comprises administering a single pharmaceutically active compound as described herein; administering a pharmaceutically active compound as described herein with one or more further pharmaceutically active compounds described herein; or administering one or more pharmaceutically active compounds described herein in combination with one or more further pharmaceutically active compounds (i.e., co-administration). Accordingly, it is recognized that the pharmaceutically active compounds in the compositions of the invention can be administered in a fixed combination (i.e., a single pharmaceutical composition that contains both active materials). Alternatively, the pharmaceutically active compounds may be administered simultaneously (i.e., separate compositions administered at the same time). In another embodiment, the pharmaceutically active compounds are administered sequentially (i.e., administration of one or more pharmaceutically active compounds followed by separate administration or one or more pharmaceutically active compounds). One of skill in the art will recognized that the most preferred method of administration will allow the desired therapeutic effect.

Delivery of a therapeutically effective amount of a composition according to the invention may be obtained via administration of a therapeutically effective dose of the composition. The effective amount of the compositions would be expected to vary according to the weight, sex, age, and medical history of the subject. The compound is preferentially administered for a sufficient time period to alleviate the undesired symptoms and the clinical signs associated with the condition being treated. Methods to determine efficacy and dosage are known to those skilled in the art. See, for example, Isselbacher et al. (1996) Harrison's Principles of Internal Medicine 13 ed., 1814-1882, herein incorporated by reference.

The present invention also includes an article of manufacture providing a composition comprising the compounds described herein. The article of manufacture can include a vial or other container that contains a composition suitable for use according to the present invention together with any carrier, either dried or in liquid form. The dosages could be solid forms (e.g., tablets, caplets, capsules, or the like) or liquid forms (e.g., vials), each comprising a single active ingredient, but being provided in blister packs, bags, or the like, for administration in combination.

EXAMPLES

The present invention will now be described with specific reference to various examples. The following examples are not intended to be limiting of the invention and are rather provided as exemplary embodiments.

Example 1 tert-Butyl 4-methylpyridin-2-ylcarbamate (1)

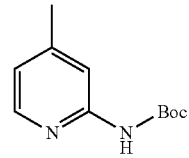

To a solution of freshly distilled tert-butanol (450 mL) and di-tert-butyl dicarbonate (16.81 g, 77.0 mmol) was added slowly 2-aminopicoline (7.57 g, 70.0 mmol). The mixture was stirred at room temperature for 3 d, the solvent was removed in vacuo and the residue was recrystallized from 2-propanol, affording 12.30 g (84%) of a colorless solid.

General procedure for the synthesis of N-alkyl/phenylalkyl-N-boc-4-methylpyrindin-2-amines (General Procedure A)

To a solution of tert-butyl 4-methylpyridin-2-ylcarbamate 1 (1 equiv.) in dry DMF was added under an argon-atmosphere NaH (1.25 equiv., 60% oil dispersion) at 0° C. in such a manner that the temperature was kept below 5° C. The reaction mixture was kept at 0° C. for 20 min followed by the addition of the alkyl/phenylalkyl halides (1.15 equiv.) at the same temperature. After additional stirring at 0° C. for 30 min the mixture was allowed to warm to room temperature within 1 h. After stiffing at room temperature for 1 h, $H_2O$ and EtOAc were added. The organic layer was washed subsequently with HCl (0.1 M), sodium bicarbonate and brine, dried ($Na_2SO_4$), and concentrated in vacuo. The residue was purified by flash chromatography.

General procedure for the synthesis of N-alkyl-4-methylpyrindin-2-amines via Buchwald-Hartwig-reaction (General procedure B)

2-Bromo-4-methylpyridine (1.0 equiv.), amine (1.2 equiv.) or corresponding hydrochlorides (1.2 equiv.), NaOt-Bu (1.4 equiv., or in case of hydrochlorides 2.4 equiv.), $Pd_2(dba)_3$ (0.02 equiv.), BINAP (0.04 equiv.) were dissolved in dry toluene under argon atmosphere. The mixture was heated to 70° C. or to reflux until the disappearance of the starting material 2-bromo-4-methylpyridine (TLC-control: n-hexane/EtOAc 3:1 or 1:1). The mixture was allowed to cool to room temperature before n-hexane was added. The formed precipitate was filtered off and the filtrate concentrated to dryness. Once again, n-hexane was added to the residue and the precipitate was filtered off. The filtrate was concentrated in vacuo. The crude product was used in the next reaction (except compound 3d which was purified by flash chromatography).

General procedure for the synthesis of N-alkyl-N-boc-4-methylpyridin-2-amines via boc-protection (General procedure C)

N-Alkyl-4-methylpyridin-2-amine 3 (1.0 equiv.) was dissolved in dry DCM and subsequently treated with di-tertbutyl dicarbonate (2.5 equiv.) and DMAP (catalytic amounts). The reaction mixture was stirred for 16 h at room temperature and the solvent was removed in vacuo. n-Hexane was added to the residue, the precipitate was filtered off, and the filtrate was concentrated under reduced pressure. The residue was purified by flash chromatography.

General procedure for the synthesis of the 2-(2-(boc(alkyl/phenylalkyl)amino)pyridin-4-yl)-1-(4-fluorophenyl)ethanones (General procedure D)

N-Alkyl/phenylalkyl-N-boc-4-methylpyridin-2-amine (1.0 equiv.) and ethyl 4-fluorobenzoate (1.0 or 1.1 equiv.) were dissolved in dry THF under argon atmosphere. The solution was cooled to 0° C. and NaHMDS (2 equiv. 2 M in THF) was added dropwise. The mixture was allowed to stir at this temperature for 1 h and additional 2.5 h at room temperature. The reaction was quenched with saturated NH$_4$Cl solution, EtOAc was added and the mixture was extracted with water (2×). The organic layer was dried (Na$_2$SO$_4$) and concentrated in vacuo. The crude product was purified by flash chromatography.

General procedure for the preparation of 2-(2-(boc(alkyl/phenylalkyl)amino)pyridin-4-yl)-1-(4-fluorophenyl)ethan-1,2-dion-2-oximes (General procedure E)

A solution of 1-(4-fluorophenyl)-2-(2-(alkyl/phenylalkyl (boc)amino)pyridin-4-yl)ethanone (1.0 equiv.) in glacial acetic acid was cooled to 10° C. and a solution of NaNO$_2$ (3.0 equiv. in water (only as much water as was necessary to obtain a clear solution) was added dropwise. The reaction was allowed to warm to room temperature while stiffing for 2.5 h. Water and EtOAc were added and the mixture was extracted with sodium bicarbonate several times. The organic phase was dried (Na$_2$SO$_4$) and concentrated in vacuo. After drying at the oil pump the oximes were obtained as foams which were used without purification for the next reaction.

General procedure for the preparation of 2-amino-2-(2-(1-alkyl/phenylalkylamino)-pyridin-4-yl)-1-(4-fluorophenyl)ethanone hydrochlorides (General procedure F)

In a three-necked flask 2-(2-(boc(alkyl/phenylalkyl)amino)pyridin-4-yl)-1-(4-fluorophenyl)ethan-1,2-dion-2-oxime was dissolved in methanol and saturated methanolic hydrogen chloride. Pd/C 10% was added. The reaction flask was evacuated and flooded with hydrogen (4×). The suspension was stirred under hydrogen atmosphere at atmospheric pressure for 16 h. The catalyst was filtered off and washed thoroughly with methanol. The filtrate was concentrated in vacuo. The crude product was used without further purification for the next step.

General procedure for the preparation of 5-(2-(1-alkyl/phenylalkylamino)pyridin-4-yl)-4-(4-fluorophenyl)-1,3-dihydroimidazol-2-thiones (General procedure G)

2-Amino-2-(2-(1-phenylalkylamino)pyridin-4-yl)-1-(4-fluorophenyl)ethanone hydrochloride (1.0 equiv.) was dissolved in absolute DMF and potassium thiocyanate (1.3 equiv.) was added. The reaction mixture was heated to reflux for 3 h. The suspension was cooled to room temperature and slowly diluted with water. The yellow precipitate was filtered off and washed with water.

General Procedure for the Synthesis of Title Compounds (General Procedure H)

To a solution of 5-(2-(alkyl/phenylalkylamino)pyridin-4-yl)-4-(4-fluorophenyl)-1,3-dihydroimidazol-2 thiones (1.0 equiv.) and KOt-Bu (1.1 or 1.2 equiv.) in dry MeOH was added under argon atmosphere the appropriate alkylhalide (1.1 or 1.2 equiv.). The solution was heated to reflux until complete disappearance of the starting material (thiones) and cooled to room temperature. After extraction with water and EtOAc the organic phase was washed with water (2×), dried (Na$_2$SO$_4$) and evaporated under reduced pressure. The crude product was purified by flash chromatography or by crystallization.

For the cited examples, an appropriate mass spectrum by ESI ionization in a thermo-Finnigan ion-trap, consistent with the structure drawn, was obtained.

| Example Nr. | Name | Formula | Procedure |
|---|---|---|---|
| 2a | N-Boc-4-methyl-N-(1-phenylethyl)pyridin-2-amine | | A |
| 2b | N-Benzyl-N-boc-4-methylpyridin-2-amine | | A |
| 2c | N-Boc-N-isobutyl-4-methylpyridin-2-amine | | A |
| 2d | N-Boc-N-ethyl-4-methylpyridin-2-amine | | A |
| 2e | N-Boc-N,4-dimethyl-pyridin-2-amine | | A |

-continued

| Example Nr. | Name | Formula | Procedure |
|---|---|---|---|
| 2f | N-Boc-4-methyl-N-(3-methylbutan-2-yl)pyridin-2-amine | | C |
| 2g | N-Boc-4-methyl-N-(sec-butyl)pyridin-2-amine | | C |
| 2h | N-Boc-4-methyl-N-isopropyl-pyridin-2-amine | | C |
| 2i | N-Boc-4-methyl-N-(tetrahydro-2H-pyran-4-yl)pyridin-2-amine | | C |
| 3a | 4-Methyl-N-(3-methylbutan-2-yl)pyridin-2-amine | | B |
| 3b | N-sec-Butyl-4-methylpyridin-2-amine | | B |
| 3c | N-Isopropyl-4-methylpyridin-2-amine | | B |
| 3d | 4-Methyl-N-(tetrahydro-2H-pyran-4-yl)pyridin-2-amine | | B |

-continued

| Example Nr. | Name | Formula | Procedure |
|---|---|---|---|
| 4a | 2-(2-(Boc(1-phenylethyl)amino)pyridin-4-yl)-1-(4-fluorophenyl)ethanone | | D |
| 4b | 2-(2-(1-Benzyl(boc)amino)pyridin-4-yl)-1-(4-fluorophenyl)ethanone | | D |
| 4c | 2-(2-(Boc(isobutyl)amino)pyridin-4-yl)-1-(4-fluorophenyl)ethanone | | D |
| 4d | 2-(2-(Boc(ethyl)amino)pyridin-4-yl)-1-(4-fluorophenyl)ethanone | | D |

| Example Nr. | Name | Formula | Procedure |
|---|---|---|---|
| 4e | 2-(2-(Boc(methyl)amino)pyridin-4-yl)-1-(4-fluorophenyl)ethanone | | D |
| 4f | 2-(2-(Boc(3-methylbutan-2-yl)amino)pyridin-4-yl)-1-(4-fluorophenyl)ethanone | | D |
| 4g | 2-(2-(Boc(sec-butyl)amino)pyridin-4-yl)-1-(4-fluorophenyl)ethanone | | D |
| 4h | 2-(2-(Boc(isopropyl)amino)pyridin-4-yl)-1-(4-fluorophenyl)ethanone | | D |
| 4i | 2-(2-(Boc(tetrahydro-2H-pyran-4-yl)amino)pyridin-4-yl)-1-(4-fluorophenyl)ethanone | | D |
| 5a | 2-(2-(Boc(1-phenylethyl)amino)pyridin-4-yl)-1-(4-fluorophenyl)ethan-1,2-dion-2-oxime | | E |
| 5b | 2-(2-(1-Benzyl(boc)amino)pyridin-4-yl)-1-(4-fluorophenyl)ethan-1,2-dion-2-oxime | | E |
| 5c | 2-(2-(Boc(isobutyl)amino)pyridin-4-yl)-1-(4-fluorophenyl)ethan-1,2-dion-2-oxime | | E |

-continued

| Example Nr. | Name | Formula | Procedure |
|---|---|---|---|
| 5d | 2-(2-(Boc(ethyl)amino)pyridin-4-yl)-1-(4-fluorophenyl)ethan-1,2-dion-2-oxime | | E |
| 5e | 2-(2-(Boc(methyl)amino)pyridin-4-yl)-1-(4-fluorophenyl)ethan-1,2-dion-2-oxime | | E |
| 5f | 2-(2-(Boc(3-methylbutan-2-yl)amino)pyridin-4-yl)-1-(4-fluorophenyl)ethan-1,2-dion-2-oxime | | E |
| 5g | 2-(2-(Boc(sec-butyl)amino)pyridin-4-yl)-1-(4-fluorophenyl)ethan-1,2-dion-2-oxime | | E |

-continued

| Example Nr. | Name | Formula | Procedure |
|---|---|---|---|
| 5h | 2-(2-(Boc(isopropyl)amino)pyridin-4-yl)-1-(4-fluorophenyl)ethan-1,2-dion-2-oxime | | E |
| 5i | 2-(2-(Boc(tetrahydro-2H-pyran-4-yl)amino)pyridin-4-yl)-1-(4-fluorophenyl)ethan-1,2-dion-2-oxime | | E |
| 6a | 2-Amino-1-(4-fluorophenyl)-2-(2-(1-phenylethylamino)pyridin-4-yl)ethanone hydrochloride | | F |
| 6b | 2-Amino-2-(2-(1-benzylamino)pyridin-4-yl)-1-(4-fluorophenyl)ethanone hydrochloride | | F |

| Example Nr. | Name | Formula | Procedure |
|---|---|---|---|
| 6c | 2-Amino-1-(4-fluorophenyl)-2-(2-(isobutylamino)pyridin-4-yl)ethanone hydrochloride | | F |
| 6d | 2-Amino-2-(2-(ethylamino)pyridin-4-yl)-1-(4-fluorophenyl)ethanone hydrochloride | | F |
| 6e | 2-Amino-1-(4-fluorophenyl)-2-(2-(methylamino)pyridin-4-yl)ethanone-hydrochloride | | F |
| 6f | 2-Amino-1-(4-fluorophenyl)-2-(2-(3-methylbutan-2-ylamino)pyridin-4-yl)ethanone hydrochloride | | F |
| 6g | 2-Amino-1-(4-fluorophenyl)-2-(2-(sec-butylamino)pyridin-4-yl)ethanone hydrochloride | | F |
| 6h | 2-Amino-1-(4-fluorophenyl)-2-(2-(isopropylamino)pyridin-4-yl)ethanone hydrochloride | | F |
| 6i | 2-Amino-1-(4-fluorophenyl)-2-(2-(tetrahydro-2H-pyran-4-ylamino)pyridin-4-yl)ethanone hydrochloride | | F |
| 7a | 4-(4-Fluorophenyl)-5-(2-(1-phenylethylamino)pyridin-4-yl)-1,3-dihydro-imidazol-2-thione | | G |

| Example Nr. | Name | Formula | Procedure |
|---|---|---|---|
| 7b | 5-(2-(1-Benzylamino)pyridin-4-yl)-4-(4-fluorophenyl)-1,3-dihydro-imidazol-2-thione | | G |
| 7c | 4-(4-Fluorophenyl)-5-(2-(isobutyl-amino)pyridin-4-yl)-1,3-dihydro-imidazol-2-thione | | G |
| 7d | 5-(2-Ethylamino)pyridin-4-yl)-4-(4-fluorophenyl)-1,3-dihydro-imidazol-2-thione | | G |
| 7e | 4-(4-Fluorophenyl)-5-(2-(methylamino)pyridin-4-yl)-1,3-dihydro-imidazol-2-thione | | G |
| 7f | 4-(4-Fluorophenyl)-5-(2-(3-methylbutan-2-ylamino)pyridin-4-yl)-1,3-dihydro-imidazol-2-thione | | G |
| 7g | 4-(4-Fluorophenyl)-5-(2-(sec-butylamino)pyridin-4-yl)-1,3-dihydro-imidazol-2-thione | | G |
| 7h | 4-(4-Fluorophenyl)-5-(2-(isopropyl-amino)pyridin-4-yl)-1,3-dihydro-imidazol-2-thione | | G |
| 7i | 4-(4-Fluorophenyl)-5-(2-(tetrahydro-2H-pyran-4-ylamino)pyridin-4-yl)-1,3-dihydro-imidazol-2-thione | | G |
| 8a | 3-(4-(4-Fluorophenyl)-5-(2-(1-phenylethyl-amino)pyridin-4-yl)-1H-imidazol-2-ylthio)propane-1,2-diol | | H |

-continued

| Example Nr. | Name | Formula | Procedure |
|---|---|---|---|
| 8b | 3-(5-(2-(1-Benzylamino)pyridin-4-yl)-4-(4-fluorophenyl)-1H-imidazol-2-ylthio)propane-1,2-diol | | H |
| 8c | 3-(4-(4-Fluorophenyl)-5-(2-(isobutylamino)pyridin-4-yl)-1H-imidazol-2-ylthio)propane-1,2-diol | | H |
| 8d | 3-(5-(2-(Ethylamino)pyridin-4-yl)-4-(4-fluorophenyl)-1H-imidazol-2-ylthio)propane-1,2-diol | | H |
| 8e | 3-(4-(4-Fluorophenyl)-5-(2-(methylamino)pyridin-4-yl)-1H-imidazol-2-ylthio)propane-1,2-diol | | H |
| 8f | 3-(4-(4-Fluorophenyl)-5-(2-(3-methylbutan-2-ylamino)pyridin-4-yl)-1H-imidazol-2-ylthio)propane-1,2-diol | | H |
| 8g | 3-(4-(4-Fluorophenyl)-5-(2-sec-butylamino)pyridin-4-yl)-1H-imidazol-2-ylthio)propane-1,2-diol | | H |
| 8h | 3-(4-(4-Fluorophenyl)-5-(2-(isopropylamino)pyridin-4-yl)-1H-imidazol-2-ylthio)propane-1,2-diol | | H |
| 8i | 3-(4-(4-Fluorophenyl)-5-(2-(tetrahydro-2H-pyran-4-ylamino)pyridin-4-yl)-1H-imidazol-2-ylthio)propane-1,2-diol | | H |
| 8j | 3-(4-(4-Fluorophenyl)-5-(2-(3-methylbutan-2-ylamino)pyridin-4-yl)-1H-imidazol-2-ylthio)propane-1-ol | | H |
| 8k | 2-(4-(4-Fluorophenyl)-5-(2-(3-methylbutan-2-ylamino)pyridin-4-yl)-1H-imidazol-2-ylthio)ethanol | | H |

| Example Nr. | Name | Formula | Procedure |
|---|---|---|---|
| 8l | (2R)-3-(4-(4-Fluorophenyl)-5-(2-(3-methylbutan-2-ylamino)pyridin-4-yl)-1H-imidazol-2-ylthio)propane-1,2-diol | | H |
| 8m | (2S)-3-(4-(4-Fluorophenyl)-5-(2-(3-methylbutan-2-ylamino)pyridin-4-yl)-1H-imidazol-2-ylthio)propane-1,2-diol | | H |
| 8n | (2R)-3-(4-(4-Fluorophenyl)-5-(2-(isopropylamino)pyridin-4-yl)-1H-imidazol-2-ylthio)propane-1,2-diol | | H |
| 8o | (2S)-3-(4-(4-Fluorophenyl)-5-(2-(isopropylamino)pyridin-4-yl)-1H-imidazol-2-ylthio)propane-1,2-diol | | H |
| 8p | Methyl 2-(4-(4-fluorophenyl)-5-(2-(1-phenylethylamino)pyridin-4-yl)-1H-imidazol-2-ylthio)acetate | | H |
| 8q | 2-(4-(4-fluorophenyl)-5-(2-(1-phenylethylamino)pyridin-4-yl)-1H-imidazol-2-ylthio)acetic acid | | H |
| 8r | Diethyl (4-(4-fluorophenyl)-5-(2-(1-phenylethylamino)pyridin-4-yl)-1H-imidazol-2-ylthio)methylphosphonate | | H |
| 8s | Methyl 2-(4-(4-fluorophenyl)-5-(2-(3-methylbutan-2-ylamino)pyridin-4-yl)-1H-imidazol-2-ylthio)acetate | | H |
| 8t | Methyl 2-(4-(4-fluorophenyl)-5-(2-(isopropylamino)pyridin-4-yl)-1H-imidazol-2-ylthio)acetate | | H |
| 8u | 2-(4-(4-Fluorophenyl)-5-(2-(isopropylamino)pyridin-4-yl)-1H-imidazol-2-ylthio)ethanol | | H |

-continued

| Example Nr. | Name | Formula | Procedure |
|---|---|---|---|
| 8v | 2-(4-(4-Fluorophenyl)-5-(2-(tetrahydro-2H-pyran-4-ylamino)pyridin-4-yl)-1H-imidazol-2-ylthio)ethanol | | H |
| 8w | 2-(4-(4-Fluorophenyl)-5-(2-(1-phenylethylamino)pyridin-4-yl)-1H-imidazol-2-ylthio)ethanol | | H |
| 8x | 2-(4-(4-Fluorophenyl)-5-(2-isobutylaminopyridin-4-yl)-1H-imidazol-2-ylthio)ethanol | | H |
| 8y | 2-[5-(2-Benzylaminopyridin-4-yl)-4-(4-fluorophenyl)-1H-imidazol-2-ylthio]ethanol | | H |

Example 9

1-(4-Fluorphenyl)-2-(fluorpyridin-4-yl)ethanone (9)

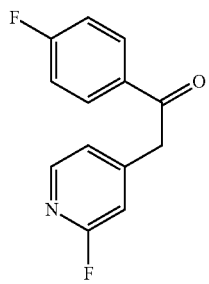 [SMILES: O=C(Cc1ccnc(F)c1)c1ccc(F)cc1]

2-Fluoro-4-methylpyridine (4.44 g, 0.04 mol) and ethyl 4-fluorobenzoate (6.73 g, 0.04 mol) were dissolved in dry THF under argon atmosphere. The solution was cooled to 0° C. and NaHMDS (40 mL, 0.08 mol) was added dropwise. The mixture was allowed to stir at this temperature for 2 h and additional 1 h at room temperature. The reaction was treated with EtOAc and washed with 10% HCl (2×). The organic layer was dried over $Na_2SO_4$ and the solvent removed in vacuo to afford a colorless solid.

yield: 8.81 g (94%)

Example 10

1-(4-Fluorphenyl)-2-(2-fluorpyridin-4-yl)-ethan-1,2-dion-2-oxime (10)

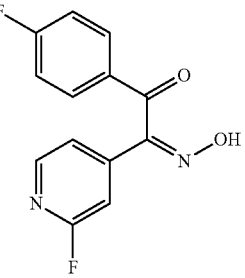

A solution of 9 (1.35 g, 5.8 mmol) in glacial acetic acid (10 mL) was cooled to 10° C. and a solution of $NaNO_2$ (1.21 g, 17.5 mmol) in water (7 mL) was added dropwise. The reaction was allowed to warm to room temperature while stirring for 0.5 h. Water was added and the mixture was stirred for another 3 h. The white precipitate was filtrated, washed with water and died in vacuo.

yield: 1.47 g (97%)

Example 11

2-Amino-1-(4-fluorphenyl)-2-(2-fluorpyridin-4-yl)ethanone hydrochloride (11)

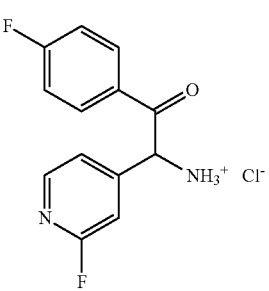 [SMILES: [NH3+]C(C(=O)c1ccc(F)cc1)c1ccnc(F)c1 ; [Cl-]]

Compound 10 (2.01 g, 0.077 mol) was dissolved in isopropanol (25 mL) and saturated isopropanolic hydrogen chloride (25 mL). Pd/C 10% (0.35 g) was added. The reaction flask was evacuated and flushed with hydrogen gas (4×). The suspension was agitated at room temperature under hydrogen atmosphere at atmospheric pressure for 6 h. The catalyst was filtered off and washed thoroughly with methanol. The filtrate was concentrated in vacuo to afford a yellowish solid.

yield: 2.20 g (100%)

$^1$H-NMR (DMSO) δ 6.56 (s, 1H, CH), 7.32-7.41 (m, 2H, 4-F-Ph), 7.51-7.53 (m, 2H, $C^3/C^5$—H 2-F-Pyr), 8.17-8.28 (m, 2H, 4-F-Ph), 8.30 (d, J=5.8 Hz, 1H, $C^6$—H 2-F-Pyr), 9.36 (bs, 3H, $NH_3^+$)

IR (ATR) ṽ ($cm^{-1}$) 2809 ($NH_3^+$), 2619, 1695 (CO), 1618, 1597, 1520, 1509, 1418, 1281, 1255, 1239 (CF), 1164, 970, 848, 833, 792

Example 12

4-(4-Fluorphenyl)-5-(2-fluorpyridin-4-yl)-1,3-dihydroimidazol-2-thione (12)

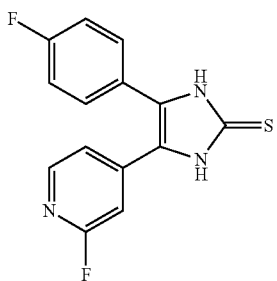 [SMILES: Fc1ccc(-c2[nH]c(=S)[nH]c2-c2ccnc(F)c2)cc1]

Compound 11 (0.43 g, 1.5 mmol) was dissolved in absolute MeOH and potassium thiocyanate (0.03 g, 3.1 mmol) was added. The reaction mixture was heated to reflux for 1.5 h forming a yellow precipitate. The suspension was cooled to room temperature and slowly diluted with water (40 mL). The yellow precipitate was filtered off, washed with water and dried. yield: 0.27 g (62%)

Example 13

2-(4-(4-Fluorphenyl)-5-(2-fluorpyridin-4-yl)-1H-imidazol-2-ylthio)ethanol (13)

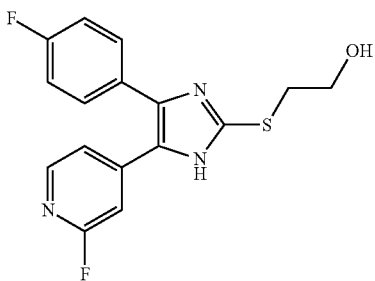 [SMILES: OCCSc1nc(-c2ccc(F)cc2)c(-c2ccnc(F)c2)[nH]1]

Compound 12 (0.87 g, 3 mmol) and 2-bromoethanol (0.41 g 3.3 mmol) were suspended in absolute MeOH (35 mL) and sodium ethoxide (0.25 g, 3.6 mmol) was added. The reaction mixture was stirred for 4 h at rt, the solvent was removed and the crude product was purified by flash chromatography (SiO₂, DCM/MeOH 9-1) to afford a colorless solid.

yield: 0.58 g (58%)

Example 8z (1R,4R)-4-(4-(4-(4-Fluorophenyl)-2-(2-hydroxyethylthio)-1H-imidazol-5-yl)pyridin-2-yl-amino)-cyclohexanol

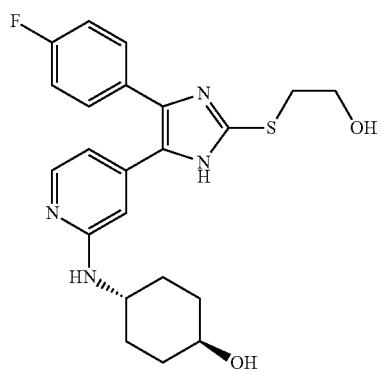 [SMILES: OCCSc1nc(-c2ccc(F)cc2)c(-c2ccnc(N[C@H]3CC[C@H](O)CC3)c2)[nH]1]

Compound 8z was prepared by irradiating 13 (160 mg, 0.48 mmol) and trans-4-aminocylohexanol (440 mg, 3.84 mmol) in a sealed tube at 135° C. for 3.5 h, by moderating the initial microwave power (250 W). After cooling down to room temperature in a stream of compressed air the yellow solid was dissolved in MeOH, transferred in a round-bottomed flask and the solvent was evaporated. The crude product was purified by flash chromatography (SiO₂, from DCM/MeOH 95:5 to DCM/MeOH 75:25).

yield: 82 mg (40%)

For more details see: *J. Med. Chem*, 2008, 51, 5630-5640

More examples: *J. Med. Chem*, 2003, 46, 3230-3244, *J. Med. Chem*, 2008, 51, 4122-4149 and *Synthesis* 2007, 253-266, Dissertation Claudia Bracht, University of Tübingen, 2010 "Synthese, biologische Testung & physikochemische Charakterisierung von tetra- and trisubstituierten Imidazolenals Inhibitoren der p38α MAP Kinase"

Example 14

Use of Kinase Inhibitors that are Coupled to Macrocyclic Rings to Increase Macrophage Uptake and Maintain Exposure. (See FIG. 7 for General Scheme)

Aqueous Workup for Macrolide-Residues-Containing Compounds:
General Procedure:

Partition between 2% aqueous citric acid solution and ethyl acetate,

Washing of the aqueous phase with ethyl acetate,

Aqueous phase made basic by addition of potassium carbonate,

Extraction with ethyl acetate,

Washing of the ethyl acetate extracts with water and brine, drying over sodium sulfate, concentration in vacuo.

Example 15

Synthesis of 3'-desmethyl azithromycin (15)

20 g of Azithromycin were dissolved in 120 ml of methanol in a 500 ml Erlenmeyer flask. 12 g of potassium carbonate were dissolved in 80 ml of water and cooled to RT. The Erlenmeyer flask was equipped with a suitable stirrer and 6 g of sodium bicarbonate. The solution of potassium carbonate and 6.3 g of iodine were added, and the mixture was stirred vigorously at RT, until the dark colour disappeared. A second batch of the of iodine and solid potassium carbonate were added. The procedure was repeated, until MS shows full conversion ($[M+H]^+$=749->735

1 g of sodium bisulfite was added to remove excess oxidants, and all volatiles were evaporated. The solid residue was finely ground and extensively extracted by soxhlet extraction with Acetonitril. The extract was concentrated to a volume of. 75 ml and left standing at room temperature for at least 1 day and subsequently another day at −4° C. The solids were collected and recrystallised from methanol with addition of. 1-2 ml of water. Crystallisation proceeds for about 3 days in an open vessel to yield 10 g (51%) of big, shiny crystals.

Example 16

Synthesis of 3'-desmethyl erythromycin (16)

19.6 g of Erythromycin were subjected to the same procedure as described in Example 15 to obtain the 3'-demethylated product.

Example 17

Synthesis of 3'-desmethyl-3'-oxiranylmethyl azithromycin (17)

20 mg of 15 (example 15), 20 ml of epichlorohydrin and 25 g of potassium carbonate were combined in 250 ml of 2-propanol and stirred for 12 h at room temperature. Progress of the reaction was monitored by MS ($[M+H]^+$=735->791). When finished, the reaction mixture was partitioned between water and ethyl acetate (100 ml each). The aqueous phase was washed with 100 ml of ethyl acetate, and the combined organic phases were extracted twice with 150 ml 250 mM aqueous citric acid. After washing of the aqueous phase with ethyl acetate to remove residual epichlorohydrin, it was treated with solid $K_2CO_3$ until neutralisation (pH=7-8). The product was extracted with ethyl acetate and, after drying and concentration, recrystallised from acetonitril to yield 17 g (80%) of off white crystals.

Example 18

Synthesis of 3'-desmethyl-3'-oxiranylmethyl erythromycin (18)

The procedure of example 17 was applied to compound 16 (example 16 to obtain the desired product.

Example 19

Synthesis of Compound 19

145 mg of 4-(4-Fluoro-phenyl)-5-[2-(1-phenyl-ethyl-amino)-pyridin-4-yl]-1,3-dihydro-imidazole-2-thione (7a) and 289 mg of 17 (example 17) were dissolved in 20 ml of methanol and put under argon. 35 mg of potassium tert.-butanoate were added, and the mixture was stirred for 16 h. The mixture was subjected to aqueous workup as described above and purified by chromatography over silica gel (acetone-cyclohexane 2+3, 1% triethylamine) to yield 33 mg of a yellow solid.

Example 20

Synthesis of Compound 20

170 mg of 4-(4-Fluoro-phenyl)-5-pyridin-4-yl-1,3-dihydro-imidazole-2-thione and 495 mg of compound 17 (example 17) were dissolved in 20 ml of methanol and placed under argon. 30 mg of potassium tert.-butanoate were added, and the mixture was stirred for 65 h. The mixture was subjected to aqueous workup as described above and purified by chromatography over silica gel (acetone-cyclohexane 2+3, 1% triethylamine) to yield 67 mg of a yellow solid.

Example 21

Synthesis of Compound 21

The procedure of example 20 was applied to compound 18 (example 18) instead of compound 17 to obtain the desired product.

Example 22

Synthesis of Compound 22

10 mg of compound 20 (example 20) were dissolved in 5 ml of 1 M aqueous HCl. The process of hydrolysis was monitored by MS (M/z=1061->903 for $[M+H]^+$ in an electrospray MS). When the reaction was complete, the mixture was subjected to aqueous workup as described above to yield 8 mg of an off white solid.

Example 23

Synthesis of Compound 23 a) 2.85 g of compound 15 (example 15) were suspended in 10 ml of pyridine, and 464 mg of diglycolic acid anhydride were added. After addition of a few crystals of DMAP, the mixture was stirred for 1 h. When MS shows completion of the reaction, the mixture was diluted with 50 ml of ether and decanted. 2 extractions (2 h each) of the residue with ether (50 ml) were performed to obtain a yellow sandy residue, that was directly used for the next step.

b) The residue of a) was suspended in 10 ml of DMSO. 300 mg of sodium carbonate were added, and 4 ml of epichlorohydrin. After heating to 80° C. for 30 min, MS showed complete conversion. A second product with higher mass ($[M+H]^+$=943) with a chlorine pattern comes from the respective halohydrin. Chromatography with an acetone gradient in cyclohexane (1% triethylamine) yielded 290 mg of the epoxide derivative.

c) 150 mg of the product of b) and 62 mg of 4-(4-Fluoro-phenyl)-5-[2-(1-phenyl-ethylamino)-pyridin-4-yl]-1,3-dihydro-imidazole-2-thione (7a) were dissolved in 5 ml of DMSO and placed under argon. 21 mg of potassium tert.-butanoate were added, and the mixture was kept at room temperature for 16 h. The product was precipitated with water, and chromatographed with an acetone gradient in cyclohexane (1% triethylamine) to obtain 25 mg of the title compound.

Example 24

Synthesis of 24

The procedure of example 23c was applied to 4-(4-Fluoro-phenyl)-5-pyridin-4-yl-1,3-dihydro-imidazole-2-thione instead of 4-(4-Fluoro-phenyl)-5-[2-(1-phenyl-ethyl-amino)-pyridin-4-yl]-1,3-dihydro-imidazole-2-thione to obtain the title compound.

Example 25

Synthesis of 25

21 mg of 6-(2,4-Difluoro-phenoxy)-2-methanesulfonyl-8-methyl-8H-pyrido[2,3-d]pyrimidin-7-one (U.S. Pat. No. 6,965,030 or U.S. Pat. No. 7,320,987) and 40 mg of 15 (example 15) were dissolved in 1 ml of DMSO and heated to 65° C. for 16 h. Preparative HPLC with an acetonitril gradient in water (0.05% HCOOH) yields 15 mg of the title compound.

Example 26

Synthesis of 26

55 mg of [5-Amino-1-(4-fluoro-phenyl)-1H-pyrazol-4-yl]-(3-hydroxy-phenyl)-methanone (example 49d) and 157 mg of compound 17 (example 17) were combined with 100 mg of potassium carbonate in 2 ml DMSO. The mixture was heated to 65° C. for 50 h and purified by preparative HPLC (Methanol gradient in water, 0.05% HCOOH). 30 mg of a sticky yellow powder were obtained.

Example 27

Synthesis of 4-({2-[2-Ethyl-3,4,10-trihydroxy-13-(5-hydroxy-4-methoxy-4,6-dimethyl-tetrahydro-pyran-2-yloxy)-3,5,6,8,10,12,14-heptamethyl-15-oxo-1-oxa-6-aza-cyclopentadec-11-yloxy]-3-hydroxy-6-methyl-tetrahydro-pyran-4-yl}-methyl-amino)-butyric acid ethyl ester (27)

290 mg of 15 (example 15) and 200 µl of ethyl-4-bromobutyrate were combined in 750 µl of 2-propanol and heated to 85° C. for 24 h. The mixture was subjected to aqueous workup to yield 245 mg of the title compound.

Example 28

Synthesis of Lithium 4-({2-[2-ethyl-3,4,10-trihydroxy-13-(5-hydroxy-4-methoxy-4,6-dimethyl-tetrahydro-pyran-2-yloxy)-3,5,6,8,10,12,14-heptamethyl-15-oxo-1-oxa-6-aza-cyclopentadec-11-yloxy]-3-hydroxy-6-methyl-tetrahydro-pyran-4-yl}-methyl-amino)-butyrate (28)

27 (example 27) was dissolved in a THF/water mixture, and 290 µl of a 1 M solution of lithium hydroxide in water were added. When MS showed completion of the reaction, the product was isolated by evaporation of all volatiles and purified by dissolution in methanol and filtration through celite.

Example 29

Synthesis of 29

1.8 g of compound 28 (example 28), and 1.5 ml of epichlorohydrin were mixed in 10 ml of DMSO. 1 ml of DIEA was added, and the mixture was warmed to 65° C., until MS analysis shows complete conversion of the starting material. The mixture was subjected to aqueous workup as described in example 17, and chromatographed with an acetone gradient in cyclohexane (1% triethylamine) to yield 1.0 g of product. Further material can be isolated as the respective halohydrin, which may be used for the coupling steps as well.

Example 30

Synthesis of 5-({2-[2-Ethyl-3,4,10-trihydroxy-13-(5-hydroxy-4-methoxy-4,6-dimethyl-tetrahydro-pyran-2-yloxy)-3,5,6,8,10,12,14-heptamethyl-15-oxo-1-oxa-6-aza-cyclopentadec-11-yloxy]-3-hydroxy-6-methyl-tetrahydro-pyran-4-yl}-methyl-amino)-valeric acid acid ethyl ester (30)

The title compound can be obtained by applying the procedure of example 27 and substituting ethyl-4-bromobutyrate with ethyl-5-bromovalerate.

Example 31

Synthesis of 6-({2-[2-Ethyl-3,4,10-trihydroxy-13-(5-hydroxy-4-methoxy-4,6-dimethyl-tetrahydro-pyran-2-yloxy)-3,5,6,8,10,12,14-heptamethyl-15-oxo-1-oxa-6-aza-cyclopentadec-11-yloxy]-3-hydroxy-6-methyl-tetrahydro-pyran-4-yl}-methyl-amino)-capronic acid acid ethyl ester (31)

The title compound can be obtained by applying the procedure of example 27 and substituting ethyl-4-bromobutyrate with ethyl-6-bromohexanoate.

Example 32

Synthesis of Lithium 4-({2-[2-ethyl-3,4,10-trihydroxy-13-(5-hydroxy-4-methoxy-4,6-dimethyl-tetrahydro-pyran-2-yloxy)-3,5,6,8,10,12,14-heptamethyl-15-oxo-1-oxa-6-aza-cyclopentadec-11-yloxy]-3-hydroxy-6-methyl-tetrahydro-pyran-4-yl}-methyl-amino)-valerate (32)

The title compound can be obtained by applying the procedure of example 28 and substituting compound 27 with compound 30 (example 30).

Example 33

Synthesis of Lithium 4-({2-[2-ethyl-3,4,10-trihydroxy-13-(5-hydroxy-4-methoxy-4,6-dimethyl-tetrahydro-pyran-2-yloxy)-3,5,6,8,10,12,14-heptamethyl-15-oxo-1-oxa-6-aza-cyclopentadec-11-yloxy]-3-hydroxy-6-methyl-tetrahydro-pyran-4-yl}-methyl-amino)-hexanoate (33)

The title compound can be obtained by applying the procedure of example 28 and substituting 27 with 31 (example 31).

Example 34

Synthesis of 34

The title compound can be obtained by applying the procedure of example 29 and substituting compound 28 with compound 32 (example 32).

Example 35

Synthesis of 35

150 mg of compound 32 (example 32) were dissolved in 2 ml of molten ethylene carbonate and kept at 110° C. for 4 h. Aqueous workup and chromatography with an acetone gradient in cyclohexane (1% triethylamine) produced 35 mg of the title compound.

Example 36

Synthesis of 36 a) 2.2 g of ethylene glycol and 550 µl of pyridine were dissolved in 10 ml of THF. 1 ml of 6-bromo hexanoyl chloride was added. The mixture was stirred for 4 h and then partitioned between ethyl acetate and dil. hydrochloric acid. The organic phase was washed with water and brine, dried over sodium sulfate and concentrated to yield 1.45 g of an oily product, that is directly used for the following step.

b) 2 g of compound 15 (example 15) and 575 mg of hydroxyethyl-6-bromohexanoate were dissolved in 20 ml of DMSO, and heated to 60° C. for 16 h. Aqueous workup and chromatography with an acetone gradient in cyclohexane (1% triethylamine) gave 1 g of the title compound.

Example 37

Synthesis of 37

33 mg of compound 35 (example 35) and 13 mg of tetrabromomethane were dissolved in 700 µl of dichloromethane. 15 mg of triphenylphosphine were added. After stirring for 1 h, 33 mg of tetrabromomethane and 38 mg of triphenylphosphine were added. The reaction was complete after 10 min. The mixture was subjected to aqueous workup as described above to yield a sufficiently pure product.

Example 38

Synthesis of 38

The title compound can be obtained by applying the procedure of example 37 and substituting compound 35 with compound 36 (example 36).

Example 39

Synthesis of 39 a) 200 g Azithromycin were dissolved in 500 ml dichloromethane and cooled to 5° C. in an ice bath. 32.5 g acetic acid anhydride were added dropwise, so that the inner temperature does not exceed 25° C. The ice bath was removed and the mixture was stirred for 2 h at room temperature.

The dichloromethane was evaporated to dryness and the residue was dissolved in 500 ml of 3 N aqueous hydrochloric acid. After complete dissolution, the mixture was checked by MS for completion (target mass: [m+H]+=633).

The reaction mixture was extracted once with 100 ml diethylether to remove most of the yellowish-green colour and cooled in an ice bath. 500 ml dichloromethane were added and the mixture was neutralized at a temperature below 5° C. with 250 ml of 6 N aqueous sodium hydroxide solution. 40 g Sodium carbonate were added with vigorous stirring, the phases were separated and the aqueous phase was extracted 3 times with 200 ml dichloromethane. The organic extracts were combined, dried over sodium sulfate and evaporated to dryness.

b) A stirred solution of 13.3 ml oxalylchloride in dry dichloromethane (400 ml) under Argon is chilled to −72° C.±5° C. by an acetone-dry ice-bath and 14.5 ml dimethylsulfoxide were slowly added (30 min total addition time) through a dropping funnel. Initially a vigorously gas evolution was observed with every drop. The solution was stirred at −72° C.±5° C. for 20 min, then a solution of 20 g of compound from example 39a) (dried for at least 3 hours at 60° C. and less than 1 mbar) in dry dichloromethane (120 ml) was added slowly (40 min total addition time) through a dropping funnel. The colorless suspension was kept at −72° C.±5° C. for 1 hour. Then 40 ml of dry ethyl diisopropylamine were added slowly (30 min total addition time) through a dropping funnel which furnished a clear yellowish solution. The reaction mixture was stirred for another 20 min at −72° C.±5° C., subsequently followed by addition of 50 ml methanol in one portion. The solution was kept at −72° C.±5° C. for another 10 min, before being allowed to reach room temperature.

The reaction mixture was transferred into a separation funnel and the reaction flask washed with additional dichloromethane (150 ml). The combined organic layers were washed with saturated aqueous sodium bicarbonate solution twice (400 ml each) and one time with brine (400 ml). The organic layer was dried over sodium sulfate and evaporated under reduced pressure.

To remove the acetyl group, methanol (300 ml) was added to the yellow foam and the solution was stirred at room temperature over night. The solvent was removed under reduced pressure and the yellow oil taken up into 500 ml of ethyl acetate. The organic layer was extracted with 500 ml 1N sodium hydroxide/brine (1:1), and dried over sodium sulfate. 200 ml of toluene were added and the solution concentrated to 35 ml. Crystallisation already starts on concentration. In order to complete the precipitation the suspension was kept at −20° C. over night to yield 10.5 g of a colourless powder.

c) 3.44 g of compound from example 39b were dissolved in 20 ml of dichloromethane, and 1.2 g of succinic anhydride were added. After stirring for 5 h, 13 g of ethylene carbonate were added, and all volatiles are removed in vacuo. The mixture was kept for 24 h at 80-90° C. Fragmentation of the double charged target mass peak ([m+2H]$^{2+}$=367) shows (partial) rearrangement of the initial 2'-acylation (main fragment=432) to 11-acylation (main fragment=576) of the macrolide ring. The mixture was subjected to aqueous workup as described above (example 17) and chromatography with an acetone gradient in cyclohexane (1% triethylamine). The fractions with the right mass ([m+H]$^+$=733) and fragmentation pattern were isolated and concentrated. If still some ethylene carbonate is present, another aqueous workup needs to be performed.

Example 40

Synthesis of 40

The title compound can be obtained by applying the procedure of example 37 and substituting compound 35 with compound 39 (example 39).

Example 41

Synthesis of 41

4.4 g of Azithromycin were dissolved in 50 ml of dichloromethane. 600 mg of succinic anhydride were added. After stirring over night, 7 g of ethylene carbonate were added, and the mixture was concentrated and kept at 115° C. for 4 h. The mixture was subjected to a fast filtration through silica gel (acetone gradient in cyclohexane, 1% triethylamine) and purified by prep. HPLC (Methanol gradient in water). yield: 500 mg.

Example 42

Synthesis of 42

The title compound could be obtained by applying the procedure of example 37 and substituting compound 35 with compound 41 (example 41).

or

Compound 44 (1.00 g, 1.18 mmol), 44, EDCI*HCl (452 mg, 2.36 mmol), and DMAP (cat. amount) were suspended in dry DCM (20 mL) and were stirred at RT for 15 min. Afterwards 2-bromoethanol (72 µl, 0.98 mmol) was added and the mixture was stirred at room temperature overnight. The residue was concentrated to dryness and taken up in an aqueous citric acid solution (5%). After extraction with EtOAc (2×) the aqueous phase was brought to pH ~8 with NaHCO$_3$. The alkaline phase was extracted with EtOAc (2×) and the organic phases were dried (Na$_2$SO$_4$) and concentrated to dryness to yield 1.20 g of the 42 as a white solid which was used without further purification.

Example 43

General Synthesis for Coupling of a Macrolide Element with a Kinase Inhibitor or its Precursor a) 0.5 mmol of an activated macrolide precursor X and 0.65 mmol of a kinase inhibitor or its precursor Y were dissolved in 3 ml of DMSO and thoroughly degassed by passing argon through the solution. While keeping the mixture under argon, 0.75 mmol potassium tert.-butylate were added. The mixture was stirred for 12 hours, and then subjected to aqueous workup as described above. The residue was purified by prep. HPLC and lyophilisation.

b) To remove the cladinose sugar residue, the product was stirred with 1M aqueous hydrochloric acid under MS control, until the reaction (loss of 158 mass units) was finished. Aqueous workup yielded the product with almost complete conversion.

| X | Y | product | procedure |
|---|---|---------|-----------|
| 29 | 5-[2-(1,2-Dimethyl-propylamino)-pyridin-4-yl]-4-(4-fluoro-phenyl)-1H-imidazole-2-thiol (7f) | 43a | a) |
| 29 | 4-(4-Fluoro-phenyl)-5-[2-(tetrahydro-pyran-4-ylamino)-pyridin-4-yl]-1H-imidazole-2-thiol (7i) | 43b | a) |
| 29 | 4-(4-Fluoro-phenyl)-5-[2-(tetrahydro-pyran-4-ylamino)-pyridin-4-yl]-1H-imidazole-2-thiol (7i) | 43c | a) and b) |
| 29 | 5-(2-sec-Butylamino-pyridin-4-yl)-4-(4-fluoro-phenyl)-1H-imidazole-2-thiol (7g) | 43d | a) |
| 29 | 5-(2-sec-Butylamino-pyridin-4-yl)-4-(4-fluoro-phenyl)-1H-imidazole-2-thiol (7g) | 43e | a) and b) |
| 29 | 5-(4-Fluoro-phenyl)-4-(2-isopropylamino-pyridin-4-yl)-1H-imidazole-2-thiol (7h) | 43f | a) |
| 29 | 4-(4-Fluoro-phenyl)-5-pyridin-4-yl-1H-imidazole-2-thiol | 43g | a) |
| 29 | [5-Amino-1-(4-fluoro-phenyl)-1H-pyrazol-4-yl]-(3-hydroxy-phenyl)-methanone (example 49d) | 43h | a) |
| 29 | 5-(4-Fluoro-phenyl)-4-[2-(1-phenyl-ethylamino)-pyridin-4-yl]-1H-imidazole-2-thiol (7a) | 43i | a) |
| 38 | 4-(4-Fluoro-phenyl)-5-[2-(tetrahydro-pyran-4-ylamino)-pyridin-4-yl]-1H-imidazole-2-thiol (7i) | 43j | a) |
| 38 | 5-(4-Fluoro-phenyl)-4-(2-isopropylamino-pyridin-4-yl)-1H-imidazole-2-thiol (7h) | 43k | a) |
| 38 | 5-[2-(1,2-Dimethyl-propylamino)-pyridin-4-yl]-4-(4-fluoro-phenyl)-1H-imidazole-2-thiol (7f) | 43l | a) |
| 40 | 5-(4-Fluoro-phenyl)-4-(2-isopropylamino-pyridin-4-yl)-1H-imidazole-2-thiol (7h) | 43m | a) |
| 40 | 5-[2-(1,2-Dimethyl-propylamino)-pyridin-4-yl]-4-(4-fluoro-phenyl)-1H-imidazole-2-thiol (7f) | 43n | a) |
| 42 | 4-(4-Fluoro-phenyl)-5-[2-(tetrahydro-pyran-4-ylamino)-pyridin-4-yl]-1H-imidazole-2-thiol (7i) | 43o | a) |
| 37 | 5-[2-(1,2-Dimethyl-propylamino)-pyridin-4-yl]-4-(4-fluoro-phenyl)-1H-imidazole-2-thiol (7f) | 43p | a) |

Example 44

Synthesis of Compound 44

Azithromycin (5 g; 6.7 mmol) (9a-aza-9a-methyl-9-deoxo-9a-homoerythromycin) was dissolved in DCM (25 mL). To the resulting clear solution was added succinic anhydride (738 mg; 7.4 mmol, 1.1 equiv.) and 4-DMAP (catalytic). The reaction was stirred overnight at room temperature. The solvent was evaporated in vacuo and the resulting white solid was used for the following steps without further purification. Yield: 5.2 g; 91%.

Example 45

Synthesis of Compound 45

44 (73 mg, 0.086 mmol), EDCI*HCl (21 mg, 0.11 mmol), and DMAP (cat. amount) were suspended in dry DCM (0.6 mL) and were shaken at RT for 15 min. Afterwards 8x (30 mg, 0.078 mmol) was added and the mixture was shaken at room temperature overnight. DCM was added and the mixture was washed with sodium bicarbonate solution and brine, and concentrated to dryness.

The crude product was purified by column chromatography (eluent: acetone+1% TEA). Yield 24 mg.

Example 46

Synthesis of Compound 46

44 (73 mg, 0.086 mmol), EDCI*HCl (21 mg, 0.11 mmol), and DMAP (cat. amount) were suspended in dry DCM (0.6 mL) and were shaken at RT for 15 min. Afterwards 8c (30 mg, 0.072 mmol) was added and the mixture was shaken at room temperature overnight. DCM was added and the mixture was washed with sodium bicarbonate solution and brine, dried ($Na_2SO_4$), and concentrated to dryness.

The crude product was purified by column chromatography (first column, eluent: acetone+1% TEA; second column, eluent: acetone\cyclohexane 2:1+1% TEA). Yield 5 mg.

Example 47

Synthesis of Compound 47

6-Bromohexanoic acid (224 mg, 1.15 mmol), EDCI*HCl (331 mg, 1.15 mmol), and DMAP (cat. amounts) were suspended in dry DCM (6 mL) and stirred at room temperature for 10 min. Afterwards 8x (444 mg, 1.15 mol) was added in one portion and the mixture was stirred at room temperature for 15 min.

The reaction mixture was stored at 4° C. overnight.

DCM was added and the mixture was washed with sodium bicarbonate solution (2×) and brine (1×), dried ($Na_2SO_4$) and concentrated to dryness. (540 mg of crude product).

Example 48

Synthesis of Compound 48

15 (261 mg, 0.355 mmol) and 47 (200 mg, 0.355 mmol crude product), and pyridine (32 µL, 0.39 mmol) were dissolved in 1,4-dioxane (20 mL) and heated to 80° C. overnight. Additional pyridine was added (32 µL) and the mixture heated to reflux for another 24 h. Once again, pyridine was added (32 µL) and the mixture heated to reflux for another 24 h. Then additional pyridine was added (32 µL) and heating was continued for another 24 h. The mixture was cooled to room temperature and kept at room temperature for 5 days. EtOAc and water were added and after extraction the aqueous phase was extracted with EtOAc two more times. The combined organic phases were dried ($Na_2SO_4$) and concentrated to dryness to yield 270 mg of the crude product.

Example 49

Synthesis of 49

Synthesis of [5-Amino-1-(4-fluoro-phenyl)-1H-pyrazol-4-yl]-[3-(2,3-dihydroxy-propoxy)-phenyl]-methanone (49)

a) Synthesis of 3-(3-Methoxy-phenyl)-3-oxo-propionitrile 42 g of 2-methoxybenzoic acid methyl ester and 10.4 g of acetonitril were dissolved in 300 ml of THF, and 28 g of potassium tert.-butylate were added with vigorous stirring. The mixture warmed up, and stirring was continued as good as possible. A precipitate was formed, that was filtered off after 3 h and washed with diethyl ether. After drying, the solid was dissolved in ca. 200 ml of water, and the pH was adjusted to 5-6 with formic acid. The precipitate was collected, washed with water and dried to yield 29 g.

b) Synthesis of 2-(3-Methoxy-benzoyl)-3-phenylamino-acrylonitrile 12.7 g of the product of a) and 14.35 g of Diphenylformamidine were suspended under and argon atmosphere in 100 ml of p-xylene and heated to reflux for 3 h. After cooling, the mixture was made up to 600 ml with diethyl ether. The precipitate was filtered off, washed with diethyl ether (3×) and dried to yield 13 g.

c) Synthesis of [5-Amino-1-(4-fluoro-phenyl)-1H-pyrazol-4-yl]-(3-methoxy-phenyl)-methanone 10.96 g of the product of b), 6.97 g of 4-fluoro phenylhydrazine hydrochloride, and 6.2 ml of triethylamine were combined with 140 ml of ethanol, and heated under an argon atmosphere to reflux for 5 h. After cooling, 150 ml of cyclohexane were added, and the mixture was liquified by vigorous shaking. The precipitate was filtered off, and washed with diethyl ether. After drying, 5.5 g of an off white solid remained.

d) Synthesis of [5-Amino-1-(4-fluoro-phenyl)-1H-pyrazol-4-yl]-(3-hydroxy-phenyl)-methanone 2.62 g of the product of c) were dissolved with warming to 65° C. in 10 ml of 33% HBr in glacial acetic acid and kept at this temperature for 24 h. After cooling, 100 ml of water were added, and the precipitate was collected. The solid was dissolved in 7 M ammonia in methanol and stirred, until MS indicated complete deacetylation ($[M+H]^+$=340->298). All volatiles were evaporated, and the product was redissolved in boiling methanol, poured into dil. aqueous formic acid, and collected by filtration, washed with water and dried to yield 2.3 g.

e) Synthesis of [5-Amino-1-(4-fluoro-phenyl)-1H-pyrazol-4-yl]-[3-(2,3-dihydroxy-propoxy)-phenyl]-methanone (49)

2.22 g of the product of d) are dissolved in 25 ml of dimethylformamide. 3.5 g of potassium carbonate (excess) and 580 mg of glycidol are added. The mixture is kept stirring at 60° C. for 18 h. The reaction mixture is partitioned between water and ethyl acetate. The organic phase is washed with water, dried with sodium sulfate, and concentrated i.v. The residue is subjected to prep. HPLC (methanol gradient in water, 0.05% HCOOH) to yield 1.9 g (70%) of the product.

The chiral forms (R)-49 and (S)-49 can be obtained in the same way by applying the respective enantiomer of glycidol.

Example 50

Synthesis of 50

336 mg of 44 (example 44) was taken up in THF and cooled to 0° C. To this was added 133 mg of 1,1'-Carbonyldiimidazole neat and stirred at 0° C. for 30 min. To the solution was added 177 mg of Pamapimod (6-(2,4-Difluoro-phenoxy)-2-[3-hydroxy-1-(2-hydroxy-ethyl)-propylamino]-8-methyl-8H-pyrido[2,3-d]pyrimidin-7-one; U.S. Pat. No. 6,965,030 or U.S. Pat. No. 7,320,987) and 82 mL of N,N-diisopropylethylamine simultaneously. The yellow suspension was stirred at 0° C. slowly warming to room temperature where it was stirred for 48 h. At this point, 70 mg of N-(3-Dimethylaminopropyl)-N'-ethylcarbodiimide was added and allowed to stir overnight. The solvent was removed in vacuo and the residue taken up in 50 mL of dichloromethane. The solution was extracted with 5% aqueous citric acid (3×50 mL). The combined citric acid extracts were diluted with 100 mL dichloromethane and with vigorous stirring neutralized to pH 8 with solid $K_2CO_3$. The layers were separated and the aqueous phase was extracted further with dichloromethane (3×50 mL). The combined organic phases were washed with brine and dried (Na2SO4). The solvent was evaporated in vacuo to get 271 mg of an off-white solid crude product.

Column Chromatography (1:1 Acetone/Cyclohexane with 1% triethylamine) provided 22 mg of pure 50 (5% unoptimized yield)

Example 51

Synthesis of 51

Compound 44 (300 mg, 0.36 mmol), EDCI*HCl (92 mg, 0.48 mmol), and DMAP (cat. amount) were suspended in dry DCM (3 mL) and were stirred at RT for 10 min. Afterwards 8u (89 mg, 0.24 mmol) was added and the mixture was stirred at room temperature for 90 min. The mixture was kept then in the fridge for one week. DCM was added and the mixture was washed with sodiumbicarbonate solution (2×) and brine (1×). The organic phase was dried ($NaSO_4$), concentrated to dryness and purified by column chromatography (eluent: 1% triethylamin in acetone) to yield 140 mg (47%) of 51.

Example 52

Synthesis of 52

Compound 44 (300 mg, 0.36 mmol), EDCI*HCl (92 mg, 0.48 mmol), and DMAP (cat. amount) were suspended in dry DCM (3 mL) and were stirred at RT for 10 min. Afterwards 8y (100 mg, 0.24 mmol) was added and the mixture was stirred at room temperature for 90 min. The mixture was kept then in the fridge for one week. DCM was added and the mixture was washed with sodiumbicarbonate solution (2×) and brine (1×). The organic phase was dried ($NaSO_4$), concentrated to dryness and purified by column chromatography (eluent: 1% triethylamin in acetone) to yield 100 mg (33%) of 52.

Example 53

Synthesis of 53

Compound 7b (1 g; 2.7 mmol) was taken up in methanol 50 mL). To this was added (2-Bromo-ethoxy)-tert-butyl-dimethyl-silane (800 mg; 3.3 mmol; 1.2 eq.) and KOtBu (358 mg; 3.2 mmol; 1.2 eq.) successively. The reaction mixture was heated under reflux for 2.5 h. Reaction was partitioned between ethyl acetate/$H_2O$ (50 mL/50 mL). The aqueous phase was extracted with ethyl acetate (2×50 mL). The combined organics were washed with brine, dried ($Na_2SO_4$) and evaporated in vacuo to get C as a dark brown solid (1.2 g). Column Chromatography (5% methanol in dichloromethane) produced pure 53 as an off white solid (155 mg; 11% yield).

Example 54

Synthesis of 54

Compound 7c (200 mg, 0.058 mmol) and KOtBu (78 mg, 0.70 mmol) were suspended in dry MeOH (8.0 mL) under argon atmosphere at RT. (2-Bromo-ethoxy)-tert-butyl-dimethyl-silane (180 mg, 0.75 mmol) in dry MeOH (2 mL) was added and the mixture was heated to reflux for 1 h. Afterwards the reaction mixture was allowed to cool down to RT, EtOAc and $H_2O$ were added and the mixture was stirred at RT overnight. After extraction and separation of phases the aqueous layer was extracted with EtOAc once more, the combined organic phases were dried ($Na_2SO_4$), concentrated to dryness, and purified by column chromatography (eluent: 5% MeOH in $CHCl_3$) to yield 70 mg of 54 as colorless oil Example 55

Synthesis of 55

Compound 53 (155 mg; 0.3 mmol) was dissolved in tetrahydrofuran (2 mL) and methanol (1 mL). Oxone® (119 mg; 0.2 mmol; 0.6 eq) was dissolved in $H_2O$ (1 mL) and transferred to the reaction solution all at once. Reaction was stirred at RT for 1.5 h at which point TLC (5% methanol in dichloromethane) shows no more starting material. Reaction was diluted with dichloromethane and washed with $H_2O$. The organic layer was dried ($Na_2SO_4$) and evaporated in vacuo producing 55 as a yellow solid (112 mg) which was carried out for the next step without further purification.

Example 56

Synthesis of 56

Compound 54 (85 mg, 0.17 mmol) was dissolved in a mixture of THF (1.0 mL) and $H_2O$ (0.6 mL) and cooled to 0° C. At this temperature Oxone® (61 mg, 0.10 mmol) dissolved in $H_2O$ (1.0 mL) was added in one portion. The mixture was stirred at 0° C. for 5 min, allowed to warm to RT and stirred for 1 h. EtOAc and $H_2O$ were added; after extraction aqueous phase was extracted with EtOAc once more, combined organic layers were washed with sodium bicarbonate (1×) and brine (1×), dried ($Na_2SO_4$), and concentrated to dryness to yield 56 (90 mg) as a yellow oil.

Example 57

Synthesis of 57

Compound 55 (112 mg; 0.2 mmol) was taken up in THF (2 mL) and cooled to 0° C. To this was added TBAF (1.0 M in THF, 0.23 mL; 0.2 mmol; 1.1 eq.). The reaction was stirred at 0° C. for 30 min which was then progressively warmed to RT where it was stirred overnight. Reaction was diluted with dichloromethane (50 mL) and washed with $H_2O$ (2×), brine (1×), dried (Na2SO4) and evaporated in vacuo to produce 57 as yellow oil. Column Chromatography (5% MeOH in DCM to 10% MeOH in DCM) produced 57 as an off white solid (64 mg: 73%)

Example 58 p-38α Enzyme Inhibition Assay

First the microtiter plates were coated using a dilution of ATF-2, substrate of p38α. Each step was followed by a threefold washing step. As the substrate doesn't cover the whole surface, blocking buffer was used to capture the free binding sites. In the meantime, the test compounds were diluted using the kinase buffer, which contains ATP [100 μM], phosphatase-inhibitors and the activated p38α.

The different dilutions of the test compounds were pipetted on the plate. ATP and the compounds compete for the enzyme's binding site. During an incubation time of 60 minutes ATF-2 was dual phosphorylated at Thr 69/71 by p38α kinase depending on its degree of inhibition. Next the first antibody was added into the wells. This antibody binds specifically at dual phosphorylated ATF-2 (Thr 69/71). Secondary antibody, that was conjugated with alcalic phosphatase, binds at the first one. Finally 4-NPP was given in the wells and after an incubation under cover of darkness it was photometrically analysed (405 nm).

Example 59

Effect of Compounds on Cytokine Production by Macrophage

Peritoneal macrophage or splenocytes (lymphocytes and macrophage) were harvested from donor mice using standard techniques. Cells were placed in culture and stimulated with either LPS (10 μg/mL) or concanavalin A 5 μg/mL (Sigma Chemical Co., St Louis, Mo.) in RPMI-1640 medium supplemented with antibiotics, 5×10-1 M 2-mercaptoethanol, 10 mm HEPES buffer and 10% fetal calf serum (FCS) (see Holan et al., 1985) to stimulate macrophage and T-cells respectively. Compounds were added from DMSO stock solutions to a final concentration of 50 μM or less with DMSO not exceeding 1% of total volume. After 72 h, cell supernatant was recovered and the cytokine levels were estimated by ELISA. The effect of compounds on cytokine production was recorded as follows:

TABLE 54.1

Effect of compounds on Cytokine production

| Compound/Example | NO (LPS, Macrophages) | IL-6 (LPS, Macrophages) | IL-10 (LPS, Macrophages) | IL-2 (ConA, T cells) | IFN-g (ConA, T cells) | IL-10 (ConA, T cells) | IL-1β (Macrophages, LPS) | IL-4 (Con A, spleen) | Proliferation (Con A, T cells) | Proliferation (LPS, B cells) |
|---|---|---|---|---|---|---|---|---|---|---|
| | 10 | 10 | 10 | 10 | 10 | 10 | 5 | 5 | 10 | 10 |
| | | | | Amount of cytokine, % of control treated with solvent alone | | | | | | |
| 16 | 63 | 85 | | | 2 | | | | 0 | |
| 18 | 47 | 90 | | | 2 | | | | 1 | |
| 16 | | | | | | | 85 | | | |
| 18 | | | | | | | 104 | | | |
| 18 | | | | | | | 81 | | | |
| 16 | | | | | | | 85 | | | |
| DMSO | | | | | | | 87 | | | |
| 18 | 54 | 109 | 110 | 52 | 16 | 38 | 81 | 91 | 19 | 2 |
| 18 | 65 | 106 | 108 | 86 | 65 | 70 | 70 | 84 | 67 | 22 |
| 22 | 69 | 116 | 13 | 29 | 41 | 144 | 90 | 237 | 10 | -2 |
| 21 | -19 | 101 | -8 | 0 | 0 | 0 | 101 | 320 | 0 | -4 |
| 21 | 5 | 101 | -18 | 7 | 0 | 23 | | | 6 | -3 |
| 22 | | | | | | | 106 | 407 | 10 | -12 |
| 21 | | | | | | | 143 | 0 | -1 | -12 |
| 20 | | | | | | | 34 | -5 | 0 | -1 |
| 43g | | | | | | | 28 | 125 | 3 | -1 |
| 77 | | | | | | | | 332 | | |
| 49 | | | | | | | | 188 | | |
| 43h | | | | | | | | 280 | | |
| 43i | | | | | | | | 8 | | |
| 23 | 22 | 59 | 11 | 6 | 11 | 2 | | | 3 | 3 |
| 43a | 1 | 15 | 2 | 0 | 3 | 0 | | | 0 | 2 |
| 43i | 4 | 33 | 3 | 2 | 5 | 3 | | | 0 | 1 |
| 43i | 0 | 32 | -4 | 0 | 2 | -2 | | | -1 | -3 |
| 43b | 31 | 94 | -4 | 0 | 0 | -2 | | | -2 | -3 |
| 43c | 82 | 95 | 7 | 90 | 72 | 25 | | | 113 | 2 |
| 43d | 52 | 95 | -4 | 0 | 3 | -2 | | | -2 | -3 |
| 43e | 1 | 29 | -4 | 0 | 0 | -2 | | | -1 | -3 |
| 43f | 2 | 30 | -10 | -1 | 61 | 0 | | | -8 | -6 |
| 36 | 100 | 91 | 116 | 96 | 99 | 79 | | | 199 | 3 |
| 35 | 76 | 93 | 114 | 99 | 104 | 112 | | | 244 | -2 |
| 39 | 74 | 92 | 63 | 66 | 32 | 90 | | | 129 | -4 |
| 43k | -1 | 22 | -8 | 0 | 0 | 0 | | | -1 | -8 |
| 39 | 91 | 108 | 106 | 93 | 76 | 129 | | | 113 | 33 |
| 43n | -1 | 17 | -9 | 0 | 0 | 0 | | | -1 | -6 |

TABLE 54.2

Effect of compounds on IL-10 production by murine peritoneal macrophage at different concentrations Concentration of inhibitor in medium (µM): IL-10 by ELISA, % of solvent treated control

| Example # | 50 | 20 | 10 | 5 | 2 | 1.25 | 1 | 0.31 |
|---|---|---|---|---|---|---|---|---|
| 16 |  | 8 | 99 |  |  |  | 117 |  |
| 18 |  | 57 | 109 | 109 |  |  | 124 |  |
| 20 |  | -12 | -12 | -11 |  |  |  |  |
| 21 |  | -8 | -13 | 1 |  |  | 95 | 132 |
| 22 |  | -3 | 13 | 43 |  |  | 86 | 103 |
| 23 | 4 |  | 11 | 56 |  |  |  |  |
| 27 |  | 17 | 106 | 132 |  |  |  |  |
| 29 |  | 106 | 114 | 110 |  |  |  |  |
| 35 | 16 |  | 114 | 42 |  |  |  |  |
| 36 | 0 |  | 116 | 88 |  |  |  |  |
| 39 | 0 |  | 63 | 58 |  |  |  |  |
| 49 |  | 13 |  | 42 |  |  | 41 |  |
| 43a | 5 |  | 2 | 16 |  |  |  |  |
| 43b | -4 |  | -4 | 27 |  |  |  |  |
| 43c | -4 |  | 7 | 18 |  |  |  |  |
| 43d | -4 |  | -4 | 15 |  |  |  |  |
| 43e | -4 |  | -4 | -4 |  |  |  |  |
| 43f | 27 |  | -10 | -1 |  |  |  |  |
| 43g |  | -12 |  | -12 |  |  | 26 |  |
| 43h |  | -11 |  | 52 |  |  | 68 |  |
| 43i | 0 |  | 3 | 25 |  |  |  |  |
| 43j |  |  |  |  |  |  |  |  |
| 43k | -9 |  | -8 | -6 |  |  |  |  |
| 43m | -5 |  | 38 | 17 |  |  |  |  |
| 43n | -9 |  | -9 | -5 |  |  |  |  |

A similar experiment can be performed using Bone marrow derived macrophage or Tumour associated macrophage (TAM): Mouse macrophages were derived from the bone marrow of WT, C57BL/6 mice and cultured for 7 d in DMEM medium supplemented with 10 ng/ml recombinant mouse M-CSF (R & D Systems). TAMs were isolated from the peritoneal cavity of mice in which IDB ovarian cancers had been growing i.p. for up to 10 wk. The macrophage are then treated with the compound to test at 1 or 10 µM in the presence of a stimulant such as LPS or TNFa or tumour conditioned medium. Under these conditions compound 43 J inhibits the production of IL-10 and compound 49 stimulates the production of IL-12.

Example 60

Effect of Compounds on the Production of Il-12 In Vivo. The Effect of Pamapimod or Compound 49 on Plasma IL-12 Levels in Response to Stimulation with Recombinant Human TNFα

Three groups of male SJL mice, 6 weeks old, were fasted for 4 hours prior to the experiment. Group 1 was treated p.o. with pamapimod or compound 49 at 15 mmoles/kg body weight in 2% citric acid, groups 2 and 3 were given only 2% citric acid p.o. All treatments were applied at 5 ml/kg body weight. After 30 min each mouse in groups 1 and 2 were stimulated with an i.p. injection of 4 µg of recombinant human TNFα in 100 µl sterile saline. The control mice of group 3 were injected i.p. with 100 µl saline. At 1.5 h, 3 h, and 6 h, after the stimulation with hTNFα blood samples were taken from each mouse via the tail vein and the plasma was analyzed for cytokine levels by ELISA. Stimulation with recombinant hTNFα increased the IL-12 plasma levels of vehicle treated animals slightly compared to unstimulated animals at all monitored time points. The oral treatment with pamapimod prior to stimulation with hTNFα increases this response by 2 to 3 times over vehicle treatment at 3 h and 6 h after hTNFα injection (see FIG. 1).

Example 61

Treatment of Cancer by Lewis Lung Carcinoma Cells or Cancer of the Pancreas

Figure 2:
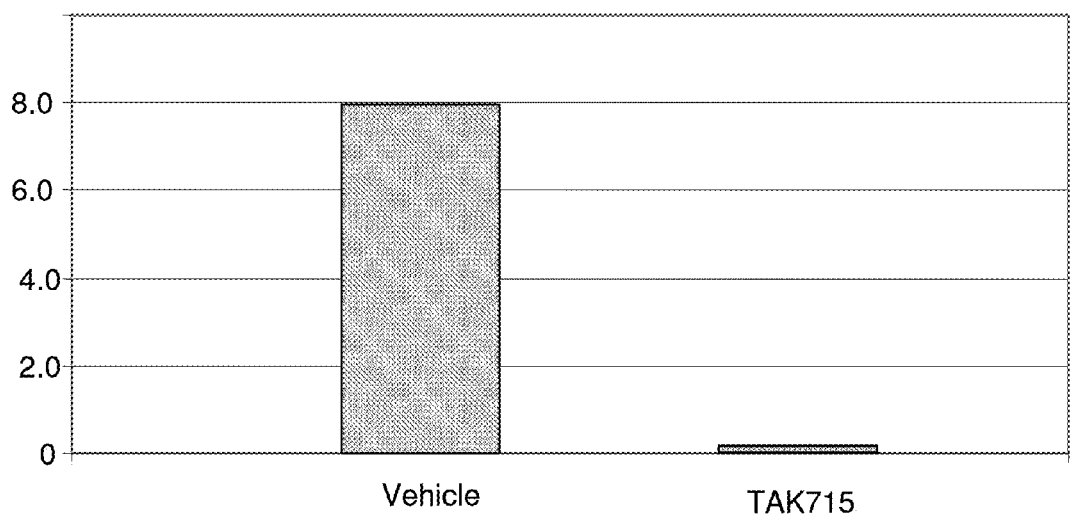
FIG. 2 Tumour size in mice bearing a subcutaneous tumour derived from LLC cells as determined at 24 days after initiation.
Figure 3:
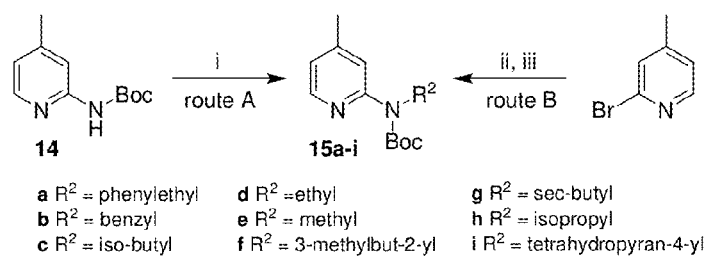
FIG. 3 Reaction scheme for synthesis of precursors of p38 inhibitors
Figure 4:
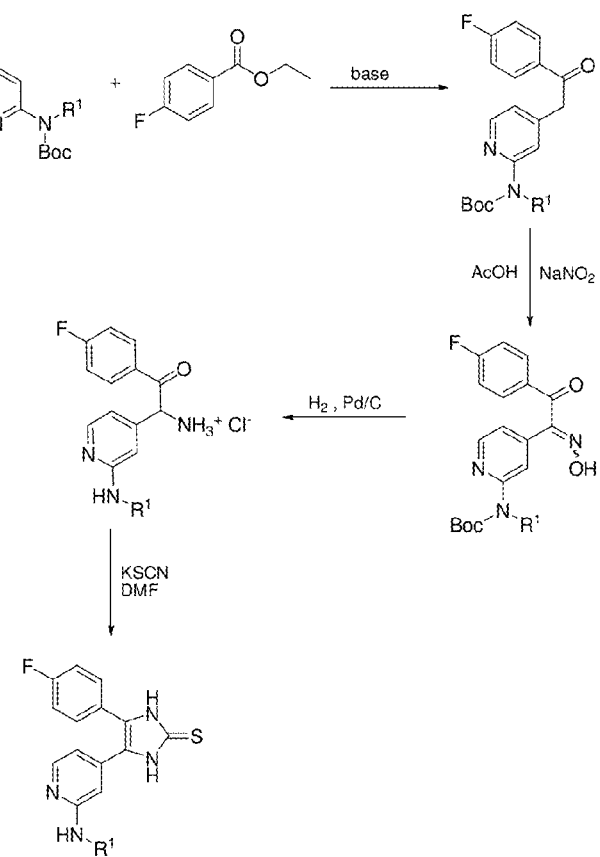
FIG. 4 Reaction scheme for formation of p38 inhibitor precursor.
Figure 5:
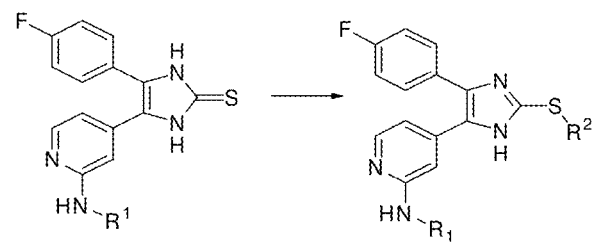
FIG. 5 Conversion of S— substituents of p38 inhibitors
Figure 6:
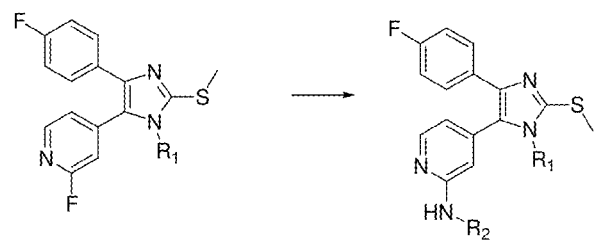
FIG. 6 Insertion of amino functionality in a p38 inhibitor

Lewis Lung Carcinoma Cells (LLC) are cultured by incubation in a medium which is RPMI 1640 (50%) and DMEM (50%) with a final concentration or fetal calf serum of 10%. After culture to the log phase, $10^5$ cells are injected subcutaneously in C57BLK6 mice. Mice are treated with substance either orally or via intraperitoneal injection. Treatment with the substance TAK-715 at a dose of 12.5 mg/kg p.o. in a vehicle (0.5% Tween 80, 0.5% Hypremellose, 10% PEG 300) once daily results in a reduction in the growth rate of the LLC tumour example data for which are provided in FIG. 2.

For treatment of pancreatic cancer, mice susceptible to pancreatic cancer were observed until cancer was apparent. Thereafter, animals were classified by ultrasound to a group of similar tumour size and were allocated to treatments: Vehicle, Gemcitabine 100 mg/kg every $5^{th}$ day, or Gemcitabine plus the IL-10 inhibitor 43j (10 mmol/kg/d i.p.), or the IL-12 stimulant 49 (10 µmol/kg/day i.p.) or all three combined at the doses specified. The combination of all 3 substances was significantly more protective than the gemcitabine alone providing ca. 3-fold the survival time of the vehicle vs. 1.5 fold for gemcitabine alone, the combinations of gemcitabine and the substances 43j or 49 resulted in an increase in survival of greater than 1.5-fold that of gemcitabine alone.

Example 62

Tumor Challenge—EG.7-OVA Model for Combination Therapeutic Vaccination with Disactivation of Tumoural Immune Suppression EG.7-OVA is a cell line generated from EL-4, a thymoma cell line derived from a C57BL/6 mouse (H-2b) transfected with chicken ovalbumin cDNA (Moore et al., Cell 1988, 54:777-785). The cells were maintained in RPMI 1640 containing 5% FCS, penicillin (100 U/ml), and streptomycin (100 µg/ml). Annexin V-labelled, apoptotic lymphoma cells have been successfully used as an anti-tumor vaccine in mice (Bondanza et al., J Exp Med. 2004 Nov. 1; 200(9): 1157-65). In order to retrieve tumor material used for such an immunotherapeutic approach, C57BL/6 mice were injected subcutaneously with 1×106 EG.7-OVA cells each. After 21 days tumors were harvested, treated with collagenase and homogenized. The tumor cell suspension was then irradiated at 30 Gy to render apoptotic cells, which are then labelled with Annexin V.

Combined Immunotherapy

In order to test the effect of 49 and 43j on the outcome of immunotherapy using Annexin V labelled, apoptotic lymphoma cells, three groups of mice were challenged as follows: female C57BL/6 mice, 8 weeks old, were injected subcutaneously with 1×106 EG.7-OVA cells each. At 7 days and 14 days after the challenge two groups of mice received subcutaneous injections of irradiated Annexin V labelled lymphoma cells, one of the groups received i.p. injection of 49 and 43j. The third group (control group) received an injection of only saline. The following parameters will be measured: disease-free time in days, tumor size (in mm3) at day 21 after tumor induction, and survival time up to 28 days after challenge.

Combined Immunotherapy

In order to assess the ability of 49 and 43j on improving the outcome of chemotherapy, three groups of mice were injected subcutaneously with 1×106 EG.7-OVA cells per animal. The mice of 2 groups received chemotherapy with gemcitabine as soon as tumors were visible. The mice of one of the two groups received intraperitoneal injections of 49 and 43j. The third group (control group) received the vehicle used to suspend the substance. The following parameters were measured: disease-free time in days, tumor size (in mm3) after tumor induction, and survival time.

Example 63

Tumor Challenge—B16 Melanoma Model for Effects of Anti-Tumour Compounds

Figure 11:
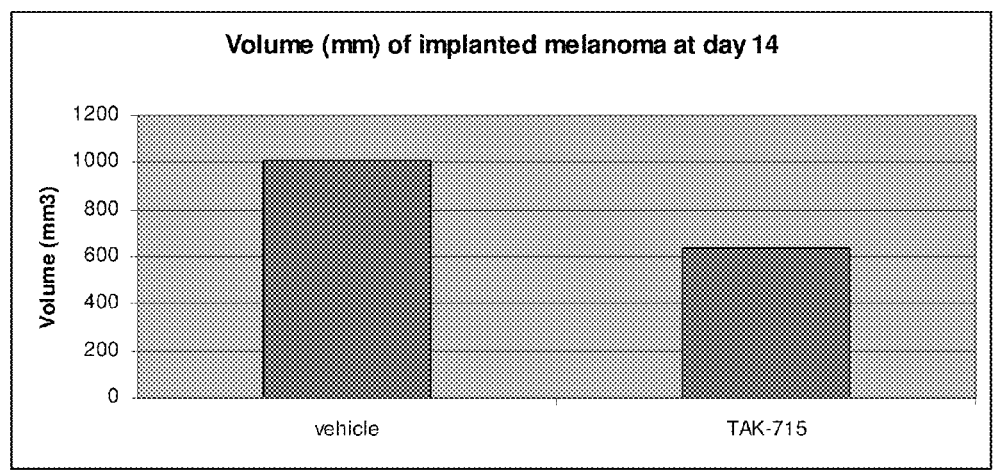

B16 Melanoma cells were maintained as for LLC cells and injected into mice (see Example 61). Mice carrying tumours on the right flank were selected when the tumour was first palpable and the animals allocated to groups treated with either Vehicle, Gemcitabine alone, Compound 49, Compound 43j or the Compound TAK-715 at 10 μmol/kg/day i.p. in saline containing 0.02% citric acid. The effects of the combined treatment are reported in FIG. 11.

Example 64

Tumor Challenge—MB49 Bladder Cancer Model for Effects of Anti-Tumour Compounds

Figure 10:
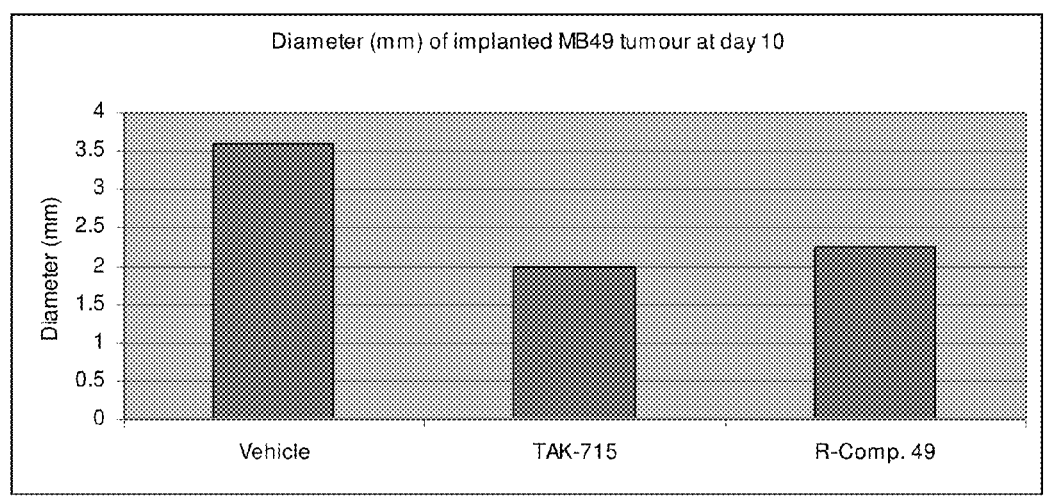

MB49 cells were maintained and injected into mice as in Example 61. Mice carrying tumours on the right flank were selected when the tumour was first palpable and the animals allocated to groups treated with either Vehicle, the R-isomer of Compound 49, or the Compound TAK-715 at 10 μmol/kg/day i.p. in saline containing 0.02% citric acid. The effects of the combined treatment are reported in FIG. 10.

Example 65

Tumor Challenge—EG.7-OVA Model for Combination Effects of Anti-Tumour Compounds

Figure 12:
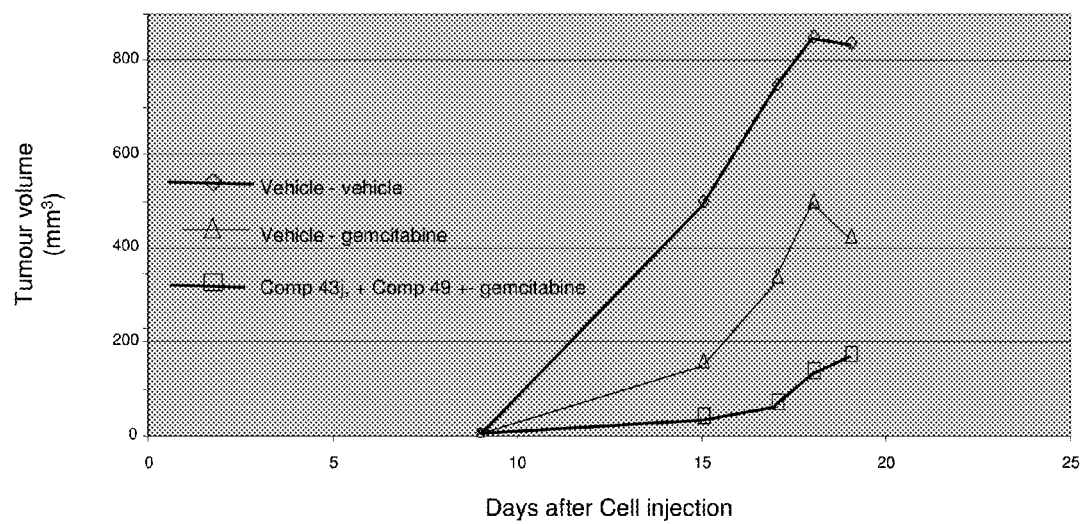

EG.7-OVA was maintained and injected into mice as in Example 61. Mice carrying tumours on the right flank were selected when the tumour was first palpable and the animals allocated to groups treated with either Vehicle, Gemcitabine alone, or the combination of 49 and 43j. Compounds were supplied daily i.p. at 10 mmol/kg. The effects of the combined treatment are reported in FIG. 12.

Example 66

Tumor Challenge—Murine Pancreatic Cancer—Changes in Cytokine Expression

Murine pancreatic cancer was induced as in Example 61. Mice carrying tumours were selected when the tumour was first detectable by ultrasound and the animals allocated to groups treated with either Vehicle, 49 alone or 43J alone or the combination of 49 and 43j. Compounds were supplied daily i.p. at 10 μmol/kg. The effects of the combined treatment on the relative levels of gene expression in the tumours are reported in the following table. Gene expression as determined by mRNA levels is determined by real time PCR methods using reverse transcribed templates.

| Cytokine | Treatment | Relative Gene expression |
|---|---|---|
| IFNg | Vehicle | 1.0 |
|  | 43J | 4.2 |
|  | 49 | 6.3 |
|  | 43J + 49 | 7.8 |

-continued

| Cytokine | Treatment | Relative Gene expression |
|---|---|---|
| IL-10 | Vehicle | 21.4 |
|  | 43J | 3.1 |
|  | 49 | 8.9 |
|  | 43J + 49 | 2.1 |
| IL-12 | Vehicle | 3.1 |
|  | 43J | 3.4 |
|  | 49 | 28.8 |
|  | 43J + 49 | 69.5 |
| IL-23 | Vehicle | 15.2 |
|  | 43J | 11.0 |
|  | 49 | 2.1 |
|  | 43J + 49 | 3.1 |
| IL-17 | Vehicle | 17.8 |
|  | 43J | 14.6 |
|  | 49 | 15.2 |
|  | 43J + 49 | 11.0 |
| IL-6 | Vehicle | 22.5 |
|  | 43J | 15.2 |
|  | 49 | 18.3 |
|  | 43J + 49 | 13.1 |
| TNFa | Vehicle | 15.2 |
|  | 43J | 13.1 |
|  | 49 | 21.4 |
|  | 43J + 49 | 22.5 |

Example 67

Synthesis of [5-Amino-1-(4-fluoro-phenyl)-1H-pyrazol-4-yl]-[3-(2-ethanesulfinyl-ethoxy)-phenyl]-methanone (67c) and [5-Amino-1-(4-fluoro-phenyl)-1H-pyrazol-4-yl]-[3-(2-ethanesulfonyl-ethoxy)-phenyl]-methanone (67d)

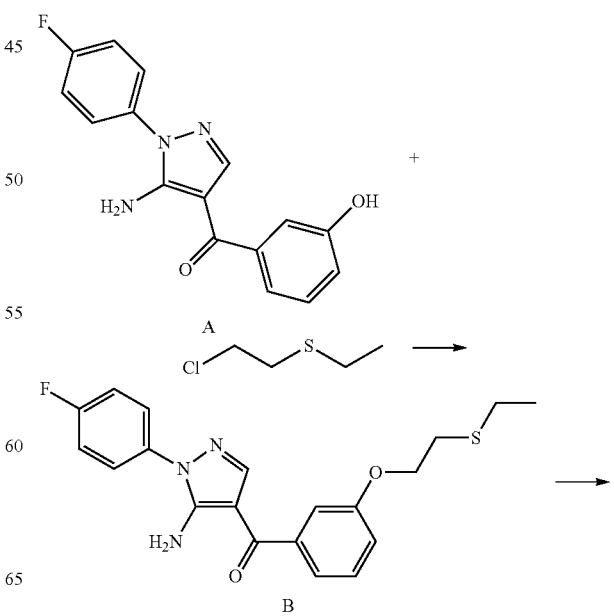

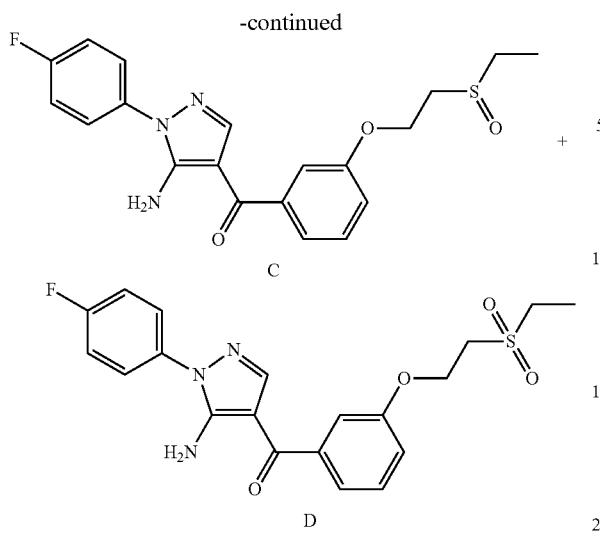

Compound A (example 49d) (200 mg; 0.7 mmol), 1-Chloro-2-ethylsulfanyl-ethane (86 µL; 0.8 mmol), K₂CO₃ (103 mg; 0.8 mmol) were mixed together in a reaction vessel and diluted with methanol. The reaction was heated to reflux. After 2 h, reaction was complete as monitored by TLC (5% methanol in DCM). The solvent was removed in vacuo and the residue suspended between ethyl acetate and H₂O. The organic phase was washed with water and brine. The organic phase was dried (Na₂SO₄) and evaporated in vacuo to get B as a yellow solid (212 mg) that was directly used for the successive steps without purification.

Compound B (212 mg; 0.6 mmol) was dissolved in THF (4 mL) and methanol (2 mL). Oxone (203 mg; 0.4 mmol) was dissolved in H₂O (2 mL) and transferred to the reaction solution all at once. Reaction was stirred at room temperature for 2 h at which point TLC (5% methanol in DCM) shows no more starting material. Reaction was diluted with dichloromethane and washed with H₂O. The organic layer was dried (Na₂SO₄) and evaporated in vacuo producing C and D as a light brown solid (224 mg). Column Chromatography (2% methanol in DCM, increasing methanol concentration to 10%) produced C (65 mg) and D (73 mg) both as off-white solid.

Example 68

Synthesis of {3-[5-Amino-1-(4-fluoro-phenyl)-1H-pyrazole-4-carbonyl]-phenoxy}-acetic acid methyl ester (68)

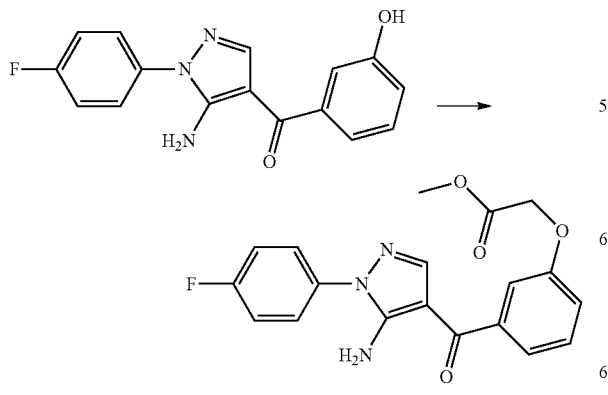

3 g of [5-Amino-1-(4-fluoro-phenyl)-1H-pyrazol-4-yl]-(3-hydroxy-phenyl)-methanone (example 49d) and 1.4 ml of bromoacetic acid methyl ester were dissolved in 25 ml of Methanol. 1.79 g of K₂CO₃ were added, and the mixture was heated to reflux over night. When MS indicated completion of the reaction, the mixture was concentrated i.v., and the residue was partitioned between water and chloroform (200 ml each). The organic phase was washed with water and brine, dried over Na2SO4, and concentrated. The residue was recrystallised from EtOAc to yield 3 g of the target compound.

Example 69

Synthesis of 2-{3-[5-Amino-1-(4-fluoro-phenyl)-1H-pyrazole-4-carbonyl]-phenoxy}-N-(2-hydroxy-ethyl)-N-methyl-acetamide (69)

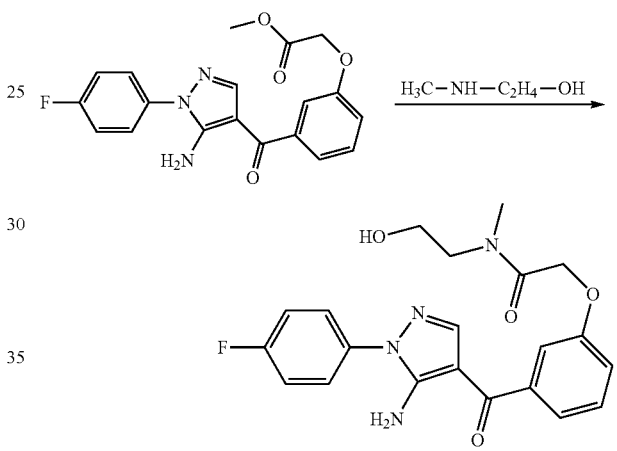

120 mg {3-[5-Amino-1-(4-fluoro-phenyl)-1H-pyrazole-4-carbonyl]-phenoxy}-acetic acid methyl ester (example 68) and 100 µl of N-methyl ethanolamine are heated in 1 ml of DMF to 95° C. for 12 h. MS indicated complete conversion. The product was precipitated from the solution with water, washed, dried and recrystallised from ethyl acetate to yield 60 mg of the target compound.

Example 70

Synthesis of 2-{3-[5-Amino-1-(4-fluoro-phenyl)-1H-pyrazole-4-carbonyl]-phenoxy}-N-(2-hydroxy-ethyl)-acetamide (70)

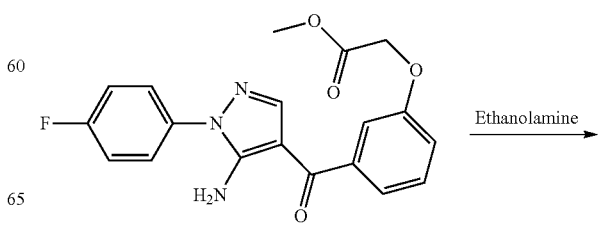

-continued

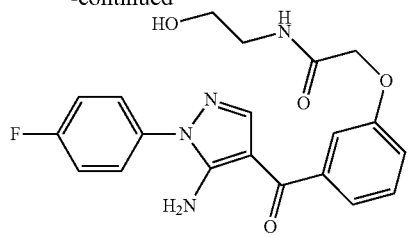

The target compound can be obtained by the same method as above (example 69) and substituting N-methyl ethanolamine with ethanolamine.

Example 71

2-{3-[5-Amino-1-(4-fluoro-phenyl)-1H-pyrazole-4-carbonyl]-phenoxy}-N-methyl-N-(3,4,5-trihydroxy-6-hydroxymethyl-tetrahydro-pyran-2-yl)-acetamide (71)

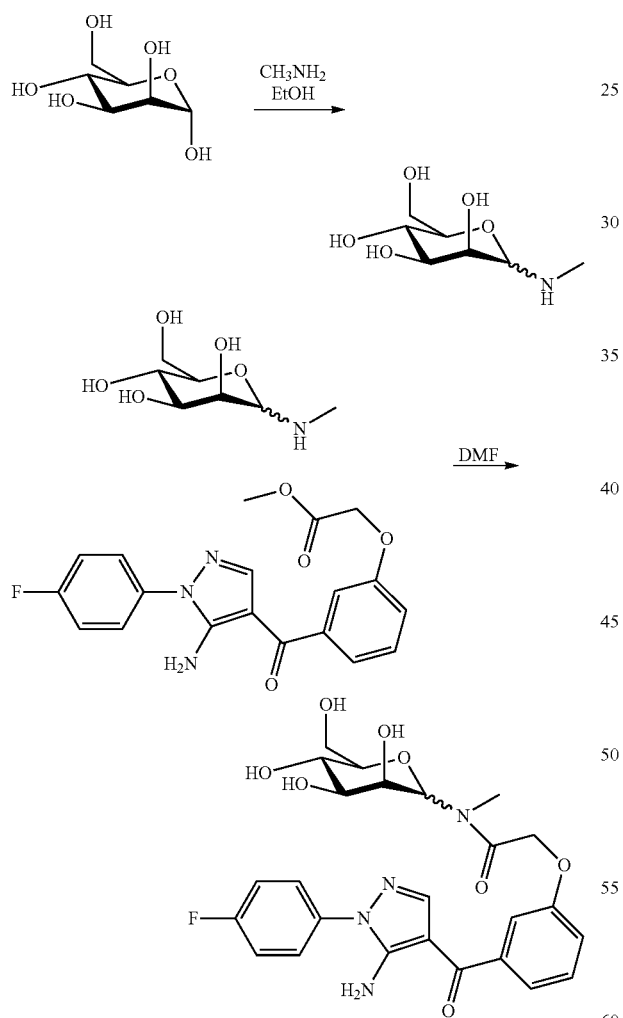

200 mg of mannose were stirred in 5 ml of an 8M solution of methylamine in ethanol. After complete solution, the mixture was stirred for 2 more h, and concentrated to dryness. The residue was suspended in 5 ml of toluene, again concentrated to dryness and then redissolved in 1 ml of DMF, and 80 mg of {3-[5-Amino-1-(4-fluoro-phenyl)-1H-pyrazole-4-carbonyl]-phenoxy}-acetic acid methyl ester (example 68) were added. After heating to 70° C. for 10 h, the product was precipitated by addition of diethylether, and chromatographed (EtOAc/EtOH=5/1) over silica gel to yield 45 mg of the target compound.

Example 72

Synthesis of [5-Amino-1-(4-fluoro-phenyl)-1H-pyrazol-4-yl]-[3-(2,2-diethoxy-ethoxy)-phenyl]-methanone (72)

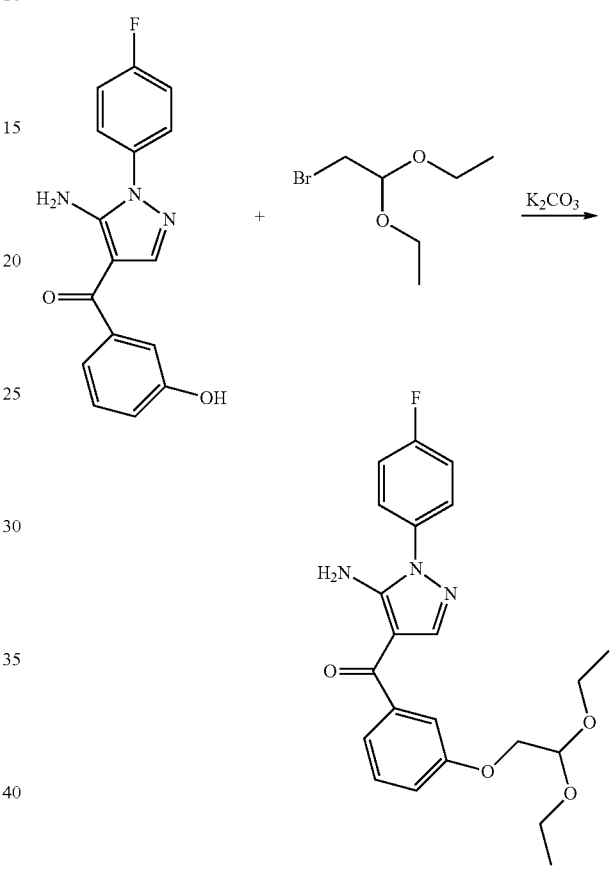

200 mg of [5-Amino-1-(4-fluoro-phenyl)-1H-pyrazol-4-yl]-(3-hydroxy-phenyl)-methanone (example 49d) and 150 µl of bromoacetaldehyde diethylacetal are combined in 5 ml of 2-propanol with 75 mg of potassium carbonate. The mixture is heated to reflux for 60 h. Concentration i.v. and chromatography yielded 65 mg of the target compound.

Example 73

Synthesis of (2-{3-[5-Amino-1-(4-fluoro-phenyl)-1H-pyrazole-4-carbonyl]-phenoxy}-acetylamino)-acetic acid (73)

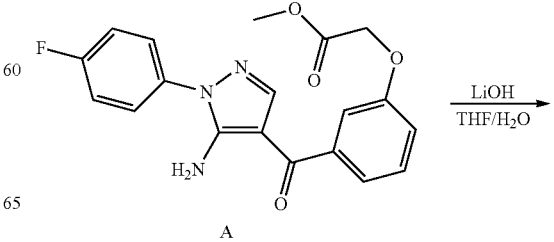

A

81
-continued

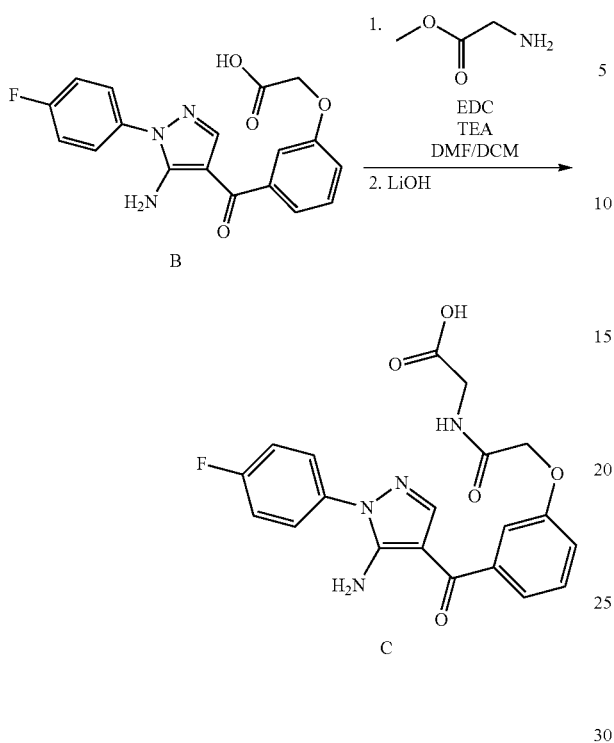

Example 74

Synthesis of [5-Amino-1-(4-fluoro-phenyl)-1H-pyrazol-4-yl]-[3-(2-hydroxy-ethoxy)-phenyl]-methanone (74)

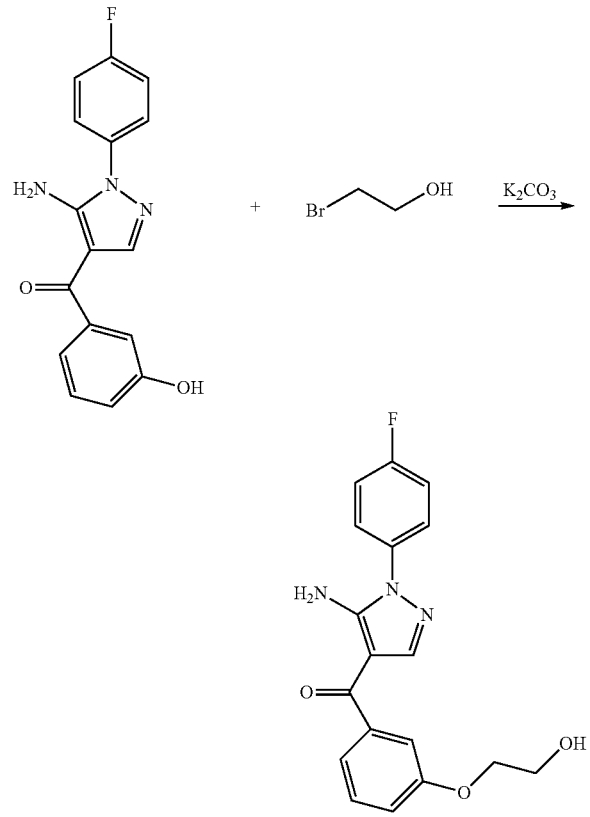

Compound A (example 68) (365 mg; 1.0 mmol) was taken up in THF (16 mL) and H$_2$O (8 mL). LiOH (125 mg; 3.0 mmol) was added all at once. Reaction was stirred at room temperature overnight, at which point reaction showed no more starting material. The reaction was concentrated in vacuo and the residue taken up in H$_2$O and pH adjusted to 4 with 10% citric acid. The precipitated solids were collected by vacuum filtration and dried producing B as a brown solid (325 mg). This was used directly for the next step without purification.

Compound F (365 mg; 1.0 mmol) was diluted with DMF (2 mL) and DCM (2 mL). To this, was added HOBt (140 mg; 1.0 mmol) and DIC (160 mL; 1.0 mmol). The reaction was stirred for 4 h. The reaction mixture was transferred to a stirred solution of Glycine methyl ester HCl (130 mg: 1.0 mmol), Et3N (145 mL; 1.0 mmol) and DCM (2 mL). The reaction was stirred for 72 h at room temperature at which point, TLC showed no more starting material. Reaction was diluted with dichloromethane (100 mL) and washed with H$_2$O (3×). The organic layer was dried (Na$_2$SO$_4$) and evaporated in vacuo producing a yellow solid. This was directly taken up in THF (16 mL) and H$_2$O (8 mL). LiOH (125 mg; 3.0 mmol) was added all at once. Reaction was stirred at room temperature overnight, at which point reaction showed no more starting material. The reaction was concentrated in vacuo and the residue taken up in H$_2$O and pH adjusted to 4 with 10% citric acid. The precipitated solids were collected by vacuum filtration and dried producing target compound C as a yellow solid (225 mg). Crystallization (EtOH/H$_2$O) produced G as an off-white solid (93 mg).

200 mg of [5-Amino-1-(4-fluoro-phenyl)-1H-pyrazol-4-yl]-(3-hydroxy-phenyl)-methanone (example 49d) and 150 μl of bromoethanol are combined in 15 ml of 2-propanol with 75 mg of potassium carbonate. The mixture is heated to reflux for 60 h. Concentration i.v. and chromatography yielded 115 mg of the target compound.

Other Embodiments

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

ABBREVIATIONS

The following abbreviations were used as noted:
MeOH: methanol
NaHCO$_3$: sodium bicarbonate
K$_2$CO$_3$: potassium carbonate MS: mass spectrometry
DMSO: dimethyl sulfoxide
TLC: thinlayer chromatography
Et$_3$N: triethylamin
EtOAc: ethyl acetate
DCM: dichloromethane
NH$_4$Cl: ammonium chloride
THF: tetrahydrofurane
Na$_2$CO$_3$: sodium carbonate
EDCI*HCl: N-Ethyl-N'-(3-dimethylaminopropyl)carbodiimide hydrochloride
DMAP: 4-dimethylamino pyridine
TBDMS tert-butylsilyl

CITATION LIST PATENT LITERATURE

US Patent Literature

U.S. Pat. No. 7,101,899, U.S. Pat. No. 6,962,933, US2006293226 US20070932125P, US2008207684, US2008146590, US2008119497, US2007167471, US2007049633, US2006252784, U.S. Pat. No. 7,517,901, U.S. Pat. No. 7,285,561, U.S. Pat. No. 6,316,466, US2004097493, U.S. Pat. No. 6,943,158, US2004209903, U.S. Pat. No. 7,189,731, US2005203091, U.S. Pat. No. 7,452,880, US2005197352 U.S. Pat. No. 7,081,462, US2006084803 U.S. Pat. No. 7,439,247, U.S. Pat. No. 6,319,92 (BIRB 796), laufer U.S. Pat. No. 6,867,211, U.S. Pat. No. 6,936,632, U.S. Pat. No. 7,253,191, US20050656389, WO2007EP58847, US20050524839, US2009306108, US2009239899 US2009270350, U.S. Pat. No. 7,629,363, US2009215817, US2009209577, U.S. Pat. No. 7,037,923, U.S. Pat. No. 7,012,143, U.S. Pat. No. 7,259,171, U.S. Pat. No. 7,005,523, U.S. Pat. No. 6,664,395, U.S. Pat. No. 6,696,464, U.S. Pat. No. 7,056,918, U.S. Pat. No. 7,314,873, U.S. Pat. No. 7,196,095, U.S. Pat. No. 6,809,199, WO03097062, U.S. Pat. No. 6,498,274, U.S. Pat. Nos. 6,686,467, 6,881,756, 7,652,044, U.S. Pat. No. 7,569,571, U.S. Pat. Nos. 6,579,874 6,300,347, U.S. Pat. No. 7,652,022, U.S. Pat. No. 7,615,562, U.S. Pat. No. 6,891,039, U.S. Pat. No. 6,608,072, U.S. Pat. No. 6,919,336, U.S. Pat. No. 6,645,990, U.S. Pat. No. 7,196,104, U.S. Pat. No. 7,504,403, U.S. Pat. No. 7,514,566, U.S. Pat. No. 6,967,254, U.S. Pat. No. 7,321,001, U.S. Pat. No. 7,541,383, U.S. Pat. No. 7,115,617, U.S. Pat. No. 7,354,944, U.S. Pat. No. 6,864,255, U.S. Pat. No. 6,881,737, U.S. Pat. No. 7,390,820, U.S. Pat. No. 7,320,992, U.S. Pat. No. 6,965,030, U.S. Pat. No. 7,320,987, U.S. Pat. No. 7,626,030, U.S. Pat. Nos. 6,939,874 7,307,088, U.S. Pat. No. 7,282,504, U.S. Pat. No. 7,105,682, U.S. Pat. No. 7,101,868, U.S. Pat. No. 6,995,162, U.S. Pat. No. 7,119,111, U.S. Pat. No. 7,507,748, U.S. Pat. Nos. 7,514,564 7,102,009, U.S. Pat. No. 7,531,553, U.S. Pat. No. 6,878,714, U.S. Pat. No. 6,921,762, U.S. Pat. No. 6,849,639, U.S. Pat. Nos. 7,541,368, 7,470,689 7,309,701, U.S. Pat. No. 7,462,613, U.S. Pat. No. 7,479,501, U.S. Pat. No. 6,770,643, U.S. Pat. No. 6,897,207, U.S. Pat. No. 7,381,841, U.S. Pat. Nos. 7,227,020 6,967,210, U.S. Pat. No. 6,528,315, U.S. Pat. No. 7,179,821, U.S. Pat. No. 7,230,015, U.S. Pat. No. 7,534,803, U.S. Pat. No. 7,309,800, U.S. Pat. No. 7,432,289, U.S. Pat. No. 7,208,629, U.S. Pat. No. 7,166,623, U.S. Pat. No. 7,396,843, U.S. Pat. No. 7,384,963, U.S. Pat. No. 7,183,297, U.S. Pat. No. 7,151,118, U.S. Pat. No. 7,166,597, U.S. Pat. No. 7,423,042, U.S. Pat. No. 7,348,339, U.S. Pat. No. 7,479,558, U.S. Pat. No. 7,612,094, U.S. Pat. No. 6,432,962, U.S. Pat. No. 7,507,734, U.S. Pat. No. 7,495,018, U.S. Pat. No. 7,101,899, U.S. Pat. No. 6,962,933.

Non-US Patent Documents

WO02/32862; WO02/060869; WO00/10563; WO00/31063; WO00/31072; WO00/39116; WO00/63204; WOO 1/30778; WO02/072571; WO03/035638; WO00/64894; WOO 1/10865; WOO 1/074811; WO02/072579; WO2004/014900; WO2004/026302; WO00/25791; WO00/40243; WO01/34605; WO02/16359; WO01/57018; WO2004/076450; WO03/024973; WO03/024971; WO01/90074; WO02/083622; WO02/076447; WO02/092087; WO03/008413; WO03/053967; WO03/076405; WO03/091229; WO01/21591; WO03/020715; WO98/27098; WO00/17204; WO00/17175; WO01/70695; WO01/37837; WO01/38312; WO01/38313; WO01/38314; WO01/64679; WO02/058695; WO03/103950; WO2004/024699; WO02/059083; WO03/088972; WO2004/073628; WO03/033502; WO2004/014920; WO2004/031188; WO00/12074; WO00/59904; WO00/71535; WO02/42292; WO02/46158; WO03/043988; WO2004/022712; WO2004/021988; WO2004/0328742; WO03/084539; WO00/41698; WO02/085859; WO03/087087; WO2004/060306; WO2004/014870; WO00/20402; WO00/07980; WO00/07991; WO00/18738; WO00/55120; WO00/55153; WO00/56738; WO01/47897; WO02/40486; WO03/002544; WO2004/0714402; WO03/032970; WO03/032971; WO03/032972; WO03/032980; WO03/032986; WO03/032987; WO03/033457; WO03/033482; WO2004/010995; WO03/033483; WO03/068747; WO03/093248; WO2006/089798, WO2008/023066, and European Patent No. 01247810.

CITATIONS

Non Patent Literature

Umansky V, Malyguine A, Shurin M. New perspectives in cancer immunotherapy and immunomonitoring. Future Oncol. 2009 September; 5(7):941-4.

Fahey L M, Raff A B, Da Silva D M, Kast W M J Immunol. 2009 Mar. 1; 182(5):2919-28. Reversal of human papillomavirus-specific T cell immune suppression through TLR agonist treatment of Langerhans cells exposed to human papillomavirus type 16.

Han Y H, Moon H J, You B R, Kim S Z, Kim S H, Park W H. p38 inhibitor intensified cell death in antimycin A-treated As4.1 juxtaglomerular cells via the enhancement of GSH depletion. Anticancer Res. 2009 November; 29(11):4423-31.

Kadowaki S, Endoh D, Okui T, Hayashi M. Trientine, a copper-chelating agent, induced apoptosis in murine fibrosarcoma cells by activation of the p38 MAPK pathway. J Vet Med Sci. 2009 November; 71(11):1541-4.

Liu S X, Zhang Y J, Guo H F, Hao J, Liu Q J, Liu J R, Guo J W, Liu J H, Zuo L F. The regulatory effect of the p38 signaling pathway on valdecoxib-induced apoptosis of the Eca109 cell line. Oncol Rep. 2009 August; 22(2):313-9.

Pascolo S Messenger RNA-based vaccines. Expert Opin Biol Ther. 2004 August; 4(8):1285-94.

Hagemann T, Lawrence T, McNeish I, Charles K A, Kulbe H, Thompson R G, Robinson S C, Balkwill F R. "Re-educating" tumor-associated macrophages by targeting NF-kappaB. J Exp Med. 2008 Jun. 9; 205(6):1261-8.

HOLAN V., LIPOLDOVA M., TAKAC M., CERNA J., VANCATOVA A., CECHOVA D., VESELSK4 L. &

HAgEK M. (1985) Establishment and characterization of a permanent T-cell line producing antigen nonspecific suppressor factor. Immunology, 56, 275.

Karin M. NF-kappaB as a critical link between inflammation and cancer. Cold Spring Harbor Perspect Biol. 2009 November; 1(5):a000141.

Ulivi V, Giannoni P, Gentili C, Cancedda R, Descalzi F. J p38/NF-kB-dependent expression of COX-2 during differentiation and inflammatory response of chondrocytes. Cell Biochem. 2008 Jul. 1; 104(4):1393-406.

Bradham C, McClay D R. p38 MAPK in development and cancer. Cell Cycle. 2006 April; 5(8):824-8. Epub 2006 Apr. 17.

Yasui H, Hideshima T, Ikeda H, Jin J, Ocio E M, Kiziltepe T, Okawa Y, Vallet S, Podar K, Ishitsuka K, Richardson P G, Pargellis C, Moss N, Raje N, Anderson KC.BIRB 796 enhances cytotoxicity triggered by bortezomib, heat shock protein (Hsp) 90 inhibitor, and dexamethasone via inhibition of p38 mitogen-activated protein kinase/Hsp27 pathway in multiple myeloma cell lines and inhibits paracrine tumour growth. Br J Haematol. 2007 February; 136(3):414-23.

Wang S, Yang J, Qian J, Wezeman M, Kwak L W, Yi Q. Tumor evasion of the immune system: inhibiting p38 MAPK signaling restores the function of dendritic cells in multiple myeloma. Blood. 2006 Mar. 15; 107(6):2432-9.

The contents of each patent and non-patent reference are incorporated herein by reference in their entirety.

What is claimed is:

1. A method of treating cancer in a subject in need thereof, the method consisting essentially of administering R-[5-Amino-1-(4-fluoro-phenyl)-1H-pyrazol-4-yl]-[3-(2,3-dihydroxy-propoxy)-phenyl]-methanone to the subject to enhance IL-12 production and/or inhibit IL-10 production; or a pro-drug and pharmaceutically acceptable salt thereof.

2. The method of claim 1, wherein the cancer is selected from the group consisting of breast cancer, pancreas cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteosarcoma, chondrosarcoma, Ewing's sarcoma, malignant fibrous histiocytoma, fibrosarcoma, multiple myeloma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, glioblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas.

3. The method of claim 1 wherein cancers treatable according to the invention include cancers of the breast, pancreas, skin, prostate, liver, lung, lymphoid system, bladder, kidney, brain, colon and bone.

4. The method of claim 1 wherein the cancer is selected from the group consisting of melanoma, prostate adenocarcinoma, lymphoma, pancreatic ductal carcinoma, renal carcinoma, hepatocellular carcinoma, small cell lung carcinoma, non-small cell lung carcinoma, urothelial cell carcinoma, colon carcinoma, glioblastoma, breast lobular or ductal carcinoma, osteosarcoma, chondrosarcoma, and multiple myeloma.

\* \* \* \* \*